US012746347B2

(12) United States Patent
Corbett

(10) Patent No.: US 12,746,347 B2

(45) **Date of Patent: *Sep. 29, 2026**

(54) INJECTABLE ADMINISTRATION COMPLIANCE PLATFORM

(71) Applicant: DATADOSE, LLC, Lexington, KY (US)

(72) Inventor: Jeremy Corbett, Lexington, KY (US)

(73) Assignee: DataDose, LLC, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/031,881

(22) Filed: Jan. 18, 2025

(65) Prior Publication Data

US 2026/0124402 A1 May 7, 2026

Related U.S. Application Data

(63) Continuation of application No. 19/031,031, filed on Jan. 17, 2025.

(Continued)

(51) Int. Cl.

*G16H 20/17* (2018.01)

*A61M 5/315* (2006.01)

(Continued)

(52) U.S. Cl.

CPC ...... *A61M 5/5086* (2013.01); *A61M 5/31566* (2013.01); *A61M 5/427* (2013.01);

(Continued)

(58) Field of Classification Search

None

See application file for complete search history.

(56) References Cited

U.S. PATENT DOCUMENTS

| | | | |
|---|---|---|---|
| 4,950,246 | A | 8/1990 | Muller |
| 7,300,418 | B2 | 11/2007 | Zaleski |

(Continued)

FOREIGN PATENT DOCUMENTS

| | | | |
|---|---|---|---|
| CA | 3140408 | A1 | 11/2020 |
| EP | 3991771 | A1 | 5/2022 |

(Continued)

OTHER PUBLICATIONS

Mahzabin, Rahnuma et al. "Blockchain associated machine learning and IoT based hypoglycemia detection system with auto-injection feature." ArXiv abs/2208.02222 (2022): n. pag. (Year: 2022).*

(Continued)

*Primary Examiner* — Emily Huynh

(74) *Attorney, Agent, or Firm* — Michael T. Abramson; Jordan IP Law, LLC

(57) ABSTRACT

A method, computer program product, and computer system for an injectable administration compliance platform for real-time monitoring and management of adherence to a program for administration of a set of injectables. The platform may include: a server to receive administration data from a wireless module associated with an intelligent injection device. The administration data may include at least one of: an injection device ID, a drug ID, a patient ID, a potency value, an administration completion flag, a timestamp, or temperature data. A database may store treatment schedules. An artificial intelligence module may: calculate a compliance score, and compare the compliance score to a compliance threshold to categorize the injection event. An alerts module may be included. A monitoring system may track user compliance in substantially real-time. A recommendation system may generate health suggestions. The platform may further include a reporting module, a verification module, and a dashboard.

20 Claims, 28 Drawing Sheets

Related U.S. Application Data

(60) Provisional application No. 63/715,505, filed on Nov. 1, 2024.

(51) Int. Cl.

| | |
|---|---|
| ***A61M 5/42*** | (2006.01) |
| ***A61M 5/50*** | (2006.01) |
| ***G09B 5/04*** | (2006.01) |
| ***G09B 5/06*** | (2006.01) |
| ***G16H 10/60*** | (2018.01) |
| ***G16H 40/63*** | (2018.01) |
| ***G16H 50/20*** | (2018.01) |

(52) U.S. Cl.

CPC ............... *G09B 5/04* (2013.01); *G09B 5/065* (2013.01); *G16H 10/60* (2018.01); *G16H 20/17* (2018.01); *G16H 40/63* (2018.01); *G16H 50/20* (2018.01); *A61M 2205/3327* (2013.01); *A61M 2205/3592* (2013.01); *A61M 2205/58* (2013.01); *A61M 2205/581* (2013.01); *A61M 2205/582* (2013.01); *A61M 2205/583* (2013.01)

(56) References Cited

U.S. PATENT DOCUMENTS 9,317,916 B1 * 4/2016 Hanina .................. G16H 20/10
9,623,191 B2 4/2017 Uber et al.
10,825,560 B1 11/2020 Berenson
10,911,515 B2 2/2021 Biasi et al.
11,102,304 B1 8/2021 Jain et al.
11,210,611 B2 12/2021 Kamen et al.
12,260,959 B1 3/2025 Minetti et al.
2001/0047281 A1 11/2001 Keresman, III et al.
2003/0036683 A1 2/2003 Kehr et al.
2003/0110060 A1 6/2003 Clementi
2007/0179453 A1 8/2007 Lim et al.
2007/0219503 A1 9/2007 Loop et al.
2007/0225653 A1 9/2007 Lim et al.
2009/0076338 A1 3/2009 Zdeblick et al.
2011/0009812 A1 1/2011 Brown
2012/0209243 A1 8/2012 Yan
2013/0023813 A1 1/2013 Roorda
2013/0023825 A1 1/2013 Edwards et al.
2013/0276785 A1 10/2013 Melker et al.
2013/0310756 A1 11/2013 Whalley et al.
2013/0338628 A1 12/2013 Robertson et al.
2014/0074454 A1 3/2014 Brown et al.
2014/0180711 A1 6/2014 Kamen et al.
2014/0207099 A1 7/2014 Nagar et al.
2015/0057611 A1 2/2015 Bureau
2015/0112703 A1 4/2015 Sysko et al.
2015/0174342 A1 6/2015 Mitrosky et al.
2015/0278924 A1 10/2015 Maurer et al.
2016/0012205 A1 1/2016 Saint et al.
2016/0042154 A1 2/2016 Goldberg et al.
2016/0171597 A1 6/2016 Todeschini
2016/0171777 A1 6/2016 Todeschini et al.
2016/0243318 A1 8/2016 Despa et al.
2016/0259913 A1 9/2016 Yu et al.
2017/0007765 A1 1/2017 Cowe et al.
2017/0076060 A1 3/2017 Pilkington et al.
2017/0095638 A1 4/2017 Young et al.
2017/0119969 A1 5/2017 McCullough et al.
2017/0136185 A1 5/2017 Rios et al.
2017/0146381 A1 5/2017 Eckel et al.
2017/0203030 A1 7/2017 Brewer et al.
2017/0245943 A1 8/2017 Foster et al.
2017/0262604 A1 9/2017 Francois
2017/0325091 A1 11/2017 Freeman et al.
2017/0357775 A1 12/2017 Ekin
2018/0017531 A1 1/2018 Juhnke et al.
2018/0085517 A1 3/2018 Laurence et al.
2018/0113985 A1 4/2018 Gandy et al.
2018/0133400 A1 5/2018 Almoumen
2018/0166163 A1 6/2018 Sudharsan
2018/0182491 A1 6/2018 Belliveau et al.
2018/0193564 A1 7/2018 Dahmani
2018/0308569 A1 10/2018 Luellen
2018/0333543 A1 11/2018 Diaz et al.
2018/0369488 A1 12/2018 Carlsson et al.
2019/0054247 A1 2/2019 Dantsker et al.
2019/0060577 A1 2/2019 Vallis
2019/0130792 A1 5/2019 Rios et al.
2019/0209777 A1 7/2019 O'Connell et al.
2019/0247050 A1 8/2019 Goldsmith
2019/0262534 A1 8/2019 Agard et al.
2019/0282761 A1 9/2019 Wilson et al.
2020/0016331 A1 1/2020 Lee et al.
2020/0061301 A1 2/2020 Hatamian et al.
2020/0082327 A1 3/2020 Arefieg
2020/0086046 A1 * 3/2020 Corbett .................. G16H 20/17
2020/0093993 A1 3/2020 O'Rourke et al.
2020/0139053 A1 5/2020 Faught et al.
2020/0226951 A1 7/2020 Rios et al.
2020/0289751 A1 9/2020 Despa et al.
2020/0303047 A1 9/2020 Bostic et al.
2020/0350052 A1 11/2020 Saint et al.
2020/0364801 A1 11/2020 Basra
2020/0390596 A1 12/2020 Chalberg, Jr. et al.
2021/0008294 A1 1/2021 Gentz
2021/0060246 A1 3/2021 Weydt et al.
2021/0217516 A1 7/2021 Nash et al.
2021/0260289 A1 8/2021 Kamath et al.
2021/0288950 A1 9/2021 Rodriguez Bravo et al.
2022/0023391 A1 1/2022 Michelich et al.
2022/0031956 A1 2/2022 Helmer
2022/0051778 A1 2/2022 Kühni et al.
2022/0183915 A1 6/2022 Augustine et al.
2022/0301681 A1 9/2022 Coetzee
2022/0336074 A1 10/2022 Bakos et al.
2023/0081577 A1 3/2023 Walker et al.
2023/0191036 A1 * 6/2023 Corbett .................. G16H 20/17
2023/0298723 A1 9/2023 Mercolino et al.
2023/0302224 A1 9/2023 Prince et al.
2023/0330328 A1 10/2023 Moberg et al.
2023/0368226 A1 11/2023 Mestres et al.
2023/0386677 A1 11/2023 Ferro et al.
2023/0414432 A1 12/2023 Augustine et al.
2023/0414433 A1 12/2023 Augustine et al.
2024/0157045 A1 5/2024 Kostal et al.
2024/0232031 A1 7/2024 Kang et al.
2024/0285956 A1 8/2024 Forsell
2025/0000453 A1 1/2025 Lettman et al.
2025/0050014 A1 2/2025 Shin et al.
2025/0054615 A1 2/2025 Ronen et al.
2025/0329451 A1 10/2025 Minetti et al.
2026/0079511 A1 3/2026 Roychoudhury et al.

FOREIGN PATENT DOCUMENTS

WO 2006060572 A1 6/2006
WO 2016210404 A1 12/2016
WO 2017156523 A1 9/2017
WO 2018009509 A2 1/2018
WO 2018106475 A1 6/2018
WO 2020236481 A1 11/2020
WO WO-2021237085 A1 * 11/2021 ............. G16H 20/17

OTHER PUBLICATIONS

Restriction Requirement Office Action for U.S. Appl. No. 17/926,157 dated Sep. 24, 2025, 6 pages.

Notice of Allowance for U.S. Appl. No. 19/031,940 dated Oct. 17, 2025, 21 pages.

Final Office Action for U.S. Appl. No. 17/724,177, dated Oct. 29, 2025, 32 pages.

Extended European Search Report, Application No. 21808546.2, dated May 23, 2024, 8 pages.

Office Action for U.S. Appl. No. 17/724,177, dated Apr. 11, 2024, 11 pages.

(56) References Cited

OTHER PUBLICATIONS

Office Action for U.S. Appl. No. 17/724,177, dated Oct. 22, 2024, 13 pages.
Office Action for U.S. Appl. No. 16/131,749, dated Apr. 1, 2020, 9 pages.
Office Action for U.S. Appl. No. 16/131,749, dated Oct. 1, 2020, 11 pages.
Office Action for U.S. Appl. No. 16/131,749, dated Mar. 2, 2021, 13 pages.
Office Action for U.S. Appl. No. 16/131,749, dated Sep. 16, 2021, 10 pages.
Notice of Allowance for U.S. Appl. No. 16/131,749, dated Jan. 13, 2022, 7 pages.
Written Opinion of the International Searching Authority for Application No. PCT/US21/33646, dated Oct. 20, 2021, 10 pages.
International Search Report for Application No. PCT/US21/33646, dated Oct. 20, 2021, 4 pages.
Non-Final Office Action for U.S. Appl. No. 17/724,177 dated Apr. 21, 2025, 9 pages.
Restriction Requirement Office Action for U.S. Appl. No. 19/031,780 dated May 19, 2025, 6 pages.
Restriction Requirement Office Action for U.S. Appl. No. 19/031,836 dated Apr. 25, 2025, 6 pages.
Non-Final Office Action for U.S. Appl. No. 19/031,836 dated Jul. 18, 2025, 17 pages.
Restriction Requirement Office Action for U.S. Appl. No. 19/031,854 dated May 9, 2025, 6 pages.
Restriction Requirement Office Action for U.S. Appl. No. 19/031,862 dated May 9, 2025, 6 pages.
Non-Final Office Action for U.S. Appl. No. 19/031,940 dated Apr. 11, 2025, 25 pages.
Final Office Action for U.S. Appl. No. 19/031,940 dated Jul. 3, 2025, 13 pages.
Notice of Allowance for U.S. Appl. No. 19/031,780 dated Dec. 29, 2025, 20 pages.
Non-Final Office Action or U.S. Appl. No. 19/314,966 dated Dec. 31, 2025, 42 pages.
Notice of Allowance for U.S. Appl. No. 19/315,011 dated Jan. 7, 2026, 39 pages.
Examination Report dated Nov. 17, 2025 for European Application No. 21808546.2, 5 pages.
Final Office Action for U.S. Appl. No. 19/031,836 dated Nov. 26, 2025, 26 pages.
Non-Final Office Action for U.S. Appl. No. 19/280,969 dated Dec. 1, 2025, 38 pages.
Non-Final Office Action for U.S. Appl. No. 19/281,013 dated Dec. 11, 2025, 35 pages.
Non-Final Office Action for U.S. Appl. No. 19/281,035 dated Dec. 11, 2025, 29 pages.
Notice of Allowance for U.S. Appl. No. 19/031,854 dated Jul. 28, 2025, 32 pages.
Notice of Allowance for U.S. Appl. No. 19/031,862 dated Jul. 29, 2025, 43 pages.
Non-Final Office Action for U.S. Appl. No. 19/031,780 dated Aug. 6, 2025, 30 pages.
Notice of Allowance for U.S. Appl. No. 19/314,936 dated Jan. 13, 2026, 30 pages.
Notice of Allowance for U.S. Appl. No. 17/724,177 dated Jan. 13, 2026, 12 pages.
Non-Final Office Action for U.S. Appl. No. 17/926,157 dated Jan. 21, 2026, 53 pages.
Notice of Allowance for U.S. Appl. No. 19/315,027 dated Feb. 6, 2026, 37 pages.
Notice of Allowance for U.S. Appl. No. 19/031,780 dated Feb. 27, 2026, 26 pages.
Final Office Action for U.S. Appl. No. 19/280,969 dated Mar. 4, 2026, 38 pages.
Notice of Allowance for U.S. Appl. No. 17/724,177 dated Mar. 10, 2026, 25 pages.
Non-Final Office Action for U.S. Appl. No. 19/031,870 dated Mar. 25, 2026, 52 pages.
Notice of Allowance for U.S. Appl. No. 19/314,864 dated Mar. 27, 2026, 45 pages.
Final Office Action for U.S. Appl. No. 19/281,013 dated Mar. 30, 2026, 29 pages.
Final Office Action for U.S. Appl. No. 19/281,035 dated Mar. 30, 2026, 32 pages.
Non-Final Office Action for U.S. Appl. No. 19/031,928 dated Apr. 7, 2026, 53 pages.
Non-Final Office Action for U.S. Appl. No. 19/315,011 dated Apr. 7, 2026, 15 pages.
Notice of Allowance for U.S. Appl. No. 19/031,940 dated Apr. 8, 2026, 28 pages.
Notice of Allowance for U.S. Appl. No. 19/031,780 dated Apr. 9, 2026, 17 pages.
Notice of Allowance for U.S. Appl. No. 17/724,177 dated Apr. 9, 2026, 16 pages.
Notice of Allowance for U.S. Appl. No. 19/314,936 dated Apr. 10, 2026, 15 pages.
Notice of Allowance for U.S. Appl. No. 19/031,836 dated Apr. 17, 2026, 23 pages.
Non-Final Office Action for U.S. Appl. No. 19/031,911 dated Apr. 20, 2026, 55 pages.
Final Office Action for U.S. Appl. No. 19/314,966 dated Apr. 20, 2026, 24 pages.
Non-Final Office Action for U.S. Appl. No. 19/031,890 dated Apr. 21, 2026, 53 pages.
Notice of Allowance for U.S. Appl. No. 19/451,171 dated Apr. 22, 2026, 37 pages.
Faisal S, Samoth D, Aslam Y, Patel H, Park S, Baby B, Patel T. Key Features of Smart Medication Adherence Products: Updated Scoping Review. JMIR Aging. Dec. 19, 2023;6:e50990. doi: 10.2196/50990. PMID: 38113067; PMCID: PMC10762620 (Year: 2023).
Notice of Allowance for U.S. Appl. No. 19/451,472 mailed May 13, 2026, 48 pages.
International Search Report and Written Opinion for PCT Application No. PCT/US2025/053140 mailed Jun. 10, 2026, 39 pages.

* cited by examiner

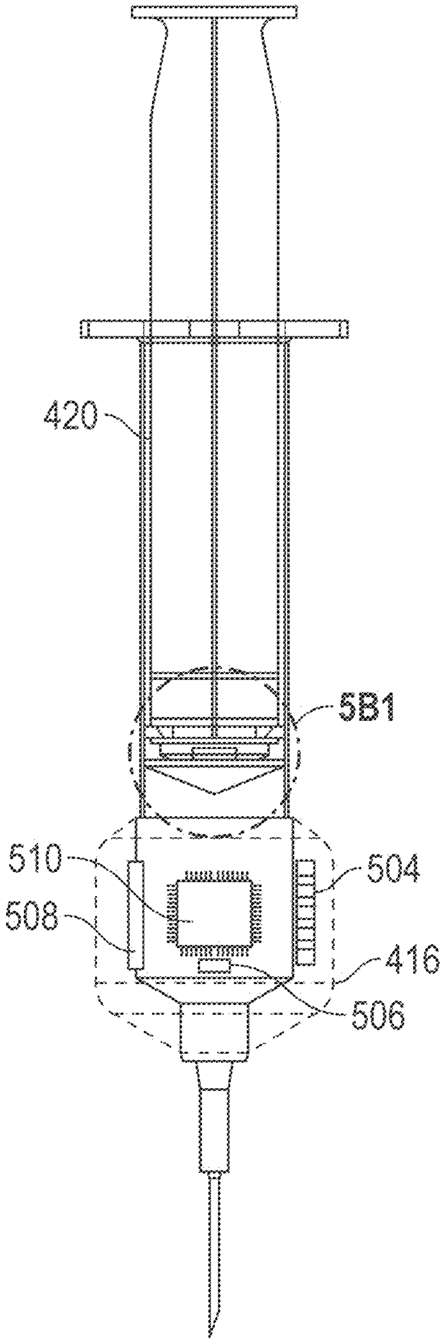
FIG. 5B
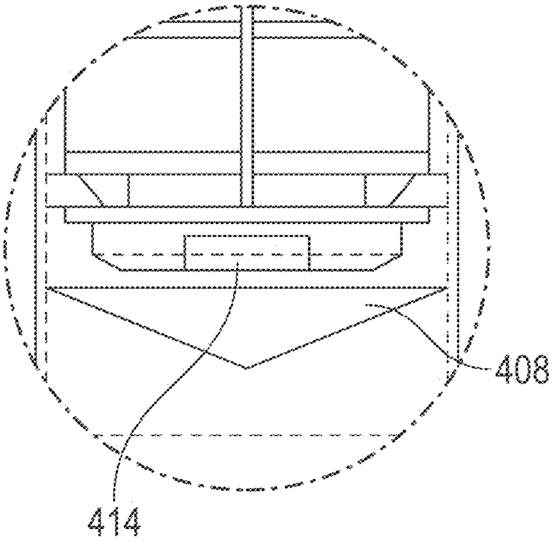
FIG. 5B1

INJECTABLE ADMINISTRATION COMPLIANCE PLATFORM

CROSS-REFERENCE TO RELATED APPLICATIONS

This application is a continuation of U.S. patent application Ser. No. 19/031,031, filed on Jan. 17, 2025, which claims the benefit of U.S. provisional application No. 63/715,505, filed on Nov. 1, 2024, which is hereby incorporated by reference in its entirety.

FIELD

The present disclosure relates generally to a management platform for injection devices, such as syringes, and, more particularly, to data reporting regarding administration completion of an injectable pharmaceutical.

BACKGROUND

Understanding administration of drugs and their interaction in the healthcare ecosystem are important in delivering beneficial patient care. Applicant appreciates that regular pharmaceutical therapy and a need for real time data management related to both timing of and compliance in dosing bundled with increased information sharing across the care continuum can provide valuable insight for improving care and, in turn, reducing fraud, waste, and abuse.

SUMMARY

In some aspects, the techniques described herein relate to an injectable administration compliance platform for real-time monitoring and management of adherence to a program for administration of a set of injectables, the platform including: a server configured to receive administration data from a wireless module associated with an intelligent injection device, wherein the administration data includes at least one of: an injection device ID, a drug ID, a patient ID, a potency value, an administration completion flag, a timestamp, or temperature data; a database configured to store treatment schedules associated with injectable medication administration; an artificial intelligence module configured to: calculate a compliance score for an injection event based on conformance of the administration data to at least one criterion of a treatment schedule, and compare the compliance score to a compliance threshold metric to categorize the injection event as compliant, non-compliant or indeterminate; an alerts module configured to generate and send notifications to a user based on the categorization of injection events; a monitoring system configured to track user compliance with prescribed medication regimens in substantially real-time; a recommendation system configured to generate personalized health suggestions based on received patient data; a reporting module configured to generate detailed adherence reports for healthcare providers; a verification module configured to ensure proper medication administration by validating user identity; and a dashboard configured to provide visual information related to injection administration compliance; wherein the platform is configured to: receive data from at least one of: IoT devices, wearable devices, or electronic medical record systems, process the received data in combination with the administration data to make medical determinations, and automatically determine changes to at least one of: dosage, timing, and attributes of injection based on the processed data.

In some aspects, the techniques described herein relate to a platform, wherein the injectable administration program is prescribed by a physician and stored in the treatment schedule database.

In some aspects, the techniques described herein relate to a platform, wherein the platform receives administration data collected from an intelligent injection device, wherein the administration data includes at least one of: a substance type, substance amount ejected, duration of substance release, temperature of substance, and substance identifier.

In some aspects, the techniques described herein relate to a platform, wherein the platform uses the intelligent injection device data to make medical treatment determinations, wherein the medical treatment determinations include at least one of: adjustments to patient treatment based on administration data and changes to dosage or timing based on recorded patient data.

In some aspects, the techniques described herein relate to a platform, wherein the platform uses the intelligent injection device data to make insurance coverage determinations, wherein the insurance coverage determinations include at least one of: increasing or lowering insurance rates and claim payouts based on whether the administration data indicates legitimate or fraudulent injection.

In some aspects, the techniques described herein relate to a platform, wherein the platform uses the intelligent injection device data to make manufacturing determinations, wherein the manufacturing determinations include at least one of: design adjustments, assembly adjustments, and factory adjustments based on the administration data.

In some aspects, the techniques described herein relate to a platform, wherein the platform uses the intelligent injection device data in connection with clinical trials of injectable medications, wherein the platform records exact injection timing to ensure accurate reporting and adherence to clinical trial protocols.

In some aspects, the techniques described herein relate to a platform, wherein the platform uses the intelligent injection device data to make legal and regulatory compliance determinations through a compliance/reporting/validation system that ensures all regulatory requirements are met.

In some aspects, the techniques described herein relate to a platform, wherein the legal and regulatory compliance determination is based at least in part on location-specific or jurisdiction-specific constraints or requirements through a privacy/governance system that protects patient data according to legal standards in regions with stringent data protection laws.

In some aspects, the techniques described herein relate to an intelligent dosing platform, wherein the platform is integrated with an emergency medical record (EMR) system and/or an emergency health record (EHR) system, wherein the integration enables automatic population of EMR/EHR fields with administration data.

In some aspects, the techniques described herein relate to an intelligent dosing platform, wherein the platform is integrated with a clinical provider or caregiver portal configured to enable healthcare providers to monitor compliance remotely and make treatment and coverage decisions based on stored treatment data.

In some aspects, the techniques described herein relate to an intelligent dosing platform, wherein the platform is integrated with a patient portal configured to enable patients to: manage injection schedules, view medication history, manage appointments, refill prescriptions, and communicate with healthcare providers.

In some aspects, the techniques described herein relate to an intelligent dosing platform, wherein a set of events from an intelligent injection device are automatically delivered to populate one or more fields of the EMR/EHR system, wherein the events include administration data including at least one of: an injection device ID, a drug ID, a patient ID, a potency value, an administration completion flag, a time-stamp, and temperature data.

A more complete understanding of the disclosure will be appreciated from the description and accompanying drawings and the claims, which follow.

BRIEF DESCRIPTION OF THE DRAWINGS

The accompanying drawings, which are included to provide a better understanding of the disclosure, illustrate embodiment(s) of the disclosure and together with the description serve to explain the principle of the disclosure. In the drawings:

FIG. 5B is a diagram that illustrates the reporting components of the reporting injection device according to some embodiments of the present disclosure.

FIG. 5B1 is a diagram that illustrates a zoomed-in partial view of the reporting components of the reporting injection device of FIG. 5B.

DETAILED DESCRIPTION

Figure 1:
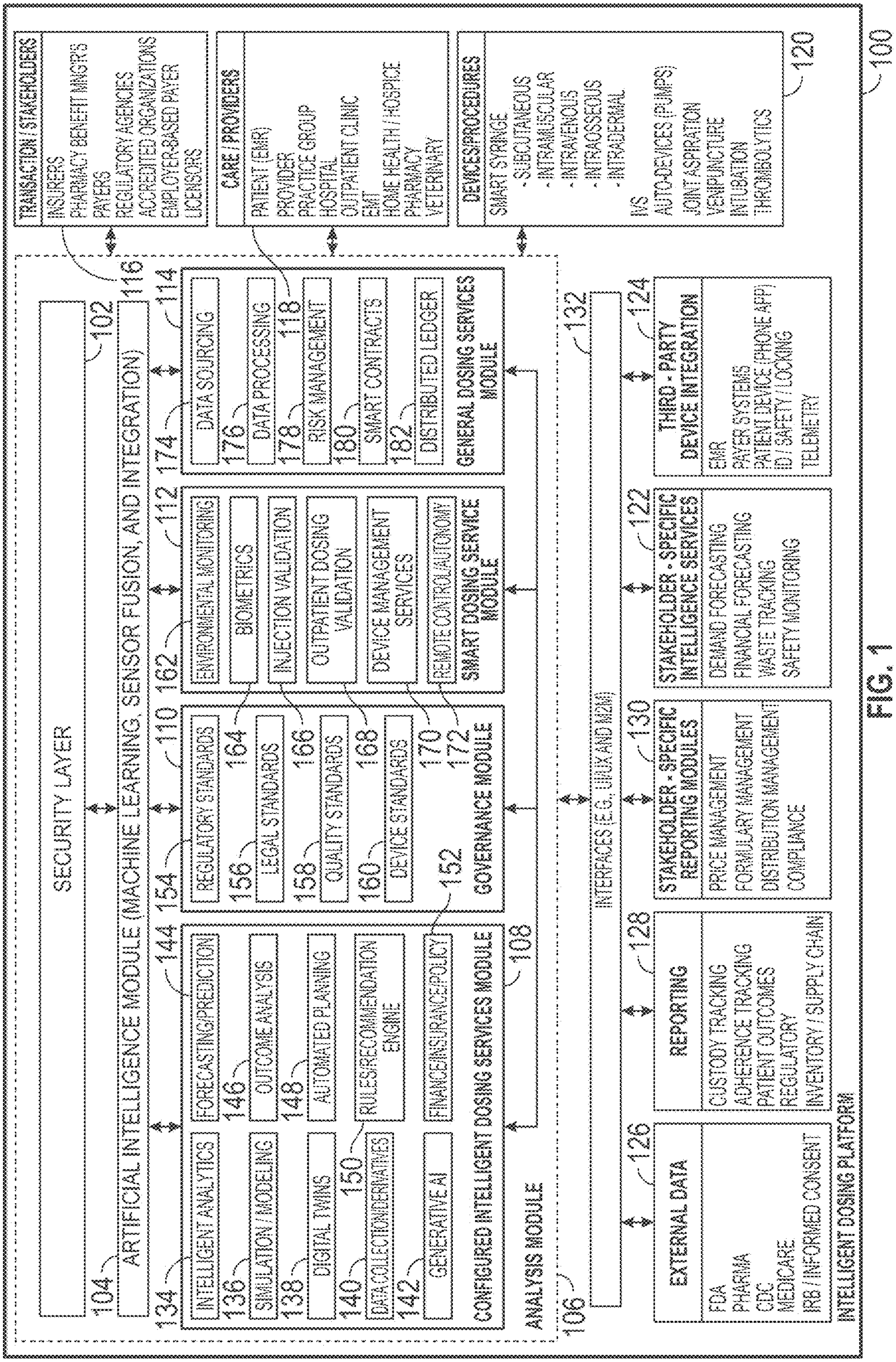
FIG. 1 is a diagram illustrating an intelligent dosing platform.

The present disclosure relates generally to a management platform for intelligent injection devices, such as syringes, intravenous devices, automatic injectable drug delivery systems and to the management, control, analysis and reporting regarding the handling and administration of injectable pharmaceuticals and the like. Embodiments of the present disclosure may bring novel biologics compliance to the market for the first time. Insurers, employers, health care providers, and loved ones may benefit when patient care plans receive a monocular focus on quality and completion.

Embodiments of the present disclosure may provide those with acute and chronic conditions in need of regular pharmaceutical therapy, such as an ongoing course of life-saving injectable drugs, with real-time data management related to both timing of and compliance in dosing. Information shared across the care continuum may provide valuable insight into how and when providers should intervene, and may further eliminate fraud, waste, and abuse within this expensive space. Embodiments of the present disclosure may drive compliance, illuminate opportunities for intervention, and save money in the pharmaceutical space with a great need for innovation and within a population that deserves the best care available. For example, many biologics may have a high cost per injection. The Humira™, Enbrel™, and/or Remicade™ biologics may be used as an immunosuppressant to treat autoimmunity. These biologics may be expensive. For example, the Humira™ biologic may cost up to $5,000 per injection. Furthermore, the biologics may be temperature sensitive. The Humira™ and Enbrel™ biologics may be recommended to be stored between 2 and 8 degrees Celsius, without freezing, and may be kept at room temperature for up to 14 days. Such a temperature range corresponding to the temperature tolerance of a pharmaceutical may be referred to as a predetermined temperature range. The time period that a pharmaceutical may exceed the predetermined temperature range may be referred to as a time tolerance. Regarding some pharmaceuticals, such as biologics, the time tolerance may exclude freezing. The Remicade™ biologic may be recommended to be stored between 2 and 8 degrees Celsius, without freezing, and may be kept at room temperature for 24 hours. Due to the sensitivity of these biologics, a pharmacist may refuse inventory shipments where cold chain storage has been broken. These biologics may be shipped preloaded into intelligent injection devices.

Information associated with an injectable medical device, including a syringe, an intravenous delivery system, an automatic injectable drug delivery system, such as an insulin pump, and the like and information associated with the practices, processes, planning, supply, and prediction of intelligent injection device usage and outcomes has historically been collected, stored and managed by a plurality of remote medical, pharmaceutical and reimbursement entities (e.g., insurers), each with its own analytic interest, making the centralized usage of such injectable medical device data difficult, and the creation of derivative data and analyses that may derive from such centralized usage unrealized. As a result, understanding the knowledge that is inherent in intelligent injection device medical information is limited, as is putting to use such intelligence for the optimized dosage management of an individual's intelligent injection device, its usage and history, device product management and supply oversight, best practices for the delivery and usage of intelligent injection devices, and other outcomes. Conventional data collection and analytic techniques for tracking the delivery, usage and outcomes for intelligent injection devices may lack validation for data collected on individual users and/or clinics, including human and veterinary clinics, making tracking continuity of care across medical facilities difficult and dosage information unreliable. Such data can therefore contain errors, making the data lack utility and misguide clinical care. Thus, in conventional medical information systems, the actual usage of intelligent injection devices in the field, such as at tertiary care facilities, outpatient clinics, veterinary clinics, emergent care and the like, may not be properly captured and data related to such usage may be inaccurate. Conventional intelligent injection device data may lack validity in part because of the nature of the facility administering the medicine using the injectable and/or the personnel in charge or administering or recording the injectable usage. For example, tertiary care centers may fail to record detailed dosing information for a patient which negatively impacts subsequent review and care for the patient under, for example, their primary care physician's supervision. Intelligent injection device usage and outcomes may be dynamic and complex, occurring in a fast-moving medical environment with inherent data collection challenges and/or occurring in an individual patient's home where the patient is not trained or knowledgeable about the importance of recording dosage data. Clinical practices and facilities, including within human and veterinary clinics, may be dissimilar, adding complexity for modeling intelligent injection device usage. Valid chain of custody data may not be available, calling into question if a dose about to be administered to a patient is held within an intelligent injection device that has been appropriately stored and shipped in an environment suitable for the proper maintenance of the medication within the intelligent injection device, as factors such as temperature control and variation may damage some medications.

A management platform for intelligent injection devices 400 (hereinafter also referred to as the "intelligent dosing platform" and "platform"), and examples of medical intelligent injection device management, analysis, prediction and forecasting are described herein. Such examples include, but are not limited to, providing guidance to individual clinicians and/or patients ("patient(s)" as used herein refers to anyone receiving, managing, or interacting with an intelligent injection device as part of a course of treatment or ongoing medical care, and includes human patients being served by medical professionals or those providing self-care (e.g., providing their own injections of insulin) and veterinary or animal patients, and includes animal patients being served by veterinary professionals or lay persons (e.g., administration of vaccines on a farm by farm or other personnel)) to make effective injectable medical device choices, plans and practices that enable, for example, more accurately predicting the need for supplies, the course of a patient's treatment, dose-response measures, and identifying and classifying intelligent injection devices, products, actions and practices that might impact and/or optimize their usage (as used herein, "optimize" and "optimization" refer to an improvement and does not necessarily require a "best" result.) Using the intelligent dosing platform 100, as disclosed herein, may allow an individual patient, a clinician, a healthcare facility, pharmaceutical corporation, manufacturer and/or distributor or some other entity to more accurately collect and maintain intelligent injection device data in a confidential format and system and better manage their intelligent injection device practices.

Other examples of intelligent injection device management, analysis, prediction and forecasting using the intelligent dosing platform 100, described herein, include providing time- and location-specific (e.g., clinic-specific) intelligence rather than general information that may or may not be applicable to a given patient, clinic, medication, or the like. In embodiments, the intelligent dosing platform 100, described herein, may provide predictions from post-processed data that is determined at least in part by real-time conditions associated with a clinical practice or decision.

FIG. 1 depicts a block diagram of an intelligent dosing platform 100 for assisting medical intelligent injection device planning, decision making, procurement, analysis and tracking. In embodiments, the intelligent dosing platform 100 may include a security layer 102, an AI/ML module 104, and an analysis module 106. The analysis module 106 may include a configured intelligent dosing services module 108, a governance module 110, a smart dosing service module 112, and a general dosing service module 114. The intelligent dosing platform 100 may be further associated with stakeholders and related transactions 116, healthcare professionals and other type of care providers 118, facilities related to intelligent injection devices and procedures 120, or some other facility, process or data source.

In embodiments, the platform 100 may utilize a plurality of interfaces 132 to interface between the analysis module 106 and a plurality of external services, such as external data 126, reporting 128, stakeholder-specific reporting modules 130, stakeholder-specific intelligence functions 122, and/or third-party device integration 124. The interfaces 132 may be or include, for example, user interface/user experience (UI/UX) components and/or machine-to-machine (M2M) components.

In embodiments, the intelligent dosing platform 100 may utilize external data 126 from a plurality of sources, including but not limited to the FDA, pharmaceutical entities, the Centers for Disease Control (CDC), government programs like Medicaid or Medicare, and/or an institutional review board (IRB) or other entity related to research, clinical trials and the like. The intelligent dosing platform 100 may include reporting functionalities 128, including but not limited to custody tracking, adherence tracking, tracking and reporting patient outcomes, reporting for regulatory purposes, inventory/supply chain reporting and the like.

In embodiments, the intelligent dosing platform 100 may include stakeholder-specific reporting modules 130, including but not limited to price management, formulary management, distribution management, compliance, or some other reporting module type.

In embodiments, the intelligent dosing platform 100 may include stakeholder-specific intelligence functions 122, including but not limited to demand forecasting, financial forecasting, waste tracking, safety monitoring or some other intelligent services type.

In embodiments, the intelligent dosing platform 100 may include third-party device integration 124, including but not limited to electronic medical records (EMRs), payer systems, patient devices (e.g., phone applications), device ID/safety/locking, telemetry, or some other third-party device integration type.

In embodiments, the security layer 102 may be configured to provide secured access between the analysis module and/or external systems and facilities, as described herein, for example when an external system presents valid credentials, which are authenticated by the security layer. If the external system does not present valid credentials, the security layer may deny communications between the external system and the analysis module. In various implementations, the security layer may facilitate the analysis module to read and write to external data sources, such as public and private data sources as described herein. In embodiments, the public and private data may include, but are not limited to, government data (e.g., Medicare, Food and Drug Administration (FDA) drug use guidelines and the like), data from intelligent injection devices (e.g., syringes, intravenous devices (IVs), and the like), private industry data (e.g., pharmaceutical data on best practices, contraindications, dosing, and the like), or some other type of data.

In embodiments, the analysis module 106 may include a machine learning (ML), artificial intelligence (AI), data processing, fusion, and integration module 104 (hereinafter also referred to as the "machine learning and artificial intelligence module," "artificial intelligence module," "AI module," and "AI/ML module"), for assisting intelligent injection device planning, decision making and procurement. In various implementations, the machine learning, artificial intelligence, data processing, fusion, and integration module may include intelligence functions 202, intelligent analytics and the like, as disclosed herein.

In embodiments, the configured intelligent dosing services module 108 includes but is not limited to an intelligence analytics module 134, a simulation/modeling module 136, a digital twins module 138, a data collection/derivatives module 140, a generative AI module 142, a forecasting/prediction module 144, an outcome analysis module 146, an automated planning module 148, a rules and recommendation engine 150, and a finance/insurance/policy module 152.

In embodiments, the governance module 110 includes but is not limited to a regulatory standards module 154, a legal standards module 156, a quality standards module 158, and a device standards module 160.

In embodiments, the smart dosing service module 112 includes but is not limited to an environmental monitoring module 162, a biometrics module 164, an injection validation module 166, an outpatient dosing validation module 168, a device management services module 170, and a remote control/autonomy module 172.

In embodiments, the general dosing service module 114 includes but is not limited to a data sourcing module 174, a data processing module 176, a risk management module 178, a smart contracts module 180, and a distributed ledger module 182.

Figure 2:
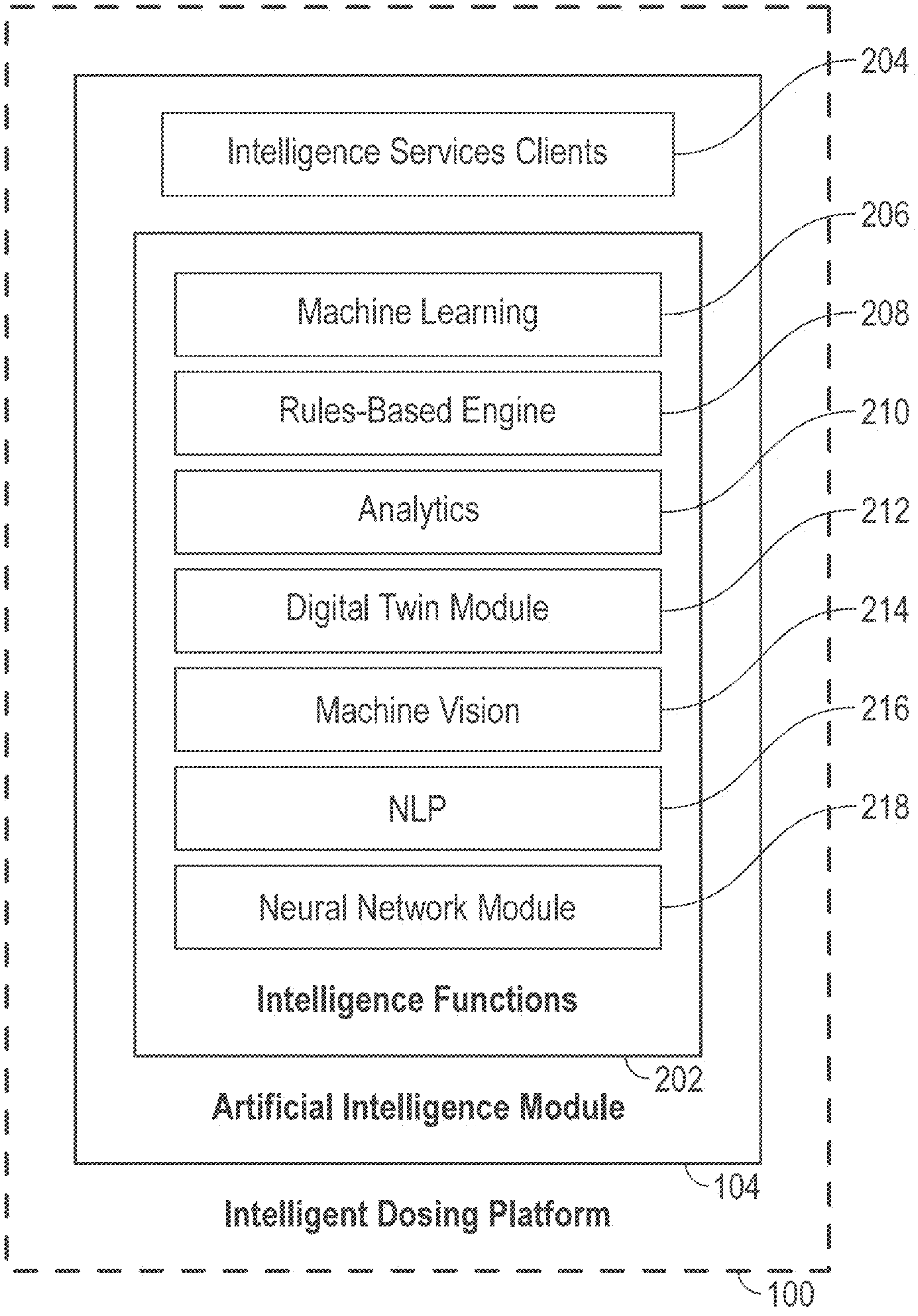
FIG. 2 is a diagram illustrating intelligence controller and intelligence functions of an intelligent dosing platform.

Referring to FIG. 2, in embodiments, the platform 100 may include one or more intelligence functions 202 and/or intelligence service clients 204. In some embodiments, the intelligence functions 202 may be adapted to be at least partially replicated in respective intelligence service clients 204. In these embodiments, an individual intelligence service client 204 may include some or all of the capabilities of the intelligence functions 202, whereby the intelligence service may be adapted for the specific functions performed by the subsystems of the intelligence service client 204. Additionally or alternatively, in some embodiments, the intelligence functions 202 may be implemented as a set of microservices, such that different intelligence service clients 204 may leverage the intelligence functions 202 via one or more APIs exposed to the intelligence service clients 204, such as intelligence service clients 204 that are directed towards a particular data field or task(s), such as intelligence service clients 204 used for monitoring, analyzing and reporting on intelligent injection devices and equipment, IoT sensors, and the like. In these embodiments, the intelligence functions 202 may be configured to perform various types of intelligence functions 202 that may be adapted for different intelligence clients. In either of these configurations, an intelligence service client 204 may provide an intelligence request to the intelligence functions 202, whereby the request is to perform a specific intelligence task (e.g., a decision, a recommendation, a report, an instruction, a classification, a prediction, a training action, a natural language processing (NLP) request, or the like). In response, the intelligence functions 202 may execute the requested intelligence task and return a response to the intelligence service client 204. Additionally, or alternatively, in some embodiments, the intelligence functions 202 may be implemented using one or more specialized chips (e.g., chips adapted to particular analytics, equipment, and the like) that are configured to provide AI assisted microservices such as data processing, diagnostics, location and orientation, chemical analysis, data processing, and so forth.

In embodiments, the intelligent dosing platform 100 may include a machine learning and artificial intelligence module 104. In embodiments, artificial intelligence functions 202 may receive an intelligence request from an intelligence service client 204 and any required data to process the request from the intelligence service client 204. In response to the request and the specific data, one or more implicated artificial intelligence modules 104 may perform the intelligence task and output an "intelligence response." Examples of intelligence module responses may include a decision (e.g., a control instruction, a proposed action, machine-generated text, and/or the like), a prediction (e.g., a predicted meaning of a text snippet, a predicted outcome associated with a proposed action, a predicted fault condition, and/or the like), a classification (e.g., a classification of an object in an image, a classification of a spoken utterance, a classified fault condition based on sensor data, and/or the like), and/or other suitable outputs of an artificial intelligence system. For example, data relating to a proposed injection of a specific patient with a specific medication may be analyzed by the platform and compared to historical injection data from other injection events for the purpose of identifying a comparable acceptable dosage to administer, an acceptable protocol for timing of injection, an approval regarding the proposed medication to administer, or some other confirmation or validation to proceed with an injection. Additional data relating to the proposed injection may be used and analyzed by the analysis module 106 and intelligence functions 202 to, for example, identify appropriate written instructions to present the patient, a multimedia file to present the patient on how to correctly administer the injection, or some other activity.

In embodiments, the machine learning and artificial intelligence module may include an ML module 206, a rules-based module 208, intelligence analytics module 134, a digital twin module 212, a machine vision module 214, a natural language processing (NLP) module 216, and/or a neural network module 218. It is appreciated that the foregoing are non-limiting examples of intelligent dosing platform modules, and that some of the modules may be included or leveraged by other artificial intelligence modules. For example, the NLP module 216 and the machine vision module 214 may leverage different neural networks that are part of the neural network module 218 in performance of their respective functions.

It is further noted that in some scenarios, the artificial intelligence module 104 may also be an intelligence client. For example, a rules-based intelligence module 208 may request an intelligence task from an ML module 206 or a neural network module 218, such as requesting a confirmation of the administration of a correct dosage following an injection event. In this example, the rules-based module 208 may be an intelligence service client that uses data related to the injection event to determine whether to take a specified action. In another example, a machine vision module 214 may request a digital twin of a specified intelligent injection device, such as a specific syringe type, from a digital twin module 212, such that the ML module 206 may request specific data from the digital twin, such as a dose administration log from during an injection event using a specific syringe model, as features to train a machine-learned model for dosing characteristics of a specific intelligent injection device.

In embodiments, an intelligence task may require specific types of data to respond to the request. For example, a task may require one or more sensor data inputs (and potentially other data) to classify an injection event (e.g., range of syringe "plunger" movement, and the like) to determine features within the set of intelligent injection device features (such as locations of key syringe components, device instructions, parameters of motion, changes in status, and many others), and the like. In another example, an NLP task may require audio of speech and/or text data (and potentially other data) to determine a meaning or other element of the speech and/or text, for example a patient's request to administer a dose using an intelligent syringe that is associated with the platform 100 and begin an authentication protocol to unlock the syringe to enable a medication delivery to the patient. In yet another example, an AI-based control task (e.g., movement of an element on an intelligent injection device) may require additional data (e.g., approvals, validation, confirmation of appropriate medication within the intelligent injection device, patient authentication, and/or the like) and/or a motion plan to make a decision as to how to control the motion of an intelligent injection device, such as angle of entry, depth of entry and the like.

In embodiments, the platform 100 may process an analytics-based reporting task requiring data from a number of different databases to generate an analysis and/or report. Thus, tasks that can be performed by the intelligence functions 202 may require, or benefit from, specific intelligence service inputs. In some embodiments, the intelligence functions 202 may be configured to receive and/or request specific data from the intelligence service inputs to perform a respective intelligence task. For example, a physician may want to restrict analysis and recommendations received from the platform 100 on validating a patient's past dosing events and requirements and amounts to only those inputs that apply to the specific medical intervention planned and/or time-constrained to report only on those dosage events recent enough to have relevance to a planned medical intervention. Additionally, or alternatively, the requesting intelligence service client may provide the specific data in the request. For instance, the intelligence functions 202 may expose one or more APIs to the intelligence clients, whereby a requesting client may provide the specific data in the request via the API. Examples of intelligence service inputs may include, but are not limited to, sensors that provide sensor data, video streams, audio streams, databases, data feeds, human input, and/or some other suitable data.

In embodiments, intelligence modules may include and provide access to an ML module 206 that may be integrated into or be accessed by one or more intelligence service clients 204. In embodiments, the ML module 206 may provide machine-based learning capabilities, features, functions, and algorithms for use by an intelligence service client such as training ML models, leveraging ML models, reinforcing ML models, performing various clustering techniques, feature extraction, and/or the like. In examples, an ML module 206 may provide machine learning computing, data storage, and feedback infrastructure to a simulation system (e.g., simulations of dosage administration using a plurality of syringe types, and the like). The ML module 206 may also operate cooperatively with other modules, such as the rules-based module 208, the machine vision module 214, and/or the like. For example, a nurse or other care giver may set rules relating to cost allocation for injectable medication administration such that some data and/or analyses are excluded from the analytics because the implementation of the resulting recommendations would exceed a cost threshold and/or violate a rule, such as parceling out dose administration across too many intelligent injection devices (e.g., syringes) when the same dose administration may be accomplished using fewer devices if, for example, correctly timed.

In embodiments, the ML module 206 may define one or more machine learning models for performing analytics, simulation, decision making, and predictive analytics related to data processing, data analysis, simulation creation, and simulation analysis of one or more components or subsystems of an intelligence service client. In embodiments, the machine learning models may be algorithms and/or statistical models that perform specific tasks without using explicit instructions, relying instead on patterns and inference. The machine learning models may build one or more mathematical models based on training data to make predictions and/or decisions without being explicitly programmed to perform the specific tasks. In example implementations, machine learning models may perform classification, prediction, regression, clustering, anomaly detection, recommendation generation, and/or other tasks.

In embodiments, the machine learning models may perform various types of classification based on the input data. Classification is a predictive modeling problem where a class label is predicted for a given example of input data. For example, machine learning models can perform binary classification, multi-class or multi-label classification. In embodiments, the machine-learning model may output "confidence scores" that are indicative of a respective confidence associated with the classification of the input into the respective class. In embodiments, the confidence scores can be compared to one or more thresholds to render a discrete categorical prediction. In embodiments, only a certain number of classes (e.g., one) with the relatively largest confidence scores can be selected to render a discrete categorical prediction. In an example, the intelligent dosing platform 100 may use such classification modeling to characterize classes of medications for use in intelligent injection devices, classify intelligent injection devices, classify patients and/or healthcare providers, classify healthcare facilities in which an intelligent injection device might be used, and the like.

In embodiments, machine learning models may output a probabilistic classification. For example, machine learning models may predict, given a sample input, a probability distribution over a set of classes. Thus, rather than outputting only the most likely class to which the sample input should belong, machine learning models can output, for each class, a probability that the sample input belongs to such class. In embodiments, the probability distribution over all possible classes can sum to one. In embodiments, a SoftMax function, or other types of function or layer can be used to turn a set of real values respectively associated with the possible classes into a set of real values in the range (0, 1) that sum to one. In embodiments, the probabilities provided by the probability distribution can be compared to one or more thresholds to render a discrete categorical prediction. In embodiments, only a certain number of classes (e.g., one) with the relatively largest predicted probability can be selected to render a discrete categorical prediction. In an example, the intelligent dosing platform 100 may utilize probabilistic classification where data inputs to the platform 100 are incomplete or otherwise missing beneficial data, as in a case where a provider is interacting with the platform 100 to begin an injection event and misspells the name of the medication to be administered. Continuing the example, the platform may use probabilistic classification to infer that the provider input of "Humira" as the medication to be administered is probabilistically "Humira" and begin a governance protocol in which the provider is required to submit additional information related to the planned medication to be administered in order for the authentication process to begin for permitting the Humira dosage to be administered. The platform 100 may further use rules related to safety to lock the intelligent injection device that the provider plans to use if the provider is unable or does not supply the additional information related to the planned medication to be administered. If the intelligent injection device is locked for such reasons, or other reasons, related to a rules breach, the platform 100 may issue an alert to notify the provider and other entities and third parties associated with the platform 100, as described herein. Upon conclusion of the platform 100 session resulting in a locked intelligent injection device, and the failure of the provider to successfully administer the medication to a patient, the patient's EMR or some other record keeping associated with the patient, the patient's provider, the patient's healthcare facility or other entity may be updated to record the missed dosage administration. The systems of payors', reimbursors' (e.g., insurance companies) and the like may also be informed and updated to record that a dose was not administered and should therefore not be billed, paid for, resent, or some other action.

In embodiments, machine learning models can perform regression to provide output data in the form of a continuous numeric value. As examples, machine learning models can perform linear regression, polynomial regression, or nonlinear regression. As described, in embodiments, a SoftMax function or other function or layer can be used to squash a set of real values respectively associated with two or more possible classes to a set of real values in the range (0, 1) that sum to one. For example, machine learning models can perform linear regression, polynomial regression, or nonlinear regression. As examples, machine learning models can perform simple regression or multiple regression. As described above, in some implementations, a SoftMax function or other function or layer can be used to squash a set of real values respectively associated with two or more possible classes to a set of real values in the range (0, 1) that sum to one.

In embodiments, machine learning models may perform various types of clustering. For example, machine learning models may identify one or more previously-defined clusters to which the input data most likely corresponds. In some implementations in which machine learning models perform clustering, machine learning models can be trained using unsupervised learning techniques.

In embodiments, machine learning models may perform anomaly detection or outlier detection. For example, machine learning models can identify input data that does not conform to an expected pattern or other characteristics (e.g., as previously observed from previous input data). As examples, the anomaly detection can be used for fraud detection or system failure detection, such as an intelligent injection device sending a signal to the platform 100 to verify and authenticate its manufacturing provenance and validate its chain of custody up to and including the point of a provider requesting to administer a medication using the intelligent injection device.

In some implementations, machine learning models can provide output data in the form of one or more recommendations. For example, machine learning models can be included in a recommendation system or engine. As examples, given input data that describes previous outcomes for certain entities (e.g., a score, ranking, or rating indicative of an amount of success or enjoyment), machine learning models can output a suggestion or recommendation of one or more additional entities that, based on the previous outcomes, are expected to have a desired outcome.

As described above, machine learning models can be or include one or more of various different types of machine-learned models. Examples of such different types of machine-learned models are provided below for illustration. One or more of the example models described below can be used (e.g., combined) to provide the output data in response to the input data. Additional models beyond the example models provided below can be used as well.

In some implementations, machine learning models can be or include one or more classifier models such as, for example, linear classification models; quadratic classification models; etc. Machine learning models may be or include one or more regression models such as, for example, simple linear regression models, multiple linear regression models, logistic regression models, stepwise regression models, multivariate adaptive regression splines, locally estimated scatterplot smoothing models, and the like.

In some examples, machine learning models can be or include one or more decision tree-based models such as, for example, classification and/or regression trees, chi-squared automatic interaction detection decision trees, decision stumps, conditional decision trees, and the like.

Machine learning models may be or include one or more kernel machines. In some implementations, machine learning models can be or include one or more support vector machines. Machine learning models may be or include one or more instance-based learning models such as, for example, learning vector quantization models, self-organizing map models, locally weighted learning models, and the like. In some implementations, machine learning models can be or include one or more nearest neighbor models such as, for example, k-nearest neighbor classifications models, k-nearest neighbors regression models, and the like. Machine learning models can be or include one or more Bayesian models such as, for example, naïve Bayes models, Gaussian naïve Bayes models, multinomial naïve Bayes models, averaged one-dependence estimators, Bayesian networks, Bayesian belief networks, hidden Markov models, and the like.

Machine learning models may include one or more clustering models such as, for example, k-means clustering models, k-medians clustering models, expectation maximization models, hierarchical clustering models, and the like.

In some implementations, machine learning models can perform one or more dimensionality reduction techniques such as, for example, principal component analysis, kernel principal component analysis, graph-based kernel principal component analysis, principal component regression, partial least squares regression, Sammon mapping, multidimensional scaling, projection pursuit, linear discriminant analysis, mixture discriminant analysis, quadratic discriminant analysis, generalized discriminant analysis flexible discriminant analysis, autoencoding, and the like.

In some implementations, machine learning models can perform or be subjected to one or more reinforcement learning techniques such as Markov decision processes, dynamic programming, Q functions or Q-learning, value function approaches, deep Q-networks, differentiable neural computers, asynchronous advantage actor-critics, deterministic policy gradient, and the like.

In some embodiments, the intelligence analytics module 134 of the intelligent dosing platform 100 may determine one or more analyses that are to be performed with respect to a particular decision and may provide corresponding analysis modules that perform those analyses to the artificial intelligence modules 104, such that the artificial intelligence modules 104 leverage the corresponding intelligence analytics modules 134 to analyze a decision before outputting the decision to the requesting client.

Figure 3:
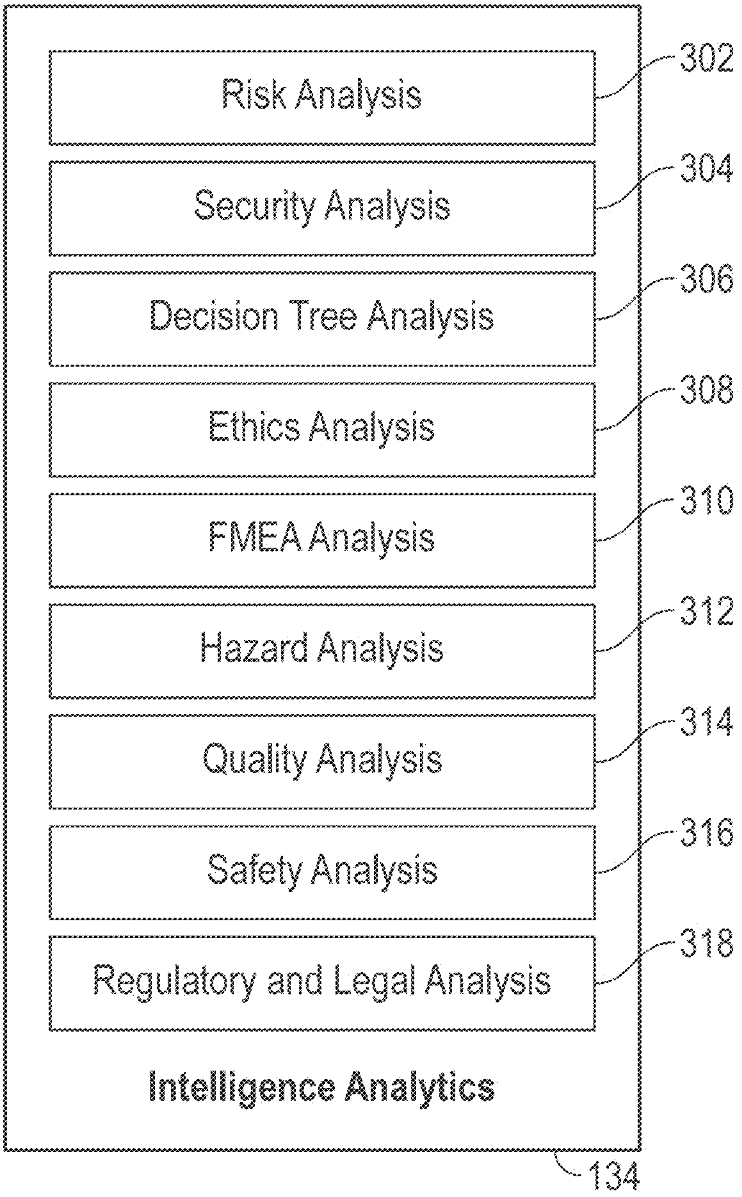
FIG. 3 is a diagram illustrating intelligence analytics of an intelligent dosing platform.

Referring to FIG. 3, in embodiments, the intelligence analytics module 134 may include a plurality of analysis modules 302-318 that are configured to perform specific analyses with respect to certain types of decisions, whereby the respective modules are executed by a processing system that hosts the instance of the intelligence functions 202. Non-limiting examples of analysis modules may include risk analysis module(s) 302, security analysis module(s) 304, decision tree analysis module(s) 306, ethics analysis module(s) 308, failure mode and effects (FMEA) analysis module(s) 310, hazard analysis module(s) 312, quality analysis module(s) 314, safety analysis module(s) 316, regulatory and legal analysis module(s) 318, and/or other suitable analysis modules. It is appreciated that the foregoing are non-limiting examples of intelligence analytics modules 134, and that some of the modules may be included or leveraged by other intelligent dosing platform modules.

In some embodiments, the intelligence analytics module 134 may be configured to determine which types of analyses to perform based on the type of decision that was requested by an intelligence service client. For example, the platform 100 may use a patient's historical intelligent injection device use data to predict the injectable product needs for the patient during a given timeframe, for a specific health condition, to be covered by a particular insurer, to be delivered in a specific packaging or environmental context, and the like. In an embodiment, different geographic regions to which intelligent injection devices/medications are to be sent may be experiencing different climate or environmental factors (i.e., have different packaging needs). Thus, the intelligence analytics module 134 may restrict and/or request particular data and analyses to fit a given geographic region. In some of these embodiments, the intelligence analytics module 134 may include an index or other suitable mechanism that identifies a set of analysis modules 202-218 based on a requested decision type. In these embodiments, the intelligence analytics module 134 may receive the decision type and may determine a set of analysis modules that are to be executed based on the decision type. Additionally, or alternatively, one or more governance standards may define when a particular analysis is to be performed. For example, the engineering standards may define what scenarios necessitate a FMEA analysis by the FMEA analysis module 210. In this example, the engineering standards may have been implicated by a request for a particular type of decision and the engineering standards may define scenarios when a FMEA analysis is to be performed. In this example, artificial intelligence modules 104 may execute a safety analysis module 316 and/or a risk analysis module 302 and may determine an alternative decision if the action would violate a legal standard or a safety standard. In response to analyzing a proposed decision, artificial intelligence modules 104 may selectively output the proposed condition based on the results of the executed analyses. If a decision is allowed, artificial intelligence modules 104 may output the decision to the requesting intelligence service client 204. If the proposed configuration is flagged by one or more of the analyses, artificial intelligence modules 104 may determine an alternative decision and execute the analyses with respect to the alternate proposed decision until a conforming decision is obtained.

In various implementations, the artificial intelligence module 104 may include methods and systems for data and analytic optimization, prediction, decision support, simulation, machine learning, process automation, inference modeling, neural network modeling, digital twins modeling, and the like (collectively referred to herein as "intelligence functions 202," "artificial intelligence modules 104").

The artificial intelligence module 104 may enable the analysis module 106 to solve optimization problems according to bracketing algorithms (such as the Fibonacci search, golden-section search, and bisection method algorithms), local descent algorithms (such as the line search algorithm), and/or first order algorithms (such as the gradient descent, momentum, AdaGrad, RMSProp, and Adam algorithms). The artificial intelligence 104 may enable the analysis module to make predictions using classification models, clustering models, forecast models, outliers models, time series models, logistic regression, random forest models, generalized linear models, gradient boosted models, K-means algorithms, and/or Prophet algorithms.

The artificial intelligence module 104 may enable and run decision support systems (DSSs), which may be used to manage large volumes of data. In various implementations, DSSs may perform simulations of decision-making procedures taken by the components of the intelligent dosing platform 100 to determine optimal courses of action, gather and analyze data, and inform overall decision making as to the course of action for the components of the intelligent dosing platform 100. Simulation may be used by the machine learning (ML), artificial intelligence (AI), data processing, fusion, and integration module to generate synthetic input vectors for training machine learning models (for example, as in generative adversarial networks).

The artificial intelligence module 104 may enable and run linear regression models, logistic regression modules, decision true models, support vector machine algorithms, Naïve Bayes algorithms, K-nearest neighbor algorithms, random forest algorithms, dimensionality reduction algorithms, gradient boosting algorithms, and/or AdaBoost algorithms. The machine learning (ML), artificial intelligence (AI), data processing, fusion, and integration module may include process automation for automating any of the processes performed by components of the intelligent dosing platform 100. The machine learning (ML), artificial intelligence (AI), data processing, fusion, and integration module may use a trained machine learning model to infer a result using real-world data as inputs, such as data relating to a specific intelligent injection device, a specific medication to be used in an injectable, and the like.

The artificial intelligence module 104 may enable and run convolutional neural networks, long short-term memory (LSTM) networks, recurrent neural networks, generative adversarial networks, radial basis function networks, multilayer perceptrons, self-organizing maps, deep belief networks, restricted Boltzmann machines, and autoencoders. The machine learning (ML), artificial intelligence (AI), data processing, fusion, and integration module may generate digital twins to create virtual representations of components of the intelligent dosing platform 100 that serve as the real-time digital counterparts of the real components. Simulations may be performed on the digital counterparts to allow users to understand how the system is performing in the present, as well as to allow users to understand how the system will perform under hypothetical conditions or in the future.

In embodiments, the artificial intelligence modules 104 may include and/or provide access to an intelligence analytics module 134. In embodiments, an intelligence analytics module 134 may be configured to perform various analytical processes on data output from a plurality of entities or other data sources. In example embodiments, analytics produced by the intelligence analytics module 134 may facilitate the quantification of system performance as compared to a set of goals and/or metrics. The goals and/or metrics may be preconfigured, determined dynamically from operating results, and the like. Examples of analytics processes that can be performed by an intelligence analytics module 134 are discussed herein. In some example implementations, analytics processes may include tracking, for example, specific metrics that involve coordination of injectable medical device activities and demand intelligence, such as involving forecasting injectable medical device product demand for a set of relevant items by location and time (among many others).

In embodiments, the artificial intelligence module may include and/or provide access to a digital twin module 212. The digital twin module 212 may encompass any of a wide range of features and capabilities as described herein, such as a digital twin of an intelligent injection device with which to simulate the administration of particular medication types, appropriate environmental temperature and/or other climate/environmental, and injectable medical device practice factors. In embodiments, a digital twin module 212 may be configured to provide, among other things, execution environments for and different types of digital twins, such as twins of physical environments, twins of robot operating units, logistics twins, executive digital twins, organizational digital twins, role-based digital twins, and the like. In embodiments, the digital twin module 212 may be configured in accordance with digital twin systems and/or modules described elsewhere throughout the disclosure. In example embodiments, a digital twin module 212 may be configured to generate digital twins that are requested by intelligence clients. Further, the digital twin module 212 may be configured with interfaces, such as APIs, and the like for receiving information from external data sources. For instance, the digital twin module 212 may receive real-time data from sensor systems from various intelligent injection devices, medical equipment, vehicles, robots, or other devices, and/or sensor systems of the physical environment in which a device operates. In embodiments, the digital twin module 212 may receive digital twin data from other suitable data sources, such as third-party services (e.g., weather services, data services, logistics systems and databases, and the like). In embodiments, the digital twin module 212 may include digital twin data representing features, states, or the like of specific intelligent injection devices, containing specific medications, or the like. The digital twin module 212 may be integrated with or into, link to, or otherwise interact with an interface (e.g., a dashboard), for coordination of supply of injectable medical device products and/or intelligent injection device management activities. In embodiments, a digital twin module may provide access to and manage a library of digital twins. Artificial intelligence modules 104 may access the library to perform functions, such as a simulation of actions in a given environment in response to certain stimuli.

In various implementations, the artificial intelligence module may include libraries, one or more data stores, data services, and bridging and integration services. In various implementations, the libraries may be a collection of non-volatile resources used by modules and applications of the analysis module. In various implementations, the data stores may be shared volatile or non-volatile computer readable storage media on which the components of the intelligent dosing platform 100 may be stored or may use.

In various implementations, data services may include data processing, data handling, data analysis, data enrichment, and data aggregation. Data processing may include processing data from entities external to the intelligent dosing platform 100 or from various components of the intelligent dosing platform 100. Data handling may include data received from entities external to the platform 100 or from various components of the intelligent dosing platform 100. Data analysis may include analysis on data received from entities external to the systems of platform 100 or from various components of the intelligent dosing platform 100. Data aggregation may aggregate data received from entities external to the systems of platform 100 or from various components of the intelligent dosing platform 100.

In embodiments, the artificial intelligence module 104 may include and/or provide access to a machine vision module 214. In embodiments, the machine vision module 214 may be configured to process images (e.g., captured by a camera) to, for example, detect and classify objects in the image. In embodiments, the machine vision module 214 may receive one or more images (which may be frames of a video feed or single still shot images) and identifies diffuse areas in an image (e.g., using edge detection techniques or the like). The machine vision module 214 may then classify the diffuse areas. In some embodiments, the machine vision module 214 leverages one or more machine-learned image classification models and/or neural networks (e.g., convolutional neural networks) to classify the diffuse areas in the image. In some embodiments, the machine vision module 214 may perform feature extraction on the images and/or the respective areas in the image prior to classification. In some embodiments, the machine vision module 214 may leverage classification made in a previous image to affirm or update classification(s) from the previous image. For example, if an object that was detected in a previous frame was classified with a lower confidence score (e.g., the object was partially occluded or out of focus), the machine vision module 214 may affirm or update the classification if the machine vision module 214 is able to determine a classification of the object with a higher degree of confidence. In embodiments, the machine vision module 214 is configured to detect occlusions, such as objects that may be occluded by another object. In embodiments, the machine vision module 214 receives additional input to assist in image classification tasks, such as from a radar, a sonar, a digital twin of an environment (which may show locations of known objects), and/or the like.

In embodiments, the artificial intelligence module may include and/or provide access to a natural language processing (NLP) module 216. In embodiments, an NLP module 216 may perform natural language tasks on behalf of an intelligence service client. Examples of natural language processing techniques may include, but are not limited to, speech recognition, speech segmentation, creation of speaker diaries, text-to-speech, lemmatization, morphological segmentation, parts-of-speech tagging, stemming, syntactic analysis, lexical analysis, and the like. In embodiments, the NLP module 216 may enable voice commands that are received from a human. For example, a healthcare provider may interact with the platform 100, in part, by issuing an analytic request by a voice command (e.g., "Please confirm the recommended dose for Medication X for Patient Y on Date Z" and/or "What is the appropriate location on the body to inject Medication X for Patient Y?") In embodiments, the NLP module 216 may receive an audio stream (e.g., from a microphone) and may perform voice-to-text conversion on the audio stream to obtain a transcription of the audio stream. The NLP module 216 may process text (e.g., a transcription of the audio stream) to determine a meaning of the text using various NLP techniques (e.g., NLP models, neural networks, and/or the like). In embodiments, the NLP module 216 may determine an action or command that was spoken in the audio stream based on the results of the NLP. In embodiments, the NLP module 216 may output the results of the NLP to an intelligence service client. Text and other outputs from the intelligent dosing platform and the NLP module may be used as inputs to a generative-AI module, LLM, or other artificial intelligence module, as described herein.

In embodiments, the NLP module 216 may provide an intelligence service client with the ability to parse one or more conversational voice instructions provided by a human user to perform one or more tasks as well as communicate with the human user. The NLP module 216 may perform speech recognition to recognize the voice instructions, natural language understanding to parse and derive meaning from the instructions, and natural language generation to generate a voice response for the user upon processing of the user instructions. In some embodiments, the NLP module 216 enables an intelligence service client 204 to understand the instructions and, upon successful completion of the task by the intelligence service client 204, provide a response to the user. In embodiments, the NLP module 216 may formulate and ask questions to a user if the context of the user request is not completely clear. In embodiments, the NLP module 216 may utilize inputs received from one or more sensors, such as data from vision sensors, location-based data (e.g., GPS data), and the like, to determine context information associated with processed speech or text data.

In embodiments, the NLP module 216 may use neural networks when performing NLP tasks, such as recurrent neural networks, long short-term memory (LSTMs), gated recurrent unit (GRUs), transformer neural networks, convolutional neural networks, and/or the like.

In embodiments, the analysis module 106 may provide data handling, analytics, prediction and recommendation methods and systems, as described herein relating to injectable medical device practices, government and other programs relating to injectable medical device practices, financial and economic factors relating to injectable medical device practices, and the like. In embodiments, the finance/insurance/policy analysis module may provide data handling, analytics, prediction and recommendation methods and systems, as described herein relating to injectable medical device finance, injectable medical device product finance and procurement, and the like. In embodiments, the analysis module may provide data handling, analytics, prediction and recommendation methods and systems, as described herein relating to intelligent injection device performance, predicted injectable medical device outcomes, product selection, the timing of intelligent injection device activities, the selection and application of injectable medical device products and services, and the like. In embodiments, the finance/insurance/policy analysis module may provide data handling, analytics, prediction and recommendation methods and systems, as described herein relating to injectable medical device insurance, injectable medical device product and equipment insurance, medical insurance, and the like. In embodiments, the finance/insurance/policy analysis module may provide data handling, analytics, prediction and recommendation methods and systems, as described herein relating to injectable medical device policies (e.g., federal, state, county) impacting medical practices, finance, regulatory compliance, product and equipment pricing, and the like.

The analysis module 106 may analyze components of the platform 100 (and interactions between components) for compliance with various federal and state laws, regulations, and rules governing financial institutions. This may include ethics analysis for analyzing ethical rules governing administration of intelligent injection devices. The analysis module 106 may analyze blockchains and markets and exchanges based on pricing metrics, news, and performance data (such as technical data). In various implementations, the analysis module may perform technical analysis on markets and exchanges by analyzing price movements and trading volumes over specific periods of time to calculate metrics such as relative strength and/or moving averages, and/or performs regressions on pricing data to determine relationships between variables. In various implementations, the analysis module may use mathematical indicators to evaluate statistical trends to predict price direction in the injectable medical device, and related markets, such as by analyzing past price changes and volume data to predict future price changes. The analysis module may analyze components of the intelligent dosing platform 100 (and interactions between components) for legal compliance with various federal and state laws, regulations, and rules governing intelligent injection devices.

In various implementations, a governance library, used by the governance module 110, may include a training model standards library, a legal standards library, a regulatory standards library, and a custom standards library. The training model standards library may contain data governing the training of each of the various machine learning models of the analysis module. The legal standards library may contain rules related to federal and state laws that are suitable for use by the analysis module. The regulatory standards library may contain rules related to federal and state regulations and rules that are suitable for use by the analysis module. The custom standards library may contain custom rules set by users that are suitable for use by the analysis module.

In embodiments, the artificial intelligence module 104 may include and/or provide access to a rules-based module 208 that may be integrated into or be accessed by an intelligence service client 204. In some embodiments, a rules-based module 208 may be configured with programmatic logic that defines a set of rules and other conditions that trigger certain actions that may be performed in connection with an intelligence client. In embodiments, the rules-based module 208 may be configured with programmatic logic that receives input and determines whether one or more rules are met based on the input. If a condition is met, the rules-based module 208 determines an action to perform, which may be output to a requesting intelligence service client 204. The data received by the rules-based engine may be received from an intelligence service input source and/or may be requested from another module in an artificial intelligence module. For example, a rule-based module may receive classifications of intelligent injection device types, medication types, patient types, clinic types, including veterinary clinics, or some other classification. In embodiments, the rules-based module may be configured to make other suitable rules-based decisions on behalf of a respective user. In some embodiments, the rules-based engine may apply governance standards and/or analytics.

In embodiments, intelligence functions 202 of the intelligent dosing platform 100 may be configured to determine a type of request issued by an intelligence service client 204 and, in response, may determine a set of governance standards and/or analyses that are to be applied by the artificial intelligence modules 104 when responding to the request. In embodiments, the intelligence functions 202 may include an analysis management module, a set of analysis modules, and a governance library. In embodiments, the intelligence analytics module 134 may receive an artificial intelligence module 104 request and determines the governance standards and/or analyses implicated by the request. In embodiments, the intelligence analytics module 134 may determine the governance standards that apply to the request based on the type of decision that was requested and/or whether certain analyses are to be performed with respect to the requested decision. For example, a request for a control decision that results in an intelligence service client 204 performing an action may implicate a certain set of governance standards that apply, such as safety standards, legal standards, regulatory standards, quality standards, or the like, and/or may implicate one or more analyses regarding a control decision, such as regarding the use of an intelligent injection device, or the like.

In some embodiments, the governance module 110 may determine the governance standards that apply to a decision request based on one or more conditions. Non-limiting examples of such conditions may include the type of decision that is requested, a location in which a decision is being made, an environment that the decision will affect (e.g., a clinic or hospital setting), current or predicted environment conditions of the environment (e.g., weather data impacting injectable medicine storage, shipping, and the like) and/or the like. In embodiments, the governance standards may be defined as a set of standards libraries stored in a governance library. In embodiments, standards libraries may define conditions, thresholds, rules, recommendations, or other suitable parameters by which a decision may be analyzed. Examples of standards libraries may include, legal standards library, a regulatory standards library, a quality standards library, an engineering standards library, a safety standards library, a financial standards library, and/or other suitable types of standards libraries. In embodiments, the governance library may include an index that indexes certain standards defined in the respective standards library based on different characteristics. Examples of characteristics may be a jurisdiction or geographic areas to which certain standards apply, environmental conditions to which certain standards apply, intelligent injection device types to which certain standards apply, materials or products to which certain standards apply, and/or the like.

In some embodiments, the governance module 110 may determine the appropriate set of standards that must be applied with respect to a particular decision and may provide the appropriate set of standards to the artificial intelligence modules 104 such that the artificial intelligence modules 104 leverage the implicated governance standards when determining a decision. In these embodiments, the artificial intelligence modules 104 may be configured to apply the standards in the decision-making process, such that a decision output by the artificial intelligence modules 104 is consistent with the implicated governance standards. It is appreciated that the standards libraries in the governance library may be defined by the platform provider, customers, and/or third parties. The standards may be government standards, industry standards, customer standards, or other suitable sources. In embodiments, each set of standards may include a set of conditions that implicate the respective set of standards, such that the conditions may be used to determine which standards to apply given a situation.

In various implementations, the stakeholder-specific intelligence functions 122 module may include demand forecasting module, a financial forecasting module, a waste tracking module, and a safety monitoring module. These modules may perform forecasting and prediction, demand intelligence, and utilize a recommendation engine as part of, for example, automated planning. Other actions performed by the stakeholder-specific intelligence functions 122 module may include but are not limited to outcome analysis and transaction analysis. In embodiments, forecasting and prediction may provide data handling, analytics, prediction and recommendation methods and systems, as described herein relating to injectable medical device practices, decision making, procurement and other injectable medical device activities. In embodiments, demand intelligence may provide data handling, analytics, prediction and recommendation methods and systems, as described herein relating to economic and market factors impacting injectable medical device practices, decision making, procurement and other injectable medical device activities, including but not limited to market demand, market preference, market forecasting, and the like. In embodiments, recommendations processes may provide data handling, analytics, prediction and recommendation methods and systems, as described herein relating to injectable medical device practices, decision making, procurement and other injectable medical device activities, such as the need for injectable product resupply and the like. In embodiments, automated planning by the platform 100 may provide data handling, analytics, prediction and recommendation methods and systems, as described herein relating to the automated generation of injectable medical device plans, such as the timing of the delivery of injectable medical device products to a clinic or hospital, or other recommendation generated by the platform 100. Outcome analysis may provide data handling, analytics, prediction and recommendation methods and systems, as described herein relating to injectable medical device practices, products, and the like.

In embodiments, the transaction/stakeholders module 116 may be associated with the intelligent dosing platform 100 and may classify transactions performed by the components of the intelligent dosing platform 100 (and transactions between components), classifying each transaction into one or more categories. The transaction/stakeholders module 116 may monitor transactions between the components of the intelligent dosing platform 100 for each transaction or group of transactions, such as purchases of intelligent injection devices, or for each user or group of users. In various implementations, the transaction/stakeholders module 116 may monitor transactions within each transaction or group of transactions (or for each user or group of users) to determine whether the monitored transaction fits a generated profile. In various implementations, if the monitored transaction does not fit a generated profile, the transaction/stakeholders may generate an alert and/or halt the monitored transaction from participating in a would-be transaction aggregation.

In embodiments, the care/providers module 118 may be associated with the intelligent dosing platform 100 and may provide, share, transfer or otherwise communicate data, services and analytics with the platform 100 from entities including but not limited to patient data, services and analytics (e.g., EMR), healthcare provider data, services and analytics, practice group data, services and analytics, hospital data, services and analytics, outpatient clinic data, services and analytics, EMT data, services and analytics, home health/hospice data, services and analytics, pharmacy data, services and analytics, veterinary data, services and analytics, or some other type of data, service and/or analytics.

In embodiments, the devices/procedures module 120 may be associated with the intelligent dosing platform 100 and may provide, share, transfer or otherwise communicate data, services and analytics with the platform 100 including data, services and analytics related to intelligent injection devices and/or procedures, including but limited to, smart syringes (including but limited to syringes used for subcutaneous, intramuscular, intravenous, intraosseous, intradermal, or some other syringe injection application type), IVs, auto-devices (e.g., insulin pumps), joint aspiration, venipuncture, intubation, thrombolytics, some other type of intelligent injection device and/or procedure.

In various implementations, the reporting and stakeholder-specific reporting modules 130 may include reporting data and analytics related to custody tracking of intelligent injection devices and related material, adherence tracking, tracking of patient outcomes, regulatory reporting, inventory/supply chain, and reporting data and analytics related to price management, formulary management, distribution management, compliance, or some other reporting and/or data and analytics output type.

In embodiments, the stakeholder-specific intelligence functions 122 may include portals and distributed apps, blockchain services, smart contract services, payment automation services, and distributed ledger services bridging components of the analysis module with external portals, decentralized apps, and the like. Blockchain services may bridge components of the analysis module with external blockchain services. Smart contract services may bridge components of the analysis module with external smart contract applications. Payment automation services may bridge components of the analysis module with external payment automation applications. Distributed ledger services may bridge components of the analysis module with external payment automation applications.

In embodiments, the analysis module 106 may communicate with the stakeholder-specific intelligence functions 122 based at least in part by using the stakeholder systems integration module. The stakeholder systems integration module may be further associated with a results-based analysis and feedback optimization module. In embodiments, the stakeholder systems integration module may include a system integration services, a user interface (UI), applications library, application programming interface (API), data visualization services, a software development kit. The stakeholder systems integration module may perform system integration functions between components of the analysis module and external devices. The user interface may generate and output user interfaces accessible by components of the intelligent dosing platform 100. The applications library may contain applications that may be accessed by the external systems through the API. The applications may interface with other components of the analysis module and/or the other components of the intelligent dosing platform 100. The API may facilitate communications between the applications and modules of the analysis module and the external systems, such as the various components of the intelligent dosing platform 100. The SDK may contain a collection of software development tools suitable for creating and modifying applications, such as those of the applications library.

In embodiments, provided herein is an intelligent injection device 400 comprising: a barrel 402 in fluid communication with a needle 404 connected with a first end of the barrel 402; a piston 406 comprising a plunger 408, the piston 406 positioned within a second end of the barrel 402 and the plunger 408 having a fluid-tight interaction with an interior of the barrel 402; and a microprocessor 510 in electronic communication with a switch 506 and a wireless module 504, the microprocessor 510 configured to send administration data from the wireless module 504 after triggering the switch 506. The microprocessor 510 is configured to send administration data via the wireless module 504 after the switch 506 is triggered. For example, in a diabetes management scenario, the device can automatically record the time and dosage of insulin administered, transmitting the data to a healthcare record of the patient. The microprocessor 510 facilitates real-time data transmission upon activation, which is beneficial for chronic conditions like diabetes where timely data logging is beneficial for dose adjustment. For instance, in remote areas, the intelligent injection device 400 ensures continuous patient monitoring, enabling healthcare providers to adjust treatment plans based on real-time data.

In embodiments, the intelligent injection device 400 includes a temperature sensor 502 and a locking mechanism 512 engaged with a stalk 410 of the piston 406 to prevent injection based on a temperature sensed by the temperature sensor 502. The locking mechanism 512 engages with the stalk 410 of the piston 406 to prevent injection if the sensed temperature is outside the safe range. The temperature sensor 502 and a locking mechanism 512 is useful in the delivery of temperature-sensitive biologics, thereby ensuring that medications like vaccines are administered at their optimal efficacy levels. The temperature sensor 502 and a locking mechanism 512 prevent the administration of medication that has been exposed to temperatures that can affect its potency. For example, in vaccine distribution during humanitarian missions, maintaining a cold chain is critical, and the device ensures that only vaccines kept at the correct temperature are administered.

In embodiments, the intelligent injection device 400 includes a microprocessor 510 in electronic communication with a load sensor 1200 for detecting a force measurement upon an injectable fluid contained within the device upon depression of the plunger 408 to eject the fluid from the device. The load sensor 1200 detects force measurements on the injectable fluid when the plunger 408 is depressed. This can be beneficial in settings where precise dosing is necessary, such as administering pediatric vaccinations, thereby ensuring that each dose is delivered accurately. Accurate force measurement ensures that delicate medications, such as those used in pediatric oncology, are administered precisely, minimizing the risk of overdose or underdose, which can be critical to treatment outcomes.

In embodiments, the intelligent injection device 400 includes a microprocessor 510 in electronic communication with a system for detecting a depth measurement of a penetration of a needle 404 of the device. The system for detecting the depth of needle 404 penetration, controlled by the microprocessor 510. This is useful in procedures like epidural injections where the depth of needle 404 insertion must be carefully controlled to avoid complications. In procedures requiring precise depth control, such as lumbar punctures, the system ensures that the needle 404 reaches the correct depth without causing injury or discomfort, improving patient safety and procedural success rates.

In embodiments, the intelligent injection device 400 includes a microprocessor 510 in electronic communication with a system for detecting an angle measurement of a needle 404 of the device relative to a surface of injection. The device can measure the angle of the needle 404 relative to the injection surface, which is vital for procedures like angiography where the angle of entry can affect the success of the procedure. Ensuring the correct angle of the needle 404 can be beneficial in procedures like sclerotherapy for treating varicose veins, where the angle of injection can affect the efficacy of the treatment and the comfort of the patient.

In embodiments, the intelligent injection device 400 includes a microprocessor 510 in electronic communication with a system for detecting the amount of an injectable that is delivered to a recipient of an injection. The device is capable of detecting the amount of injectable delivered, which is beneficial in treatments requiring high precision in dosage, such as chemotherapy, where slight variations can significantly impact treatment efficacy and patient safety. The microprocessor 510 is useful in the administration of drugs with narrow therapeutic windows, where slight variations in dosage can lead to significant complications.

In embodiments, the intelligent injection device 400 includes a microprocessor 510 in electronic communication with a damage detection system for detecting damage to the device. The damage detection system can identify any physical defects or malfunctions in the device, which is beneficial in emergency settings where equipment reliability can directly impact patient outcomes. In emergency scenarios, such as field hospitals in disaster zones, thereby ensuring that all equipment is functional and undamaged is critical. The system allows for quick checks, thereby ensuring that devices are safe to use.

In embodiments, the intelligent injection device 400 includes a microprocessor 510 in electronic communication with an automatic injection system for automatically delivering a dose from the injection device 400. The automatic injection system delivers doses without manual intervention, ideal for patients with conditions like rheumatoid arthritis who may struggle with manual dexterity. For patients with severe arthritis or other conditions that impair manual dexterity, the system allows for independent medication administration, enhancing their quality of life and treatment adherence.

In embodiments, the intelligent injection device 400 includes a microprocessor 510 in electronic communication with a timestamping system for timestamping injection events. The timestamping system records the exact time of injections, which can be used in clinical trials to ensure that the timing of dosing is accurately reported and adhered to. In clinical trials, precise timestamping ensures the integrity of the study by providing accurate data on when medications were administered, which is beneficial for the validity of the study.

In embodiments, provided herein is an intelligent dosing platform 100 for real-time monitoring and management of adherence to a program for administration of a set of injectables. The platform 100 provides real-time monitoring and management of adherence to a program involving multiple injectables, which can be beneficial in complex medication regimens like those for treating HIV/AIDS, thereby ensuring that patients adhere to their prescribed treatment schedules. Managing multiple injectables, such as in HIV treatment regimens, requires precise scheduling and adherence. The platform 100 helps patients keep track of multiple medications, reducing the risk of missed doses.

In embodiments, the platform 100 receives data collected from an intelligent injection device 400. The platform 100 can receive and process data from intelligent injection device 100XXs, enabling healthcare providers to monitor compliance remotely, useful in home healthcare scenarios to ensure that elderly patients are correctly following their medication schedules. In home healthcare settings, data from injection device 100XXs can be automatically sent to healthcare providers, allowing for remote monitoring and timely interventions if a patient misses a dose or if there are signs of complications.

In embodiments, the platform 100 receives data collected by an Internet of Things (IoT) device. Integration with IoT devices allows for the collection of additional contextual data, such as environmental factors, which can influence medication effectiveness, which is beneficial in managing asthma where environmental triggers play a significant role. Integrating environmental sensors can help manage asthma by adjusting medication based on air quality readings, providing personalized care that can prevent asthma attacks.

In embodiments, the platform 100 receives data collected by a wearable device. Data from wearable devices can be used to adjust medication plans based on real-time health status updates, which is beneficial for heart failure patients where fluid status may frequently change. For heart failure patients, wearable devices can monitor fluid status and adjust diuretic dosages accordingly, thereby preventing hospital readmissions due to fluid overload.

In embodiments, the platform 100 is integrated with an emergency medical record system and/or an emergency health record system. The platform 100 integrates with emergency medical and health record systems, allowing for immediate updates to patient records during critical situations, such as updating allergy information during an anaphylactic emergency. During anaphylactic reactions, immediate updates to medical records of a patient with treatment details can be beneficial for subsequent care, thereby ensuring all healthcare providers are informed of the condition and treatment of the patient.

In embodiments, the platform 100 includes an intelligent virtual care assistant configured to perform tasks or services for a user. The intelligent virtual care assistant can perform tasks such as scheduling medication reminders or providing health tips, enhancing patient engagement and adherence in chronic disease management. The assistant can help manage chronic diseases by reminding patients to take their medications and providing tips on lifestyle adjustments that can improve their condition, such as dietary suggestions for hypertension management.

In embodiments, the platform 100 includes an alerts system for providing alerts to a user. The alerts system notifies users of critical information, such as when to administer an EpiPen for severe allergic reactions, enhancing timely and appropriate responses to health crises. Alerts can notify caregivers or patients as to a time to administer critical medications, such as EpiPens, thereby ensuring timely treatment in life-threatening situations.

In embodiments, the platform 100 includes a user interface. The user interface is a user-friendly interface that allows patients to easily interact with their health data and manage their injection schedules, which is beneficial for individuals managing multiple health conditions simultaneously. The user interface allows patients to easily report side effects, view their medication schedule, and receive educational content, making it easier for them to manage their health.

In embodiments, the platform 100 includes a monitoring system for monitoring user compliance. The monitoring system tracks user compliance with their medication regimen, which is beneficial for conditions like tuberculosis where incomplete treatment can lead to drug resistance. For diseases like tuberculosis, where treatment duration is long and adherence is beneficial, the system can alert healthcare providers if a patient is falling behind, allowing for early intervention.

In embodiments, the platform 100 includes a recommendation system for generating user recommendations. The recommendation system generates personalized health suggestions, such as adjusting diet to improve treatment outcomes for diabetic patients. Based on patient data, the system can recommend lifestyle changes, such as low-sodium diets for patients with high blood pressure, which can be integrated into a treatment plan of a patient.

In embodiments, the platform 100 includes a reporting system for generating reports. The reporting system generates detailed reports on patient adherence, which can be used by healthcare providers to identify patients at risk of non-compliance and intervene accordingly. Healthcare providers can generate reports on patient adherence, which can be used during consultations to discuss progress and make adjustments to treatment plans, enhancing personalized care.

In embodiments, the platform 100 includes a mobile application. The mobile application allows patients to manage their injection schedules and view their medication history on the go, ideal for busy individuals or those frequently traveling. Patients can use the mobile app to manage their appointments, refill prescriptions, and communicate with their healthcare providers, making healthcare management more accessible and efficient.

In embodiments, the platform 100 includes a verification system for verifying users. The verification system ensures that the medication is administered by or to the correct person, critical in settings like nursing homes to prevent medication errors. In institutional settings like nursing homes, the system ensures that medications are administered to the right patient, preventing potentially dangerous medication errors.

In embodiments, the platform 100 includes a dashboard configured to provide visual information related to injection administration compliance. The dashboard provides visual information on injection administration compliance, helping patients and healthcare providers quickly assess adherence levels and make necessary adjustments. Healthcare providers can use the dashboard to quickly assess adherence levels of a patient and identify trends or issues that need attention, facilitating more informed clinical decisions.

In embodiments, the platform 100 includes a blockchain system for storing injection administration-related data. The blockchain system uses blockchain technology for storing injection-related data to ensure that records are secure and tamper-proof, which is beneficial for maintaining patient confidentiality and trust. Blockchain technology ensures that all patient data is encrypted and securely stored, preventing unauthorized access and ensuring that patient records are private and secure.

In embodiments, the platform 100 includes a decentralized ledger system for storing injection administration-related data. The decentralized ledger system enhances data integrity by providing a secure and transparent method for recording transactions, which is beneficial in clinical settings to ensure that medication administration records are accurate and unaltered. The decentralized ledger provides a transparent and immutable record of all transactions, which is beneficial for legal compliance and for maintaining trust in the healthcare system.

In embodiments, the platform 100 includes a scheduling system for scheduling user actions related to injection administration. The scheduling system helps users manage their injection times and healthcare appointments, reducing the likelihood of missed doses, and is helpful for patients with cognitive impairments. The system helps patients with cognitive impairments by reminding them of their medication schedules and upcoming appointments, thereby ensuring they receive their treatments on time.

In embodiments, the platform 100 includes a gamification system for gamifying platform features. The gamification system incentivizes compliance through rewards, making the management of chronic conditions like hypertension more engaging and less daunting. Gamification elements, such as earning points for taking medications on time, can make managing chronic conditions more engaging, especially for younger patients who may find long-term treatment regimens daunting.

In embodiments, the platform 100 includes a rewards system for providing users with rewards for compliance-related activity. The rewards system provides incentives for compliance-related activities, encouraging patients to adhere to their treatment plans, which is beneficial in pediatric care to motivate young patients to complete their treatment courses. Patients can earn rewards, such as discounts on health products, for consistently following their treatment regimen, providing an incentive for adherence.

In embodiments, the platform 100 includes a training system for providing training to users related to the use of intelligent injection device 100XXs. The training system educates users on how to properly use intelligent injection device 100XXs, thereby ensuring that devices are used safely and effectively, which is beneficial for new users or in low-resource settings. The training system includes video tutorials and interactive guides on how to use the injection device 400 properly, which is beneficial for patients new to self-administered injections.

In embodiments, the platform 100 includes a supply chain tracking system. The supply chain tracking system monitors the distribution and availability of injectable medications, thereby ensuring that there are no disruptions in patient care, which is beneficial during global health emergencies like pandemics. During global health crises, such as pandemics, the system tracks the distribution of vaccines and other medications, thereby ensuring they are delivered where needed and preventing stockouts.

In embodiments, the platform 100 includes a device/app integration system. The integration of the platform 100 with other devices and apps allows for a seamless user experience, thereby ensuring that all health-related data is centralized and easily accessible, which is beneficial for comprehensive health management. Integration with health monitoring devices, such as blood pressure cuffs, allows all health data to be centralized in the app, providing a comprehensive overview of the health of a patient.

In embodiments, the platform 100 includes a continuity of care system. The continuity of care system ensures that patient care is consistent and coordinated across different healthcare settings, which is vital for patients transitioning between care levels, such as from hospital to home care. As patients transition from hospital to home care, the system ensures that all relevant health information follows them, preventing gaps in care and ensuring that treatment continues seamlessly.

In embodiments, the platform 100 includes an informed consent system. The informed consent system provides patients with clear information about their treatment options and gathers their consent digitally, enhancing patient understanding and compliance in telemedicine. The digital informed consent feature provides patients with easy-to-understand information about their treatment options, allowing them to make informed decisions about their care.

In embodiments, the platform 100 includes a compliance/reporting/validation system. The comprehensive system for compliance monitoring, reporting, and validation ensures that all regulatory requirements are met, which is beneficial in pharmaceutical industries for maintaining licensure and avoiding legal issues. The comprehensive system tracks compliance with healthcare regulations, generates necessary reports for regulatory bodies, and validates that all procedures meet industry standards.

In embodiments, the platform 100 includes a privacy/governance system. The privacy and governance system protects patient data according to legal standards, thereby ensuring that sensitive information is handled appropriately, which is critical in regions with stringent data protection laws. The system ensures compliance with global data protection regulations, such as GDPR, through robust data governance practices that protect patient information.

In embodiments, the platform 100 includes a research platform 100/clinical trial/observational study system. The system for tracking patient outcomes and managing study data supports research and clinical trials, which is beneficial for developing new treatments and ensuring that they are safe and effective. Researchers can use the system to track patient outcomes and manage clinical trial data, facilitating the development of new treatments and ensuring they are both effective and safe.

In embodiments, the platform 100 includes a patient outcome tracking system. The patient outcome tracking system monitors the long-term effects of treatments, providing valuable data that can be used to improve future care strategies, which is useful in chronic disease management where long-term outcomes can vary widely. Long-term tracking of patient outcomes helps healthcare providers understand the effectiveness of treatments and make adjustments as necessary, improving the quality of care over time.

In embodiments, the platform 100 includes a security/blockchain/distributed ledger system. The platform 100 incorporates advanced security measures, including blockchain technology, to protect against unauthorized access and ensure data integrity, which is beneficial in maintaining patient trust and complying with health data regulations. Enhanced security features, including blockchain, protect sensitive health data and ensure that it cannot be altered or accessed without authorization, maintaining the integrity of medical records.

In embodiments, the platform 100 includes a sponsored content system. The sponsored content system allows for the integration of educational and promotional materials, which can be targeted to specific user groups, enhancing patient education and engagement, which is useful in disease awareness campaigns. The system can deliver targeted educational materials to patients based on their health conditions, helping them understand their health better and engage more actively in their treatment.

In embodiments, the intelligent injection device 400 includes a temperature excursion system. The temperature excursion system alerts users if the medication is exposed to temperatures that can degrade its effectiveness, which is beneficial for maintaining the efficacy of thermally sensitive medications like certain biologics. Alerts notify healthcare providers and patients if a medication has been exposed to inappropriate temperatures, allowing for immediate action to be taken, such as replacing the medication before it is administered.

In embodiments, the platform 100 includes a staying connected system. The staying connected system keeps patients connected with their healthcare providers, facilitating continuous communication and support, which is beneficial for mental health management where regular provider interaction can significantly impact treatment outcomes. The staying connected system facilitates ongoing communication between patients and their healthcare providers, allowing for regular updates and adjustments to treatment plans, which is especially beneficial for managing mental health conditions.

In embodiments, the platform 100 includes a digital twin system for enabling a set of digital twins that represent an intelligent injection device 400, wherein the set of digital twins arc used in a set of simulations, and wherein data from the set of simulations is used to train a set of models. The digital twin system utilizes digital twins to simulate the performance of intelligent injection device 100XXs, allowing for the optimization of device design and function before actual production, which is beneficial in reducing development costs and time-to-market for new devices. Digital twins simulate the performance of new injection device 100XXs in virtual environments, allowing manufacturers to test and refine device designs before they are built, reducing the risk of costly recalls.

In embodiments, the platform 100 includes a set of context-adaptive digital twins that digitally represent a set of parameters of a set of entities or workflows involved in the prescription, delivery, administration and reporting of medication dosage, wherein the configuration of the digital twin is automatically adapted based on contextual data relevant to the usage of the digital twin. The context-adaptive digital twins automatically adjust their configurations based on real-time data, enhancing the accuracy of simulations and predictions, which is useful in dynamic treatment environments like emergency rooms. These digital twins adjust their behavior based on real-time data, such as changes in a condition or environment of a patient, thereby ensuring that the simulations remain accurate and relevant.

In embodiments, the platform 100 includes role-based digital twins that digitally represent a set of parameters of a set of entities or workflows involved in the prescription, delivery, administration and reporting of medication dosage wherein the configuration of the digital twin is automatically adjusted based on the role of the user of the digital twin. The role-based digital twins adjust their configurations based on the role of the user, thereby providing customized information and functionality, which is beneficial in multi-disciplinary healthcare teams where different members need access to different types of data. Role-based configurations ensure that each member of a healthcare team receives information and functionality tailored to their specific needs, enhancing collaboration and efficiency.

In embodiments, the platform 100 includes a digital twin that combines data from a plurality of sensors to model at least one feature of an intelligent injection device 400 or its environment to inform a prediction or determination at least one parameter relating to one or more of its status, condition, operation, utilization or maintenance.

In embodiments, the platform 100 includes a digital twin that models at least one feature of an intelligent injection device 400 or medical dosage administration environment based on a combination of data streamed from a plurality of sensors of the intelligent injection device 400 or the medical dosage administration environment.

In embodiments, the platform 100 includes a digital twin configured to simulate at least one process of an intelligent injection device 400 environment or a medication dosage administration environment to inform determinations of at least one of process performance, device condition or patient outcome.

In embodiments, the platform 100 includes a set of digital twins that digitally represent a set of parameters of a set of entities or workflows involved in the prescription, delivery, administration and reporting of medication dosage, wherein the digital twin has an embedded AI chatbot expert trained to interact with a user to provide information about an intelligent injection device 400 or medical dosage administration. The digital twin with an embedded AI chatbot provides interactive assistance to users, offering real-time advice and support, which can enhance user confidence and adherence, which is beneficial in complex therapeutic regimens. The AI chatbot provides interactive support, answering patient questions and offering advice, which can help reduce anxiety and improve adherence to treatment regimens.

In embodiments, the platform 100 includes a set of digital twins that digitally represent a set of parameters of a set of entities or workflows involved in the prescription, delivery, administration and reporting of medication dosage, wherein the digital twin has an embedded AI system trained to interact with a user to provide information about an intelligent injection device 400 or medical dosage administration wherein the AI system configures a set of CAD-based simulations for the digital twin. The digital twin includes an AI system that configures CAD-based simulations, enhancing the precision of device modeling and performance testing, which is beneficial in the design phase of medical devices. The set of digital twins that digitally represent a set of parameters of a set of entities or workflows involved in the prescription, delivery, administration and reporting of medication dosage allows for detailed simulations of device behavior, helping engineers identify potential issues in the design phase, which can be addressed before the device is manufactured.

In embodiments, the platform 100 includes a digital twin that represents an intelligent device and/or medication dosage environment and patient physical characteristics. The digital twin models features of the medication administration environment and patient physical characteristics, which can be used to tailor treatment plans to individual patient needs, thereby enhancing personalized medicine approaches. Modeling the patient and medication environment helps personalize treatment plans, thereby ensuring that each patient receives the most effective and appropriate care for their specific situation.

In embodiments, the platform 100 includes a digital twin that represents an intelligent device and/or medication dosage environment and patient medications and historical reactions and/or outcomes.

In embodiments, the platform 100 includes a digital twin that represents an intelligent device and/or medication dosage environment and payor parameters for dosage administration. The digital twin that represent drug interaction effects and payor parameters can be used to optimize treatment cost-effectiveness and ensure compliance with insurance requirements, which is beneficial in managed care settings. The system models potential drug interactions and incorporates payor parameters to optimize the cost-effectiveness of treatments, thereby ensuring that patients receive care that is both effective and affordable.

In embodiments, the platform 100 includes a digital twin that represents an intelligent device and/or medication dosage environment and drug interaction effects.

In embodiments, the platform 100 includes a set of machine learning systems, a set of artificial intelligence systems, and/or a set of trained neural networks that are trained on a training data set of intelligent injection device 400 design, configuration, operation or outcome data to output at least one of a prediction, a token indicating a next member of a stream of data, a classification, a recommendation, an analytic result, a report or a control instruction.

In embodiments, the platform 100 includes a set of machine learning systems, a set of artificial intelligence systems, and/or a set of trained neural networks that are trained on a training data set of medical dosages administration data to output at least one of a prediction, a token indicating a next member of a stream of data, a classification, a recommendation, an analytic result, a report or a control instruction.

In embodiments, the platform 100 includes a machine learning system, artificial intelligence system, and/or neural network that is trained on training data set of intelligent injection device 400 design, configuration, operation or outcome data to output at least one of a prediction, a token indicating a next member of a stream of data, a classification, a recommendation, an analytic result, a report or a control instruction and that is configured to perform an optimization related to an intelligent injection device 400 or to an instance of medication dosage administration. The machine learning systems are configured to optimize the design, configuration, and operation of intelligent injection device 100XXs, enhancing their efficiency and effectiveness, which is beneficial in high-volume healthcare settings like hospitals. Machine learning algorithms analyze usage data from devices to continually improve their design and functionality, thereby ensuring that they meet the needs of both patients and healthcare providers.

In embodiments, the platform 100 includes a machine learning system, artificial intelligence system, and/or neural network that is trained on a training data set of medical dosages administration data to output at least one of a prediction, a token indicating a next member of a stream of data, a classification, a recommendation, an analytic result, a report or a control instruction and that is configured to perform an optimization related to an intelligent injection device 400 or to an instance of medication dosage administration. The artificial intelligence system and/or neural networks are configured to analyze medical dosage administration data to provide predictions and recommendations, improving treatment accuracy and patient outcomes, which is valuable in precision medicine. These systems analyze vast amounts of data to make accurate predictions about the optimal dosages for patients, reducing the risk of adverse effects and improving treatment outcomes.

In embodiments, the platform 100 includes a machine learning system, artificial intelligence system, and/or neural network that is trained on a training data set of intelligent injection device 400 design, configuration, operation or outcome data to output at least one of a prediction, a token indicating a next member of a stream of data, a classification, a recommendation, an analytic result, a report or a control instruction and that uses sensor fusion to perform an optimization related to an intelligent injection device 400 or to an instance of medication dosage administration. The machine learning algorithms are configured to use sensor fusion to optimize the performance of intelligent injection device 100XXs, enhancing their functionality and reliability, which is beneficial in critical care scenarios where device performance can directly impact patient survival. By integrating data from multiple sensors, machine learning algorithms can enhance the accuracy and reliability of device readings, thereby ensuring that injections are administered correctly.

In embodiments, the platform 100 includes a machine learning system, artificial intelligence system, and/or neural network that is trained on a training data set of medical dosages administration data to output at least one of a prediction, a token indicating a next member of a stream of data, a classification, a recommendation, an analytic result, a report or a control instruction and that uses sensor fusion to perform an optimization related to an intelligent injection device 400 or to an instance of medication dosage administration. The artificial intelligence systems are configured to analyze patterns in medication administration to predict future needs and outcomes, helping healthcare providers anticipate and mitigate potential issues, which is beneficial in chronic disease management where patient conditions can fluctuate. Predictive analytics help anticipate potential issues in medication administration, such as identifying patients who are at risk of non-compliance and allow for interventions before problems occur.

In embodiments, the platform 100 includes a machine learning system, artificial intelligence system, and/or neural network that is trained on a training data set of intelligent injection device 400 design, configuration, operation or outcome data to output at least one of a prediction, a token indicating a next member of a stream of data, a classification, a recommendation, an analytic result, a report or a control instruction and that is configured to generate a prediction related to an intelligent injection device 400 or to an outcome of an instance of medication dosage administration. The machine learning systems are configured to detect and identify optimal settings for intelligent injection device 100XXs based on usage patterns, thereby ensuring that devices are operating at their best, which is beneficial in settings where equipment reliability is critical. Algorithms analyze performance data to identify the most efficient settings for devices, thereby ensuring that they operate optimally in various clinical environments.

In embodiments, the platform 100 includes a machine learning system, artificial intelligence system, and/or neural network that is trained on a training data set of medical dosages administration data to output at least one of a prediction, a token indicating a next member of a stream of data, a classification, a recommendation, an analytic result, a report or a control instruction and that is configured to generate a prediction related to an intelligent injection device 400 or to an outcome of an instance of medication dosage administration.

In embodiments, the platform 100 includes a machine learning system, artificial intelligence system, and/or neural network that is trained on a training data set of intelligent injection device 400 design, configuration, operation or outcome data to output at least one of a prediction, a token indicating a next member of a stream of data, a classification, a recommendation, an analytic result, a report or a control instruction and that uses sensor fusion to generate a prediction related to an intelligent injection device 400 or to an instance of medical dosage administration.

In embodiments, the platform 100 includes a machine learning system, artificial intelligence system, and/or neural network that is trained on a training data set of medical dosages administration data to output at least one of a prediction, a token indicating a next member of a stream of data, a classification, a recommendation, an analytic result, a report or a control instruction and that uses sensor fusion to generate a prediction related to an intelligent injection device 400 or to an instance of medical dosage administration.

In embodiments, the platform 100 includes a machine learning system, artificial intelligence system, and/or neural network that is trained on a training data set of intelligent injection device 400 design, configuration, operation or outcome data to output at least one of a prediction, a token indicating a next member of a stream of data, a classification, a recommendation, an analytic result, a report or a control instruction and that is configured to detect and/or identify an intelligent injection device 400 or to an instance of medical dosage administration.

In embodiments, the platform 100 includes a machine learning system, artificial intelligence system, and/or neural network that is trained on a training data set of medical dosages administration data to output at least one of a prediction, a token indicating a next member of a stream of data, a classification, a recommendation, an analytic result, a report or a control instruction and that is configured to detect and/or identify an intelligent injection device 400 or to an instance of medical dosage administration.

In embodiments, the platform 100 includes a machine learning system, artificial intelligence system, and/or neural network that is trained on a training data set of intelligent injection device 400 design, configuration, operation or outcome data to output at least one of a prediction, a token indicating a next member of a stream of data, a classification, a recommendation, an analytic result, a report or a control instruction and that uses sensor fusion to detect and/or identify an intelligent injection device 400 or to an instance of medical dosage administration.

In embodiments, the platform 100 includes a machine learning system, artificial intelligence system, and/or neural network that is trained on a training data set of medical dosages administration data to output at least one of a prediction, a token indicating a next member of a stream of data, a classification, a recommendation, an analytic result, a report or a control instruction and that uses sensor fusion to detect and/or identify an intelligent injection device 400 or to an instance of medical dosage administration.

In embodiments, the platform 100 includes a machine learning system, artificial intelligence system, and/or neural network that is trained on a training data set of intelligent injection device 400 design, configuration, operation or outcome data to output at least one of a prediction, a token indicating a next member of a stream of data, a classification, a recommendation, an analytic result, a report or a control instruction and that is configured to detect and/or identify the needs and/or actions of an intelligent injection device 400 or to an instance of medical dosage administration. The artificial intelligence systems are configured to identify the needs and actions required for effective medication administration, facilitating proactive adjustments to treatment plans, which is useful in outpatient settings where patients manage their own care. AI systems analyze patient data to determine the specific actions needed to manage their conditions effectively, personalizing care and improving health outcomes.

In embodiments, the platform 100 includes a machine learning system, artificial intelligence system, and/or neural network that is trained on a training data set of medical dosages administration data to output at least one of a prediction, a token indicating a next member of a stream of data, a classification, a recommendation, an analytic result, a report or a control instruction and that is configured to detect and/or identify the needs and/or actions of an intelligent injection device 400 or to an instance of medical dosage administration. The machine learning algorithms are configured to classify intelligent injection device 100XXs based on their design and operation, which can be used to streamline device maintenance and updates, which is beneficial in large healthcare facilities managing multiple types of equipment. Classification algorithms help manage and maintain large fleets of injection device 100XXs, thereby ensuring that each device is properly serviced and functioning correctly.

In embodiments, the platform 100 includes a machine learning system, artificial intelligence system, and/or neural network that is trained on a training data set of intelligent injection device 400 design, configuration, operation or outcome data to output at least one of a prediction, a token indicating a next member of a stream of data, a classification, a recommendation, an analytic result, a report or a control instruction and that is configured to classify an intelligent injection device 400 or to an instance of medical dosage administration. The sensor fusion technologies are configured to enhance the classification accuracy of intelligent injection device 400, thereby ensuring that devices are correctly identified and managed, which is beneficial for maintaining device inventories and ensuring regulatory compliance. Integrating data from various sensors improves the classification and tracking of devices, enhancing inventory management and regulatory compliance.

In embodiments, the platform 100 includes a machine learning system, artificial intelligence system, and/or neural network that is trained on a training data set of medical dosages administration data to output at least one of a prediction, a token indicating a next member of a stream of data, a classification, a recommendation, an analytic result, a report or a control instruction and that is configured to classify an intelligent injection device 400 or to an instance of medical dosage administration.

In embodiments, the platform 100 includes a machine learning system, artificial intelligence system, and/or neural network that is trained on a training data set of intelligent injection device 400 design, configuration, operation or outcome data to output at least one of a prediction, a token indicating a next member of a stream of data, a classification, a recommendation, an analytic result, a report or a control instruction and that uses sensor fusion to classify an intelligent injection device 400 or to an instance of medical dosage administration.

In embodiments, the platform 100 includes a machine learning system, artificial intelligence system, and/or neural network that is trained on a training data set of medical dosages administration data to output at least one of a prediction, a token indicating a next member of a stream of data, a classification, a recommendation, an analytic result, a report or a control instruction and that uses sensor fusion to classify an intelligent injection device 400 or to an instance of medical dosage administration.

In embodiments, the platform 100 includes a generative AI system configured to generate a data story related to an intelligent injection device 400 or to an instance of medical dosage administration. The generative AI systems are configured to create comprehensive data stories related to intelligent injection device 100XXs, providing insights into device usage and patient interactions, which can be used for educational purposes and/or to improve device design. Generative AI creates narratives from complex data sets, helping patients and providers understand treatment progress and outcomes in a more engaging and accessible way.

In embodiments, the platform 100 includes a machine learning system, artificial intelligence system, and/or neural network that is trained on a training data set of intelligent injection device 400 design, configuration, operation or outcome data to output at least one of a prediction, a token indicating a next member of a stream of data, a classification, a recommendation, an analytic result, a report or a control instruction and that is configured to improve differences between supply and demand of a set of intelligent injection device 100XXs or a set of medication doses across set of locations and times. The artificial intelligence systems are configured to analyze supply and demand trends for intelligent injection device 100XXs and medication doses, optimizing resource allocation and reducing waste, which is beneficial in global health initiatives aiming to improve access to beneficial medications.

In embodiments, the platform 100 includes a machine learning system, artificial intelligence system, and/or neural network that is trained on a training data set of medical dosages administration data to output at least one of a prediction, a token indicating a next member of a stream of data, a classification, a recommendation, an analytic result, a report or a control instruction and that is configured to improve differences between supply and demand of a set of intelligent injection device 100XXs or a set of medication doses across set of locations and times. AI systems analyze global supply and demand trends to optimize the distribution of medications and devices, thereby ensuring that resources are used efficiently and that shortages are minimized.

In embodiments, the platform 100 includes a machine learning system, artificial intelligence system, and/or neural network that is trained on a training data set of intelligent injection device 400 design, configuration, operation or outcome data.

In embodiments, the platform 100 includes a machine learning system, artificial intelligence system, and/or neural network that is trained on a training data set of medical dosages administration data.

In embodiments, the platform 100 includes a transaction intelligence and infrastructure system for injections administered via the intelligent injection device 400. The machine learning systems are configured to provide transaction intelligence for injections administered via intelligent devices, enhancing the efficiency and transparency of healthcare transactions, which is beneficial in healthcare systems with complex billing and reimbursement processes. The technology enhances the transparency and efficiency of healthcare transactions, such as billing and insurance claims, reducing errors and improving financial management.

In embodiments, the platform 100 includes a content and advertising system for injections administered via the intelligent injection device 400. The content and advertising system delivers targeted educational materials and advertisements, which can be customized to patient demographics and health conditions, thereby enhancing patient education and engagement. Targeted content and advertising deliver personalized educational materials to patients, helping them understand their conditions and treatments better, which can lead to improved health outcomes.

In embodiments, the platform 100 includes a custody and supply chain management system for injections administered via the intelligent injection device 400. The custody and supply chain management system ensures that medications are securely managed and tracked from manufacturer to patient, reducing the risk of errors and fraud, which is beneficial in pharmaceutical logistics. The system tracks medications throughout the supply chain, from manufacturing to patient administration, thereby ensuring that drugs are not tampered with or diverted, enhancing patient safety.

In embodiments, the platform 100 includes a system for monitoring and managing the drawing of blood and detecting of blood contents via the intelligent injection device 400. The system for monitoring and managing the drawing of blood and detecting of blood contents can be used in diagnostic processes to adjust medication dosages in real-time, which is beneficial in conditions like diabetes where blood glucose levels frequently change. The system for monitoring and managing the drawing of blood and detecting of blood contents via the intelligent injection device 400 allows for real-time analysis of blood contents during the drawing process, enabling immediate adjustments to medication dosages based on the latest health data.

In embodiments, the platform 100 includes a system for monitoring and managing the administration of injected medication for veterinary applications via the intelligent injection device 400. The system for monitoring and managing the administration of injected medication for veterinary applications ensures that animals receive the correct dosages and treatments, which is beneficial in veterinary clinics and animal hospitals. The system ensures that animals receive the correct dosages of medications, which is beneficial for the effective treatment of diseases in veterinary settings.

In embodiments, the platform 100 includes a system for monitoring and managing the administration of injected medication for pets via the intelligent injection device 400. The system for monitoring and managing the administration of injection medication for pets ensures that domestic animals receive appropriate care, useful for pet owners managing chronic conditions in their animals, such as diabetes. The system manages the administration of medications to pets, thereby ensuring that they receive appropriate care, which is beneficial for pets with chronic conditions.

In embodiments, the platform 100 includes a system for monitoring and managing the administration of injected medication for horses administered via the intelligent injection device 400. Designed specifically for equine patients, the system ensures that horses receive proper medical treatment, which is beneficial in settings such as racetracks and equestrian centers.

In embodiments, the platform 100 includes a system for monitoring and managing pre-acute, out-of-hospital care administered via the intelligent injection device 400. The system for monitoring and managing pre-acute, out-of-hospital care administered via the intelligent injection device 400 supports the administration of care in pre-acute and out-of-hospital settings, thereby ensuring that patients receive timely medical interventions in emergency situations.

In embodiments, the platform 100 includes a system for detecting an injection angle of an intelligent injection device 400. The system for detecting an injection angle ensures that injections are performed correctly, reducing the risk of complications, which is beneficial in delicate procedures like spinal injections.

In embodiments, the platform 100 includes a system for managing injections related to cooking and food preparation via the intelligent injection device 400, which ensures that substances like marinades are injected safely and effectively and is useful in culinary settings where precise flavoring injection is required.

In embodiments, the platform 100 includes a system for managing injections related manufacturing applications via the intelligent injection device 400, which ensures that materials like lubricants or dyes are administered precisely, which is beneficial in industrial settings where accuracy can impact product quality.

Figure 4A:
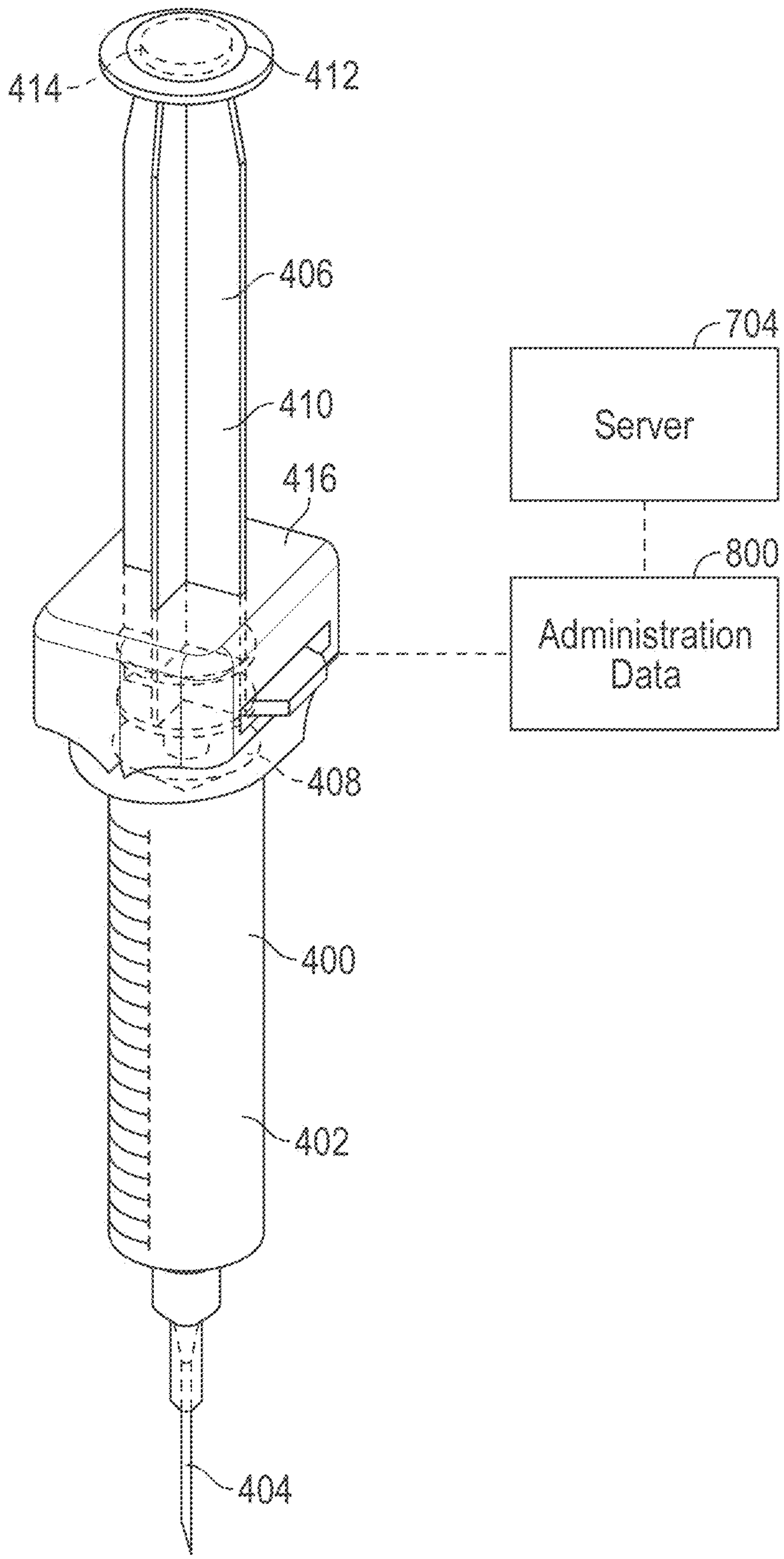
FIG. 4A is a diagram that illustrates a reporting injection device according to some embodiments of the present disclosure.
Figure 4B:
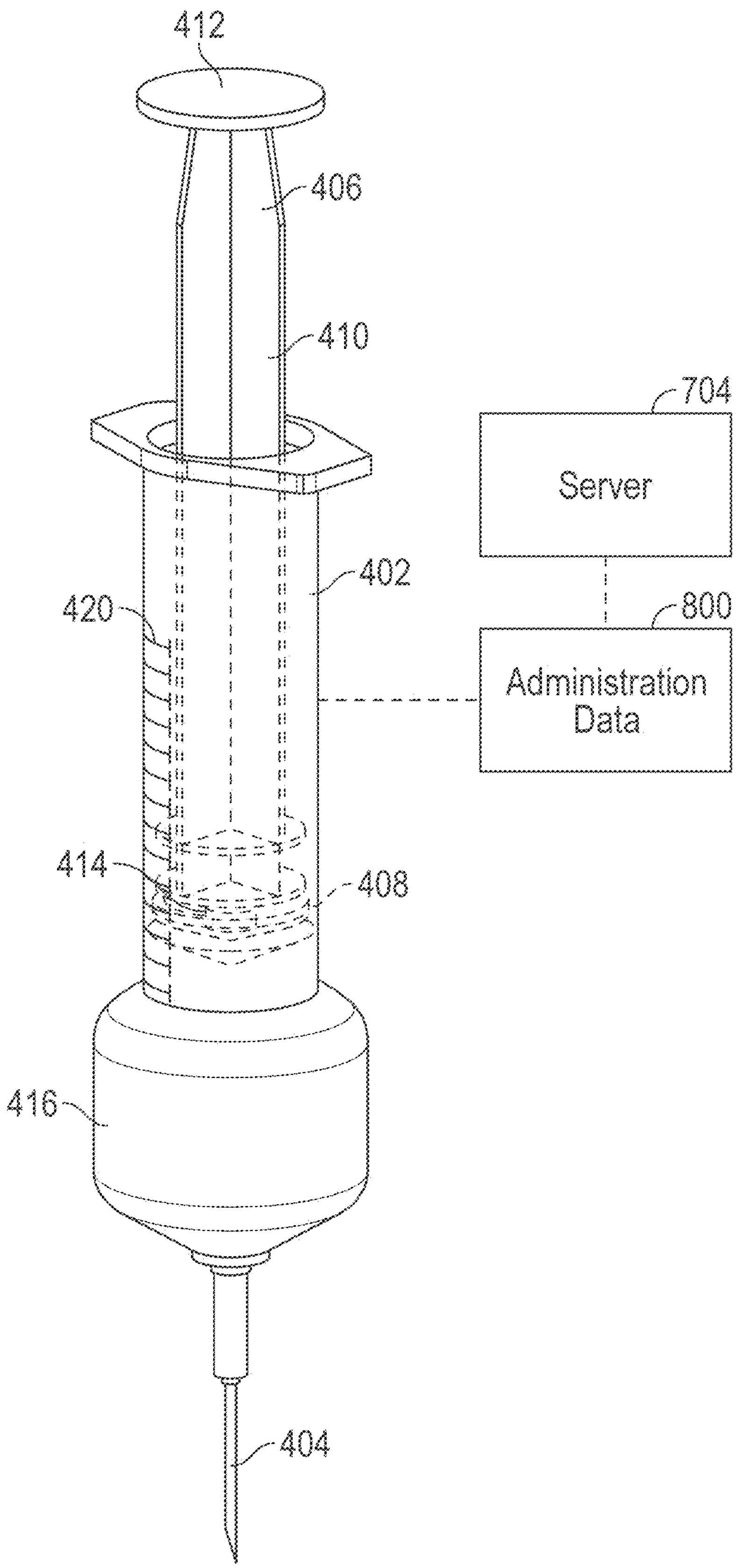
FIG. 4B is a diagram that illustrates a reporting injection device of having an alternate arrangement of reporting components according to some embodiments of the present disclosure.

FIG. 4B illustrates embodiments of an injection device 400. The injection device 400 may include a barrel 402 having a first end and a second end. The barrel 402 may be sized to receive and/or store a fluid, such as a pharmaceutical, a medication, a biologic, or any other suitable fluid. With respect to diabetes management, the barrel 402 may be sized to retain sufficient insulin for one prescribed administration. The injection device may include a needle 404 connected with the first end of the barrel and in fluid communication with the barrel 402 for injecting pharmaceutical into the patient. The needle 404 may define a hollow conduit through which the pharmaceutical may be transported from the barrel 402 through the needle 404 and into the patient.

The injection device 400 may include a piston 406 for driving the pharmaceutical during injection. The piston 406 includes a plunger 408, a stalk 410, and a head 412. The plunger 408 may be positioned within the second end of the barrel 402 and may engage the inside of the barrel 402 such that a seal is created, the seal being sufficient to push retained pharmaceutical from the barrel 402 through the needle 404. The plunger 408 may be connected to the stalk 410. The stalk 410 may be connected to the head 412. The plunger 408 may be driven through the barrel 402 by operation of pressing the head 412 toward the barrel. The plunger may be at least partially composed of rubber, plastic, or any other material sufficient to maintain a fluid-tight interaction between the plunger 408 and an interior of the barrel 402 such that pharmaceutical is administered as the piston 406 is compressed. The stalk 410 may have sufficient length to drive the plunger 408 to a distal end of the barrel 402. In this manner, some, most, or all of the pharmaceutical may be driven out of the barrel 402.

In some embodiments, the head 412 may include a magnet 414. The magnet 414 may be a neodymium magnet or other magnet sufficient to induce a magnetic field onto reporting components 416 when the head 412 is completely pressed to the casing of the reporting components 416. When the magnetic field is induced onto the reporting components 416, the reporting components 416 may send administration data 800 to a server 704 over an internet connection (e.g., wireless, cellular data, etc.). In some embodiments, the magnetic field may be induced onto the reporting components 416 when the head 412 is almost completely pressed to the casing of the reporting components 416, such as when the injection administration is effectively complete (e.g., when the head 412 is 98% compressed or other predetermined and/or reconfigurable values).

In some embodiments, a mechanical switch may be used to indicate that the injection has been administered by compressing the switch when the head 412 is completely (or almost completely) pressed to the casing of the reporting components 416 or to an end of the barrel 402. In these embodiments, a reporting circuit may be completed or broken. Detection of this change in the circuit may, in embodiments, allow for a microprocessor 510 (FIG. 5A) in the reporting components 416 to alter the administration data 800 to reflect a completed injection.

FIG. 4A illustrates other embodiments of the injection device 400. By way of these examples, the magnet 414 may be positioned in the plunger 408. The reporting components 416 may be positioned at the end of the barrel 402 proximate the needle 404.

Figure 5A:
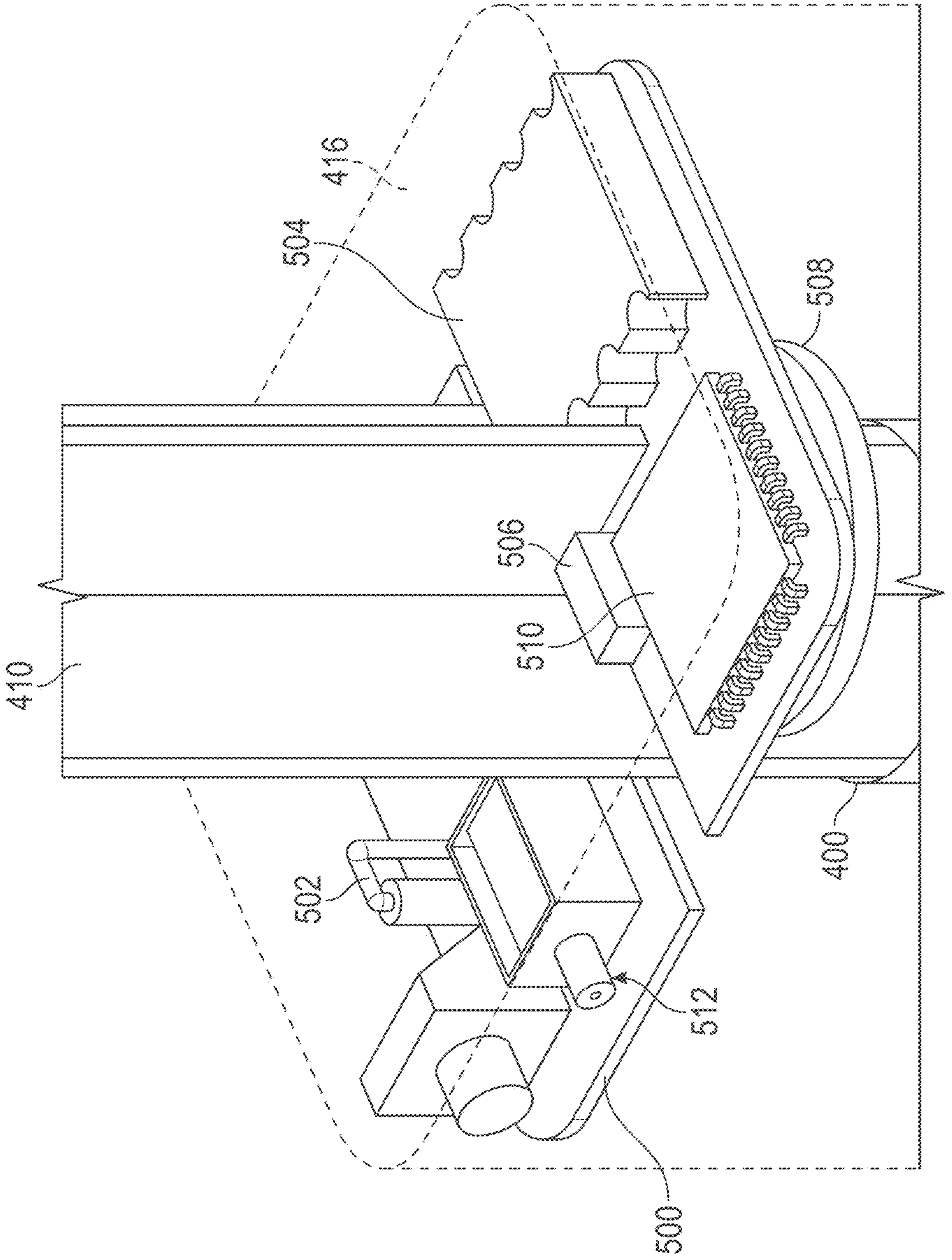
FIG. 5A is a diagram that illustrates reporting components of the injection device according to some embodiments of the present disclosure.

FIG. 5A illustrates embodiments of the injection device 400 including the reporting components 416 of the injection device 400. For example, the reporting components 416 may include a temperature sensor 502, a wireless module 504, a switch 506, a battery 508, a microprocessor 510, and/or a locking mechanism 512.

The battery 508 may be a coin cell battery or any other battery sufficient to power the reporting components 416. Coin cell batteries may provide a stable output voltage until the end of the life of the battery. Coin cell battery capacities may range from 450 to 500 mAh and voltage characteristics may range from gradually reducing to fairly constant. Some coin cell batteries may be specified for a continuous low drain with a high pulse on demand.

The temperature sensor 502 may be or include any suitable device for measuring temperature and providing an electronic measurement to the microprocessor 510. Examples of suitable devices include a thermistor, a resistance temperature detector, a thermocouple, and/or a semiconductor-based sensor. In some embodiments, the temperature sensor 502 may be positioned on a circuit board of the reporting components 416. The temperature sensor 502 may be configured to measure the temperature ambient to the injection device 400, such as by measuring the temperature of the air around the reporting components 416. However, embodiments may include a temperature probe within the barrel 402 in order to measure the temperature of the pharmaceutical.

A thermistor may include a thermally sensitive resistor that may exhibit a large, predictable, and precise change in resistance correlated to variations in temperature. A negative temperature coefficient (NTC) thermistor provides a very high resistance at low temperatures. As temperature increases, the resistance may decrease. Because an NTC thermistor may experience a large change in resistance per° C., small changes in temperature may be reflected quickly and with high accuracy (0.05 to 1.5° C.). Because of its exponential nature, the output of an NTC thermistor may require linearization. The effective operating range may be −50 to 550° C. for gas encapsulated thermistors or 450° C. for standard.

A resistance temperature detector (RTD), also known as a resistance thermometer, may measure temperature by correlating the resistance of the RTD element with temperature. An RTD may consist of a film or, for greater accuracy, a wire wrapped around a ceramic or glass core. The most accurate RTDs may be made using platinum. However, lower-cost RTDs can be made from nickel or copper, at a cost to accuracy. Platinum RTDs offer a fairly linear output that may be highly accurate (0.1 to 1° C.) across-500 to 900° C.

A thermocouple may consist of two wires of different metals connected at two points. The varying voltage between these two points may reflect proportional changes in temperature. The thermocouple may be non-linear, requiring conversion when used for temperature control and compensation. However, conversion can be accomplished using a lookup table. Accuracy may be relatively low, from 0.5 to 5° C. However, thermocouples may operate across the widest temperature range, from −500 to 1750° C.

In some embodiments, the temperature sensor 502 may be placed on an integrated circuit (IC). The temperature sensor may include two identical diodes with temperature-sensitive voltage vs current characteristics that can be used to monitor changes in temperature. The diodes of the temperature sensor 502 may offer a linear response.

In some embodiments, the wireless module 504 may be placed on the circuit board 500 such that the wireless module 504 may be in electrical communication with the microprocessor 510 and the battery 508. The wireless module 504 may include a Bluetooth interface, a Bluetooth low energy interface, a Wi-Fi interface, an infrared interface, a cellular interface (e.g., a fixed area transceiver), a near field communication (NFC) interface, a radio-frequency identification (RFID) interface, or any other suitable communication interface.

In some embodiments, the wireless module 504 may be configured to connect to the internet, a computer, and/or a mobile phone. For example, the wireless module 504 may connect directly or indirectly to a local router, modem, server, transmitter tower such as a radio tower, satellite and/or any other gateway to the worldwide web. In some embodiments, the wireless module 504 may be wirelessly connected directly to another computer or handheld device, such as a phone, watch, or tablet. In some embodiments, the wireless module 504 may engage in electronic communication with another computer or device by infrared (IR) transmitter and receiver, Bluetooth connection, fiber optic connection, cellular or mobile network (e.g., fixed area transceivers), or any other connector for transferring electronic data. For example, the wireless module 504 may send data over Bluetooth connection to a computer, server, or other devices. The server 704 may then upload the data for access via an internet connection. The wireless module 504 may transmit data via analog or digital signal, UDP or TCP, http, https, ssh, ftp, sftp, etc., or any other protocol or means to transfer electronic data.

The switch 506 may be a magnetic and/or electrical switch, such as a reed switch. The switch 506 may be positioned on the circuit board 500. The switch 506 may be in electrical communication with the microprocessor 510, the locking mechanism 512, and/or any other reporting components 416. A reed switch may be operated by an applied magnetic field. The reed switch may include a pair of contacts on ferromagnetic metal reeds in a hermetically scaled glass envelope. The contacts may be normally open, closing when a magnetic field is present, or normally closed and opening when a magnetic field is applied. The reed switch may be actuated by a coil, making a reed relay, or by bringing a magnet near to the switch. Once the magnet is pulled away from the switch, the reed switch may go back to its original position. In this manner, the switch 506 may be actuated by application of the magnetic field of the magnet 414, such as when the piston 406 is compressed upon administering an injection or bolus of a pharmaceutical from the barrel 402.

The locking mechanism 512 may be positioned on the circuit board 500. In this manner, the locking mechanism 512 may be in electrical communication with the other components on the circuit board 500, such as the wireless module 504 and/or the microprocessor 510. The locking mechanism 512 may prevent injection of the pharmaceutical by interaction with the stalk 410, when in the locked position. However, the locking mechanism 512 may be switched to an unlocked position, wherein the locking mechanism 512 no longer interacts with the stalk 410. Thereby, the piston 406 may be compressible to allow an injection when the locking mechanism 512 is in the unlocked position.

In some embodiments, the locking mechanism 512 may engage the locked position upon filling the barrel with a prescribed amount or bolus of a pharmaceutical. The locking mechanism 512 may remain in the locked position until predetermined conditions are met. For example, the locking mechanism 512 may remain in the locked position until the microprocessor 510 verifies a user connection between the wireless module 504 and a user device, such as an app on a mobile device. In some embodiments, the locking mechanism 512 may switch to the unlocked position upon meeting one or more, or all, of the predetermined conditions.

An example may include sensing that an injection physically occurs within a patient, such as by a load sensor.

The microprocessor 510 may be positioned on the circuit board 500. In this manner, microprocessor 510 may be in electrical communication with the other components on the circuit board 500, such as the temperature sensor 502, the wireless module 504, the switch 506, the battery 508, and/or the locking mechanism 512.

FIG. 5B illustrates the reporting components 416 of the reporting injection device 400.

Figure 5C:
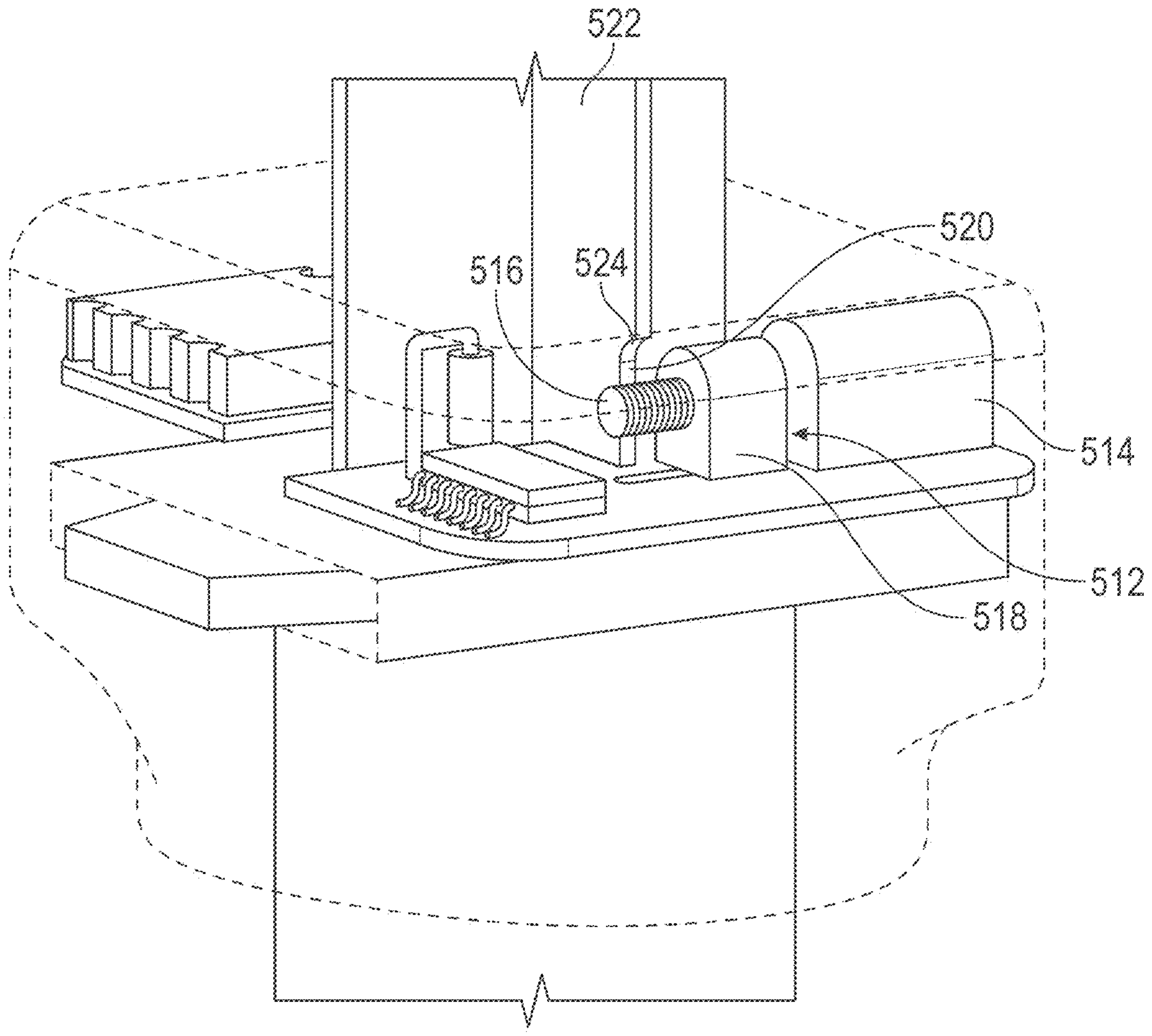
FIG. 5C is a diagram that illustrates a locking mechanism of the reporting components of the reporting injection device with the locking mechanism disengaged according to some embodiments of the present disclosure.

FIG. 5C illustrates the locking mechanism 512 of the reporting components 416 with the locking mechanism 512 disengaged.

The locking mechanism 512 may include a stepper motor, such as micro stepper motor 514. The micro stepper motor 514 may be in rotary communication with a screw 516 such that rotation of the micro stepper motor 514 may rotate the screw 516. A slider block 518 may be disposed on the screw 516 such that rotation of the screw 516 may alter the linear displacement of the slider block 518. For example, the slider block 518 may include threads that interact with the threads of the screw 516 such that rotation of the screw 516 in a first direction may move the slider block 518 proximally to the micro stepper motor 514 and rotation of the screw in a second direction may move the slider block 518 distally from the micro stepper motor 514.

The locking mechanism 512 may further include a slider block receiver 520. The slider block receiver 520 may be integrally formed with the plunger 408 such that a plunger wall 522 of the plunger 408 includes a flange 524 configured to contact the slider block 518 when the slider block 518 is positioned under the flange 524. In some embodiments, the flange 524 may not necessarily contact anything when the slider block 518 is not positioned under the flange 524, such that the plunger wall 522 may pass the slider block 518 and the injection device 400 may be compressed.

Figure 5D:
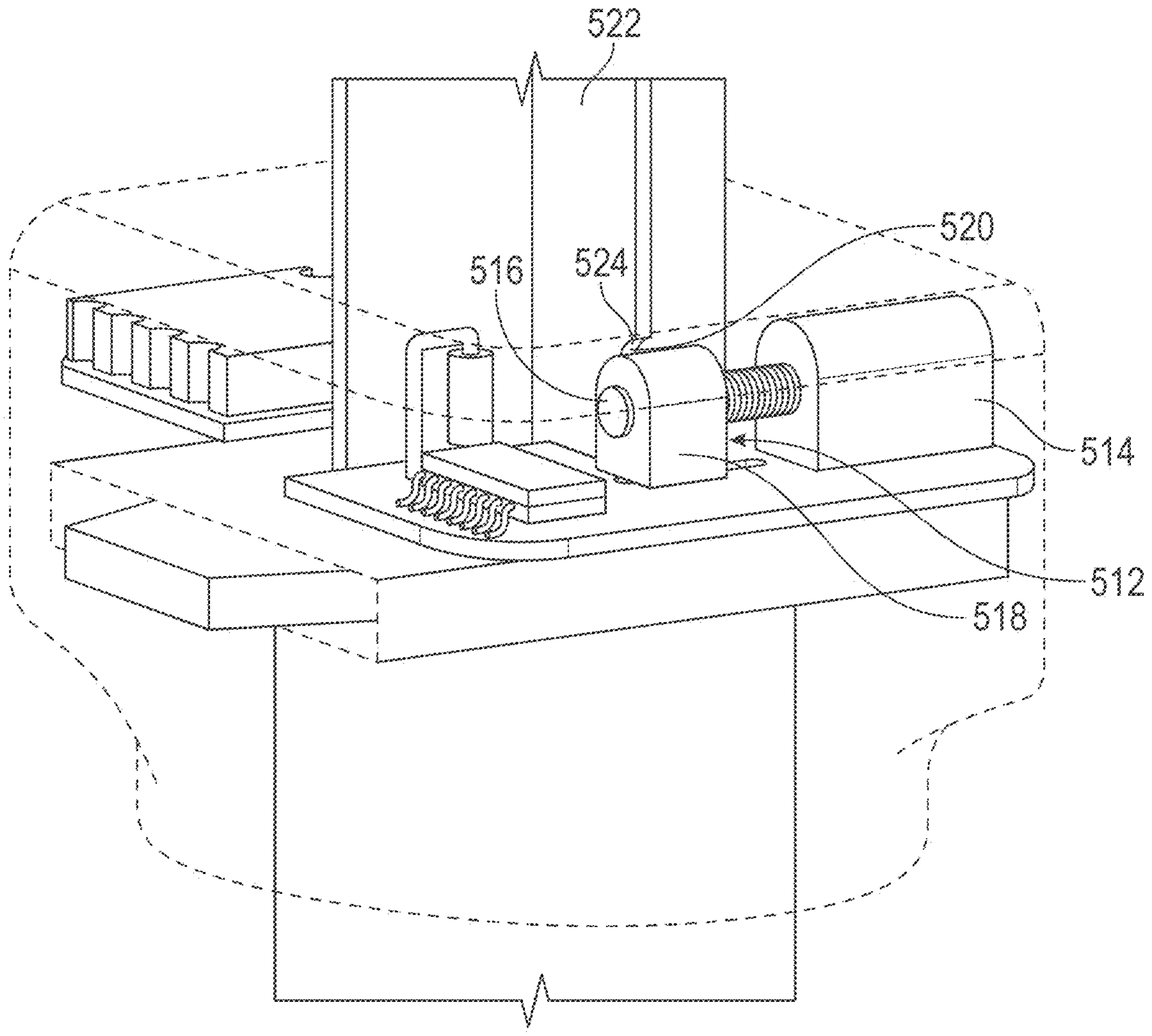
FIG. 5D is a diagram that illustrates the locking mechanism of the reporting components of the reporting injection device with the locking mechanism engaged according to some embodiments of the present disclosure.

FIG. 5D illustrates the locking mechanism 512 of the reporting components 416 of the reporting injection device 400 with the locking mechanism 512 engaged. While the locking mechanism 512 is engaged, the flange 524 may contact the slider block 518. Because the flange 524 and/or the plunger wall 522 will not pass through the slider block 518, the injection device 400 is prevented from compression and/or injection when the locking mechanism 512 is engaged.

In some embodiments, locking and/or unlocking the injection device 400, i.e., engaging or disengaging the locking mechanism 512, may be determined by the disposition of the axis of the screw 516 through the plane of the plunger wall 522 such that flange 524 is or is not capable of contacting the screw 516 and is not or is capable of contacting the slider block 518 when the slider block 518 is positioned under the flange 524. In some embodiments, the plunger wall 522 may define a mortise and the flange 524 may contact the slider block 518 (e.g., as a tenon) to prevent injection when the slider block 518 is positioned in the mortise.

The injection device may include any other suitable locking mechanism.

Figure 5E:
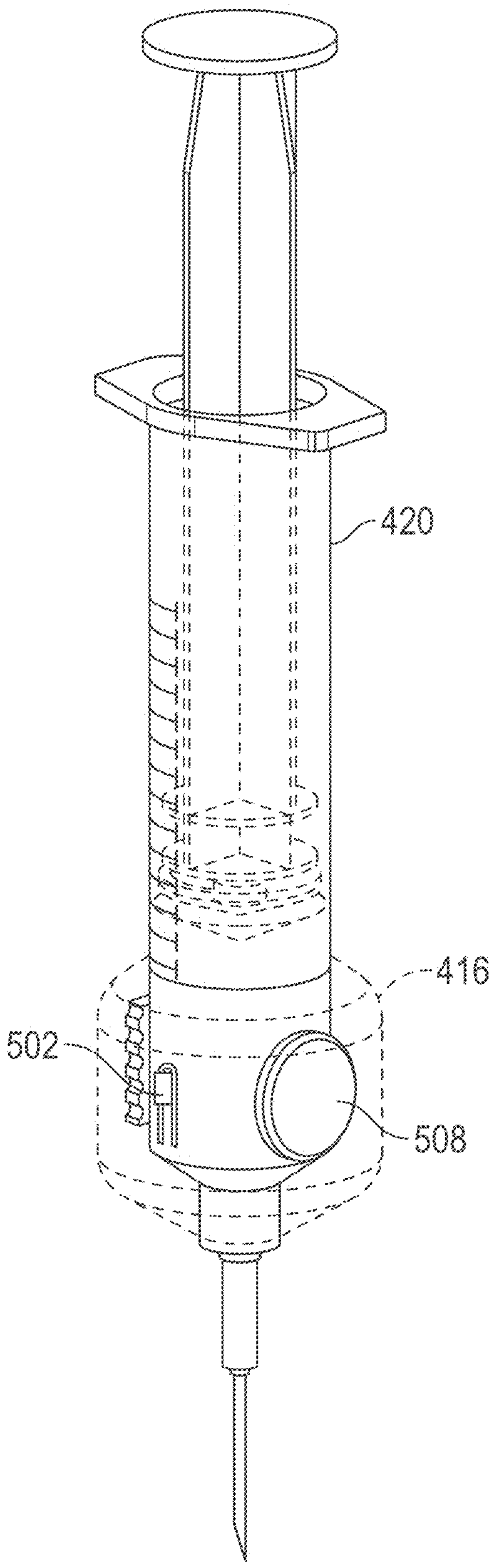
FIG. 5E is a diagram that illustrates an alternate view of the reporting components according to some embodiments of the present disclosure.

FIG. 5E illustrates other embodiments of the reporting components 416. In some embodiments, the injection device 400 includes the reporting components 416 that do not necessarily include the locking mechanism 512. The sensor 502 may detect the proximity of the magnet 414 in the plunger 408 when an injection is completely administered. The microprocessor 510 may record the injection administration completion event and may send the administration data 800 over the wireless module 504.

Figure 6:
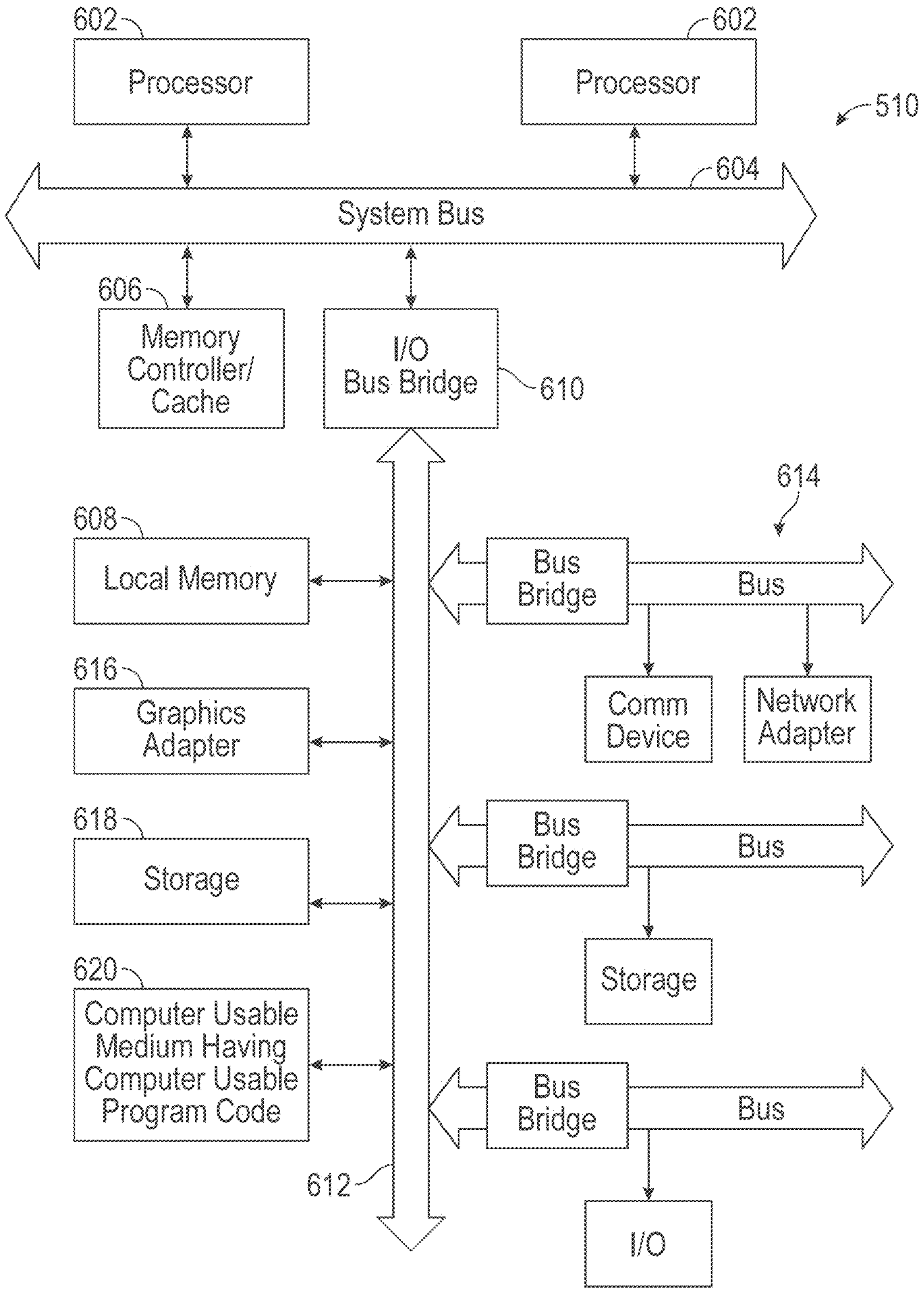
FIG. 6 is a diagram that illustrates a microprocessor of the injection device according to some embodiments of the present disclosure.

FIG. 6 illustrates embodiments of a block-level diagram of the microprocessor 510 of the injection device 400. The microprocessor 510 may be any device capable of sending and receiving electronic data over an interface. For example, a microprocessor or a computer could be used. The microprocessor 510 may also perform operations on and/or modify the data it receives.

The microprocessor 510 may be embodied as hardware circuits or may be software embodiments wherein program code, such as java, C++, etc., manipulates the hardware of a general-purpose hardware circuit. Software embodiments may be implemented as low-level code or even as high-level code operating within an operating system, such as Unix, BSD, Microsoft Windows, iOS, etc.

The microprocessor 510 may include a processing unit (CPU) 602, a local memory 608, a plurality of peripherals and interfaces, and a general-purpose input/output (I/O) interface. The CPU 602 may include local storage. The local storage may be used to store variables, constants, etc. for complex calculations. The local memory 608 may interface with the CPU via a memory interface. The memory interface may allow the CPU to store calculated values, variables, constants, or any other important electronic signal onto physical local memory. The memory interface may include one or more direct memory access controllers. Part or all of the local memory 608 may be committed to program storage, in which data relevant to the operation of the program is stored. Program storage may also be organized into useful data structures such as a stack or heap. The peripherals and interface and the general purpose I/O interface may interface to external input or output devices. Examples of external input or output devices include any electronic device capable of sending or receiving an electronic signal such as keyboards, mice, printers, scanners, digital sensors, analog sensors, Ethernet, analog to digital converters, ADC, UART, USB, etc. Program storage, local memory, peripherals and interface, and general purpose I/O interface may be contained on the circuit board of the CPU. The microprocessor 510 may further include a screen whereby the graphics adapter 916 may alter the display, such as at validation or denial of a ticket. In some embodiments, any of these parts may be external to the CPU.

The microprocessor 510 may include a symmetric multiprocessor (SMP) system or other configuration including a plurality of processors 602 connected to system bus 604. In some embodiments, a single processor 602 may be employed. A memory controller/cache 606 may be connected to the system bus 604, which may provide an interface to the local memory 608. An I/O bus bridge 610 may be connected to the system bus 604 and may provide an interface to an I/O bus 614. The I/O bus 612 may be utilized to support one or more buses and corresponding devices, such as bus bridges, input-output devices (I/O devices), storage, network adapters, etc. Thus, a network adapter may be coupled to the system to enable the data processing system to become coupled to other data processing systems or remote printers or storage devices through intervening private or public networks.

In some embodiments, devices such as a graphics adapter 616, storage 618 and a computer-usable storage medium 620 may be connected to the I/O bus 612 and may have computer usable program code embodied thereon. The computer-usable program code may be executed, e.g., by one or more processors to implement one or more aspects of the present disclosure, for example, to implement any aspect of any of the methods, processes and/or system components with respect to the present disclosure. For instance, the computer usable program code can be utilized to implement a linker that implements any one or more of the methods described herein. Moreover, the computer-usable program code may be implemented in the local memory 608 or other suitable storage media.

In some embodiments, the reporting components 416 may include an attachable and/or detachable self-contained unit. In these embodiments, the reporting components 416 may include a case that is shaped to snap-fit over the piston receiving end of the injection device 400. Furthermore, sensors, such as the temperature sensor 502, may detect the ambient temperature of the reporting components 416 as an approximation of temperature of the pharmaceutical in the barrel 402.

Figure 7:
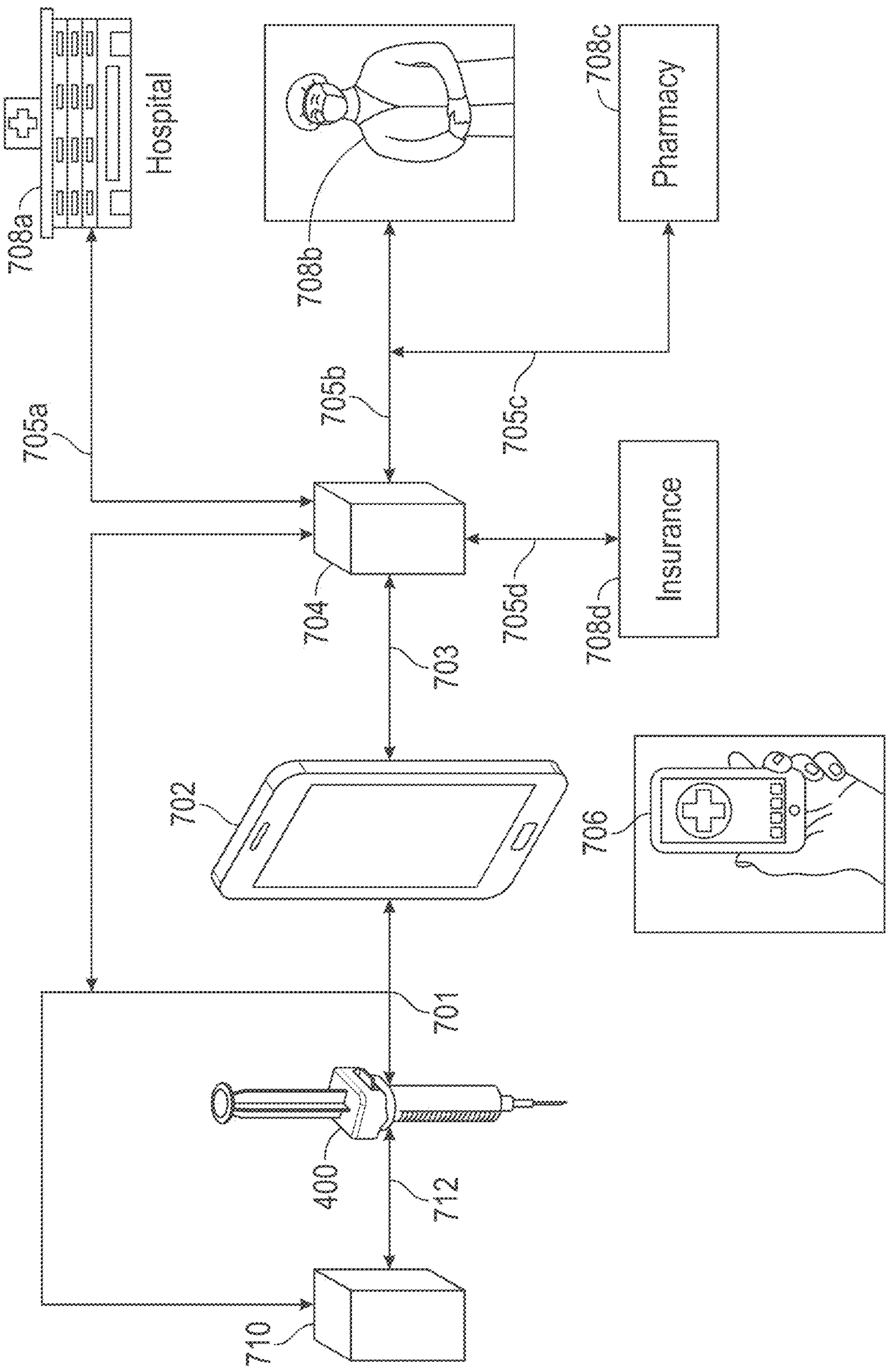
FIG. 7 is a diagram that illustrates data generation by the injection device and data sharing according to some embodiments of the present disclosure.

FIG. 7 illustrates a diagram of data generation by the injection device 400 and data sharing. A processor and/or microprocessor of a patient device 702 and/or a server 704 may be substantially similar to the microprocessor 510 such that the patient device 702 and/or the server 704 may be programmable to carry out the processes.

Internet connection, such as a wireless connection 701 and/or internet connection 703, 405*a-d* may be established via internet connection hardware such as a circuit configured as a wired or wireless internet adapter or other means of electronic communication. In some embodiments, the wireless connection 701 may connect the injection device 400 to the patient device 702 over the wireless interface 504. For example, the internet connection 703, 705*a*-705*d* may be substantially similar to the wireless connection 701. In some embodiments, the internet connection 703, 705*a*-705*d* may include an Ethernet jack for wired connection directly or indirectly to a local router, modem, server, transmitter tower such as a radio tower, satellite and/or any other gateway to the worldwide web. In some embodiments, the internet connection 703, 705*a*-705*d* may include a wireless card or circuit. The wireless card may be wirelessly connected directly or indirectly to a local router, modem, server, transmitter tower such as a radio tower, satellite and/or any other gateway to the worldwide web. In some embodiments, the internet connection 703, 705*a*-705*d* may be wirelessly connected directly to another computer or handheld device, such as a phone, watch, or tablet. In other embodiments, the internet connection 703, 705*a*-705*d* may engage in electronic communication with another computer or device by infrared (IR) transmitter and receiver, Bluetooth connection, fiber optic connection, cellular or mobile network (e.g., fixed area transceivers), or any other connector for transferring electronic data. For example, the internet connection 703, 705*a*-705*d* may send data over Bluetooth connection to a computer, server, or other devices. The server 704 may then upload the data for access via the internet connection 703, 705*a*-705*d*. Additional embodiments include an internet connection 703, 705*a*-705*d* that is configured to send the store data over Bluetooth, infrared communication, etc. directly to the server 704. Internet connection 703, 705*a*-705*d* may transmit data via analog or digital signal, UDP or TCP, http, https, ssh, ftp, sftp, etc., or any other means to transfer electronic data.

The internet connection 703 may provide for electronic communication between the patient device 702 and the server 704. The internet connection 705*b* may provide for electronic communication between the server 704 and a health care stakeholder, such as a physician 708*b*. Internet connection 705*c* may provide for electronic communication between the server 704 and a health care stakeholder, such as a pharmacy 708*c*. The internet connection 705*d* may provide for electronic communication between server 704 and a health care stakeholder, such as an insurance provider 405*d*.

In some embodiments, the patient device 702 may include an app 706, such as by having the app 706 installed thereon. The app 706 may manage the wireless connection 701 and electronic communications between the injection device 400 and the patient device 702. For example, the app 706 may be registered to a patient, such that the patient may be verified. Patient verification may be provided through a password protected login system and/or a digital certificate system. Once verified, the patient may review treatment data stored by the server 704 by communication between the patient device 702 and the server 704 over internet connection 703. Treatment data may include treatment history and may include patient compliance data.

In some embodiments, verification of the patient may unlock the locking mechanism 512 in the injection device 400 such that pharmaceutical may be administered via the injection device 400. In some embodiments, the injection device 400 may be preregistered to a patient, such as by a pharmacy 408*c* that fills the prescription for the drug in the injection device 400. The app 706 may provide patient verification data to the microprocessor 510. The microprocessor 510 may unlock the locking mechanism 512 upon patient verification. In some embodiments, the injection device 400 may not necessarily be preregistered to a patient. In these embodiments, the app 706 may provide patient information, such as a patient ID, or the app 706 may record injection device information, such as an injection device ID. The app 706 may signal that injection may proceed, and the microprocessor 510 may unlock the locking mechanism 512.

In some embodiments, the wireless connection 701 may establish electronic communication between the injection device 400 and the patient device 702. The injection device 400 may send the administration data 800 to the patient device 702 over the wireless connection 701. The wireless connection 701 may establish electronic communication between the injection device 400 and the server 704. The injection device 400 may send the administration data 800 to the server 704 over the wireless connection 701.

In some embodiments, one or more health care stakeholders 408*a*-408*d* may access the server 704 to review treatment data stored on the server 704 for corresponding patients. In this manner, stakeholders 708*a*-708*d* may make treatment and/or coverage decisions. For example, a provider (e.g., a hospital 708*a* or a physician 708*b*) may guide a noncompliant patient towards compliance in order to achieve better treatment outcomes. Additionally, if the desired treatment outcome is not achieved by compliance, alternative treatments may be chosen. Insurance provider(s) 708*d* may incentivize compliance through allowable avenues or vehicles, such as with additional coverage and/or lower premiums. However, insurance provider 708*d* may intervene when non-compliance occurs, such as by withdrawing coverage for treatments wherein the patient is noncompliant. One or more pharmacy stakeholders 708*c* may compare treatment data to prescriptions in order to provide for timely refills available to encourage patient compliance and also to assess for compliance with a treatment regimen. This process may encourage compliance with the proper administration of prescribed pharmaceuticals.

Figure 8:
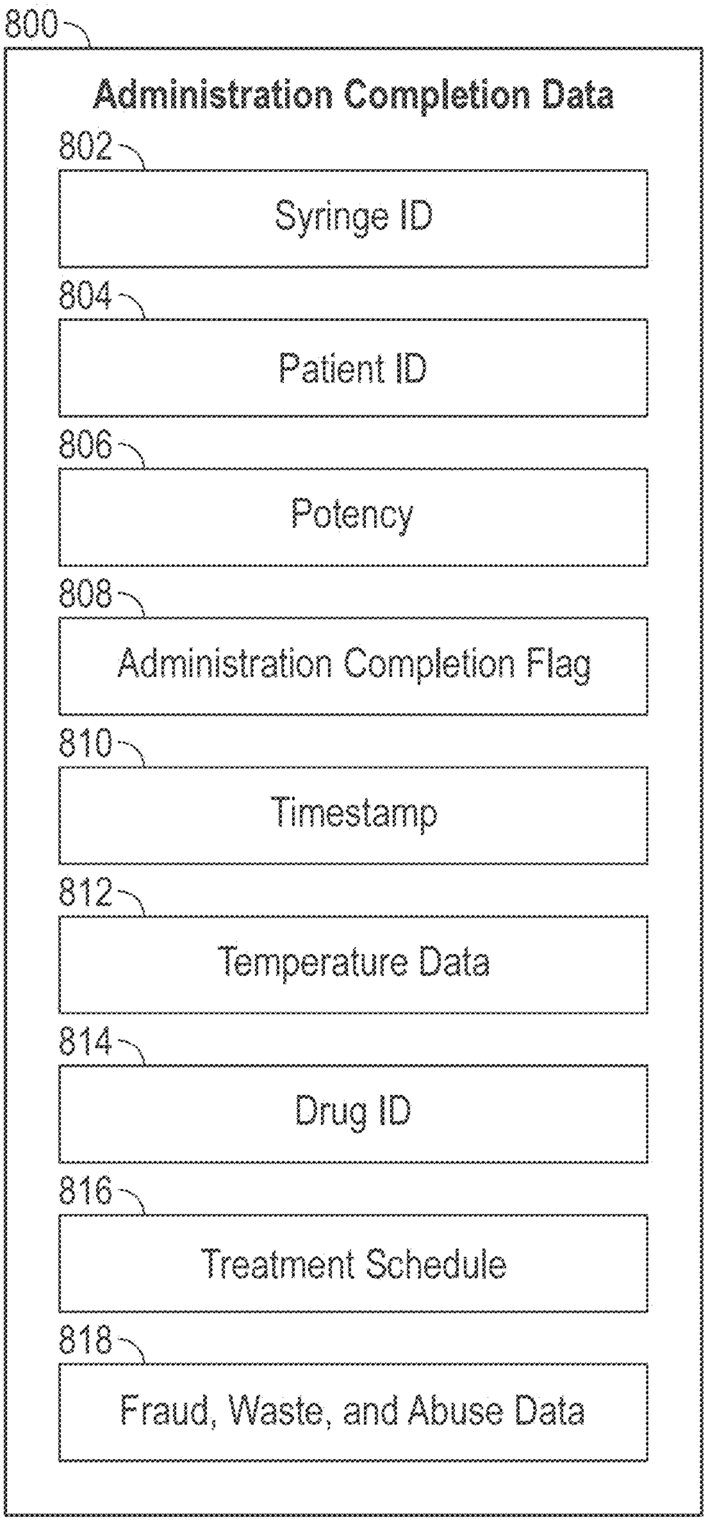
FIG. 8 is a block-level diagram that illustrates administration data as it can be stored on the injection device according to some embodiments of the present disclosure.

FIG. 8 illustrates a block-level diagram of the administration data 800 as can be stored on the injection device 400. The administration data 800 may include an injection device ID 802. In some embodiments, the injection device ID 802 can be associated with a manufacturing lot of the injection device 400 or of a pharmaceutical contained in the injection device 400. Furthermore, the administration data 800 may include a drug ID 814 of the contained pharmaceutical for identifying the drug and/or the manufacturing lot of the drug.

The administration data 800 may further include a patient ID 804. The patient ID 804 may be set by the pharmacy 408*c* or by the app 706. A potency 806 may include the volume and/or concentration of the entire amount of the injectable drug contained in the injection device 400. The administration data 800 may include an administration completion flag 808, such as a binary indication of whether the injection was completely administered, as detected by the injection device 400. Upon completion of injection administration, the administration completion flag 808 may be changed from False to True. Furthermore, upon completion of injection administration, the administration data 800 may be sent to the patient device 702 and/or the server 704. In some embodiments, the administration data 800 may include a treatment schedule 816. When an injection is missed, the injection device 400 may send the administration data 800 to the patient device 702 and/or the server 704 reflecting a missed injection (e.g., the administration completion flag 808 set to False). In some embodiments, the injection device 400 is configured to send the administration data 800 to the patient device 702 and/or the server 704 indicating an incomplete administration when the administration is started, but not completed. For example, if a load sensor indicated that an injection was not performed, or if a partial administration was injected.

The administration data 800 may include a timestamp 810. The server 704 may use the timestamp 810 to determine the compliance of the injection. The administration data 800 may further include temperature data 812 as detected by the injection device 400. The temperature data 812 may aid in the estimation of degradation of the pharmaceutical below the prescribed potency in the injectable.

In some embodiments, the administration data 800 may include a fraud, waste, and abuse data 818. The fraud, waste, and abuse data 818 may include an analog and/or digital force measurement as detected by a load sensor (described with respect to FIGS. 12A-9C). The server 704 may then determine whether an auto-injection was dispensed into the air (as a fraud, waste, and abuse rather than treatment). In alternative embodiments, the fraud, waste, and abuse data 818 may include a flag corresponding to whether the injection was legitimate or wasteful/fraudulent. In these embodiments, the microprocessor 510 may use the load sensor data to determine the flag. In these embodiments, the load sensor measurements may be compared to a predetermined force threshold, as injections into a patient may cause more resistance and corresponding higher force compared to a wasteful/fraudulent injection to the air. In some embodiments, a change in force (e.g., a delta) may be sensed and/or used to determine the legitimacy of the injection. For example, an intradermal, intravenous, subcutaneous, or intramuscular injection may be detectable by corresponding predetermined force thresholds (ordered by a pre-determined lowest force to highest force threshold).

In some embodiments, after transmission from the injection device 400, the administration data 800 may be used to make one or more of an insurance coverage determination, a medical treatment determination, and a manufacturing determination. The insurance coverage determination may involve receiving of the administration data 800 by an insurance company and making insurance coverage decisions based thereon, such as increasing or lowering insurance rates or claim payouts based upon whether data indicative of a legitimate injection or a fraudulent injection is included in the administration data 800. The medical treatment determination may involve receiving of the administration data 800 by a medical facility and/or one or more medical practitioners. The one or more medical practitioners may make adjustments to the treatment of a patient based on the administration data 800. The manufacturing determination may involve receiving of the administration data 800 by one or more manufacturers, such as a manufacturer of the injection device 400. The one or more manufacturers may make design adjustments, assembly adjustments, factory adjustments, or any other suitable manufacturing determinations based on the administration data 800.

In some embodiments, the injection device 400 may be paired to a modem 710. The modem 710 may be substantially similar to wireless module 504. For example, the modem 710 may be in electronic communication with the patient device 702, server 704, or the internet. The electronic communication connection may occur via ethernet, wireless, Bluetooth, cellular connection, etc. In this manner, the injection device 400 may not necessarily be connected directly to the server 704 or to cellular towers. The injection device 400 may pair to the modem 710 via a modem connection 712. The modem connection 712 may be substantially similar to wireless connection 701. For example, the modem connection 712 may allow electronic communication between the injection device 400 and the modem 710. The modem connection 712 may be wireless or wired, and may be Bluetooth, Bluetooth low energy, cellular, or use any other suitable protocol or means of data transmission. In some embodiments, identifying information, such as the injection device ID 802, the patient ID 804, the potency 806, the drug ID 814, etc., stored on the injection device 400 may be set by the manufacturer, pharmacist, or other providers before receipt by the patient. In some embodiments, the injection device 400 may be set with a modem ID corresponding to the modem 710 of a particular patient for verification of the modem 710 of the patient with the injection device 400 and pharmaceutical contained therein. In some embodiments, a pharmacist or other provider of the injection device 400 may update the patient's modem 710 with identifying information, such as the injection device ID 802, the patient ID 804, the potency 806, the drug ID 814, the temperature data 812, the treatment schedule 816, and/or fraud, waste, and abuse data 818. The identifying information of the injection device 400 may be compared to identifying information on the modem 710. If the identifying information matches, e.g., the patient ID 804 and the drug ID 814 match between the injection device 400 and the modem 710, then the injection device 400 may establish electronic communication with the modem 710 to send the administration data 800 to the server 704 through the modem 710. In this manner, the modem 710 may include a cellular module and the injection device 400 and subsequent reporting injection devices may connect to the modem 710 to send the administration data 800 to the modem 710, which may send the administration data 800 over the cellular connection. In some embodiments, establishing a connection with the modem 710 may also unlock the injection device 400 to allow injection.

Figure 9:
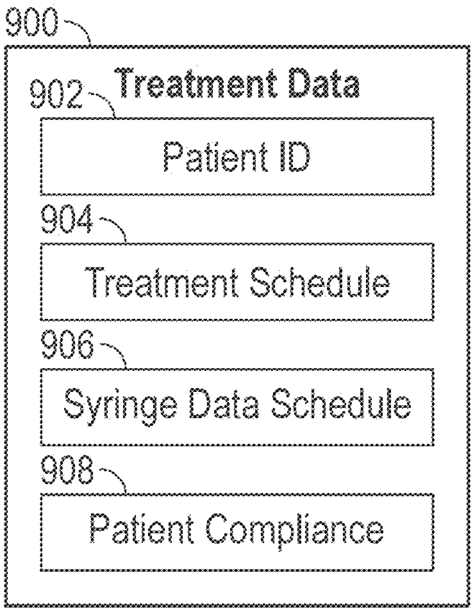
FIG. 9 is a block-level diagram that illustrates treatment data as it can be stored on a server according to some embodiments of the present disclosure.

FIG. 9 illustrates a block-level diagram of treatment data as can be stored on the server 704. The treatment data 900 may be stored, collected, and/or calculated by the server 704. For example, treatment data 900 may correspond to a patient associated with a patient ID 902. A corresponding treatment schedule 904, as prescribed by physician **408*b* may be stored. The treatment schedule 904 may include prescribed potencies and prescribed injection timings. For example, the treatment schedule 904** may include the prescribed pharmaceuticals, corresponding potencies, and prescribed injection regularity (e.g., daily, twice daily, etc.).

In some embodiments, an injection device data schedule 906 may be stored and/or modified by the server 704. The injection device data schedule 906 may include the injection device data history received by the server 704, which corresponds to the patient. For example, the injection device data schedule 906 may include the temperature of the pharmaceutical, the timestamp of administration, the potency, the administration completion flag, the injection device ID, the patient ID, the drug ID, etc.

In some embodiments, patient compliance 908 may be stored and/or calculated by the server 704. The patient compliance 908 may be determined by comparing the treatment schedule 904 to the injection device data schedule 906. If the injection device data schedule 906 is substantially similar with regard to the drug ID, the potency, and the injection timing to the treatment schedule 904, then the patient compliance 908 may be set to reflect patient compliance. Otherwise, the patient compliance 908 may be set to reflect patient non-compliance. In some embodiments, the patient compliance 908 may be stored with regard to the full history of data recorded, by year, by month, by week, and/or by day.

Figure 10:
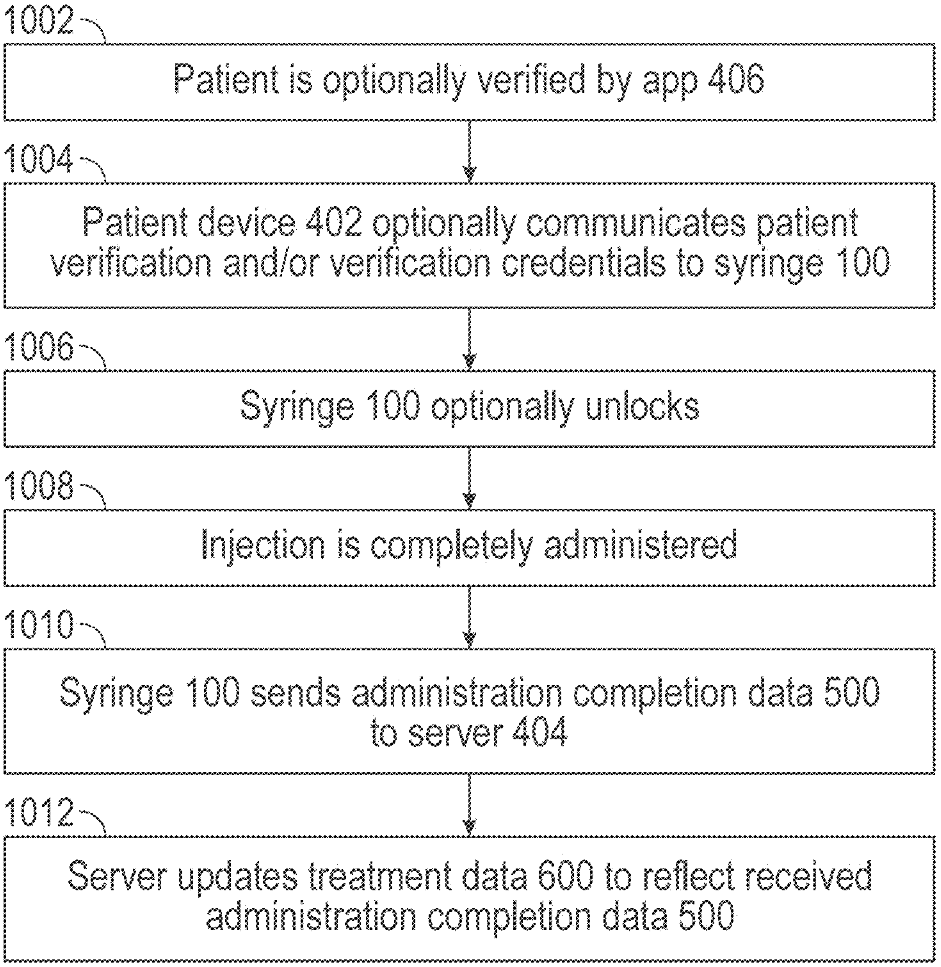
FIG. 10 is a block-level diagram that illustrates sending an administration data to the server according to some embodiments of the present disclosure.

FIG. 10 illustrates a block-level diagram of a method 1000 of sending the administration data 800 to the server 704. In optional step 1002, the patient may be verified by the app 706 on the patient device 702. In some embodiments, the patient device 702 may indicate that the patient is verified and/or may send the patient verification data over the wireless connection 701. The patient may be verified by username, password, patient ID, and/or digital certificate. In some embodiments, the patient may be verified by RSA key, fingerprint by the sensor of the patient device 702, and/or facial recognition by a camera of the patient device 702. In some embodiments, patient verification may include two-factor verification, wherein two methods may be required to satisfy patient verification. For example, the app 706 may include a code or key that corresponds to the patient, but the patient must also provide fingerprint and/or facial verification through the patient device 702.

In optional step 1004, the patient device 702 may communicate patient verification and/or verification credentials to the injection device 400. Later, the injection device 400 may unlock the locking mechanism 512 based on positive patient verification. In some embodiments, the microprocessor 510 may perform verification based on one or more of username, password, patient ID, face verification, retinal verification, vocal verification, fingerprint verification, and/or digital certificate. However, embodiments include receiving an indication of positive patient verification as performed by the app 706, the patient device 702, and/or the server 704.

Upon verification, the injection device 400 may unlock the locking mechanism 512 such that the piston 406 may be compressed to administer the contained pharmaceutical.

In step 1006, the injection device 400 may unlock, allowing for the administration of the drug in the barrel 402. However, in some embodiments, the injection device 400 may be prevented from unlocking according to the patient ID and/or the temperature data, such as when patient identification is not verified or when temperature data indicates that cold chain storage has been broken for the corresponding drug.

In some embodiments, the locking mechanism 512 may be reset from the locked position to the unlocked position in this step. For example, the microprocessor 510 may generate the administration data 800 that can correspond to the current injection upon unlocking the injection device 400. The administration completion flag 808 may be set to False upon beginning administration of the injection. In some embodiments, the administration completion flag 808 may not necessarily be changed until the head 412 is fully compressed to the barrel 402, such that partial injections may be reported. The microprocessor 510 may thus cause the administration data 800 to be sent to the server 704 after a predetermined elapsed time following unlocking the injection device 400 and/or load sensor detection, even if the switch 506 does not indicate that injection has occurred.

In step 1008, the injection may be completely administered to the patient. In this step, the head 412 may be substantially fully compressed when the injection is substantially completely administered. The magnet 414 may be sufficiently proximate to the switch 506 such that the magnetic field may be detected, and an administration completion may be triggered. In some embodiments, a mechanical switch may be pressed to trigger notification of administration completion rather than or in addition to the magnet 414 being sufficiently proximate to the switch 506. In some embodiments, the administration data 800 may be generated upon detection of the magnetic field, wherein the administration completion flag 808 reflects the completed injection. For example, the administration completion flag 808 may be set to True. In some embodiments, administration completion may further trigger step 1010, wherein the injection device 400 may send the administration data 800 to the server 704. In step 1012, the server 704 may update the treatment data 900 to reflect the received administration data 800.

In some embodiments, the method 1000 may be performed with respect to an attachable reporting module.

Figure 11:
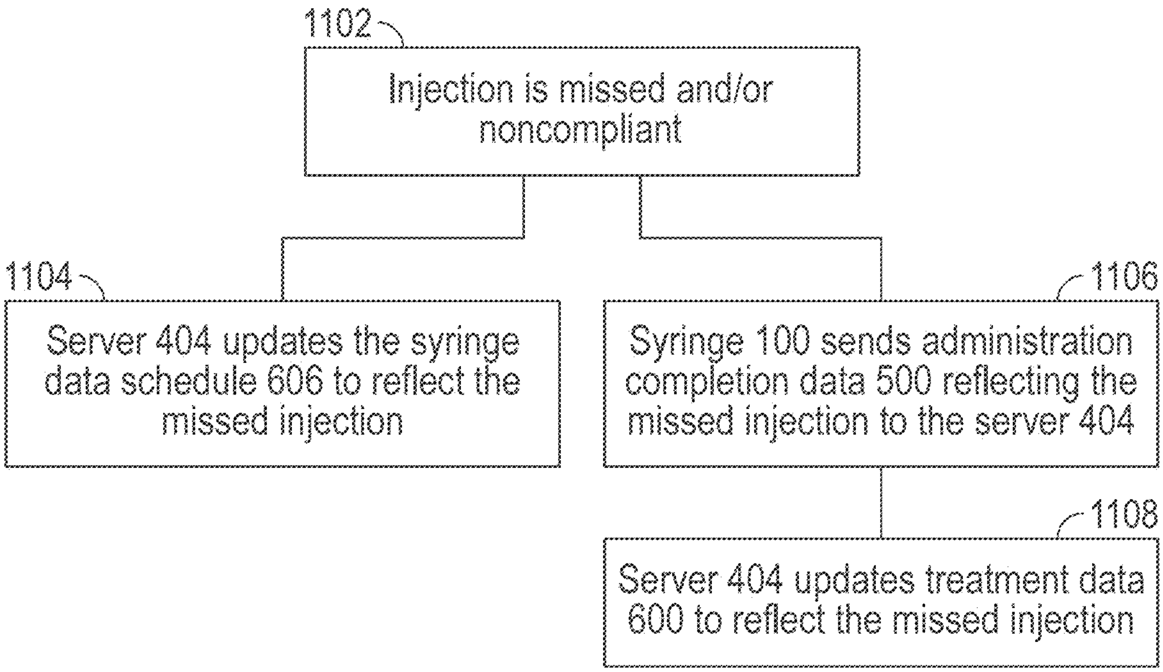
FIG. 11 is a block-level diagram that illustrates recording a missed injection according to some embodiments of the present disclosure.

FIG. 11 illustrates a block-level diagram of a method 1100 of recording a missed injection. In step 1102, an injection may be determined to be missed based on the treatment schedule 816 and/or 904. In some embodiments, the treatment schedule 904 may be stored on the server 704, and the server 704 may automatically update the treatment data 900 to reflect the missed injection 1104. In other embodiments, the treatment schedule 816 may be stored on the injection device 400, and the injection device may send the administration data 800 reflecting the missed injection to the server 704 in step 1106. Step 1106 may further include sending the administration data 800 reflecting an incomplete injection (e.g., administration completion flag 808 set to False) to the server 704 when an injection is non-compliant. A noncompliant injection can include an injection where the administration was started, but not complete. Other non-compliant injections can include ejection of the drug from the injection device 400 without injecting into the patient, such as emptying the injection device 400 into the air. In step 1108, the treatment data 900 may be updated to reflect the missed injection.

In some embodiments, the temperature sensor 502 may be used to record temperatures at a predetermined interval through the life cycle, such as transport, storage, etc., of the pharmaceutical. For example, the temperature sensor 502 could record temperatures daily, hourly, and/or every half-hour. In some instances, the temperature sensor 502 may record irregular temperatures, wherein the irregular temperature is known to risk degradation of the pharmaceutical. This temperature data 812 may be stored on the microprocessor 510 (e.g., the temperature data 812). Upon sending the administration data 800, the sent administration data 800 may include life cycle data, such as the temperature history (e.g., the temperature data 812).

In some embodiments, the temperature data 812 may be used to determine whether the pharmaceutical remains potent and/or safe for injection, and subsequently, whether providers, pharmacists, insurers, and other stakeholders should rely on, use, or pay for that pharmaceutical. The temperature data 812 may include a temperature compliance flag that may be positive when the pharmaceutical remains within a predetermined threshold of temperatures for that pharmaceutical (e.g., cold chain storage), as detected by the temperature sensor 502. The temperature data 812 may include a temperature compliance flag. For example, the temperature compliance flag may default to True and may be changed to False upon detection of a freezing of the pharmaceutical by the temperature sensor 502. The temperature compliance flag may be changed to False upon elevation of the temperature above the predetermined temperature range threshold and/or temperature drop below the predetermined temperature range threshold. In some embodiments, the temperature data 812 and or temperature compliance flag may allow for a time tolerance for exceeding the predetermined temperature range (except that freezing is not allowed in some embodiments). In embodiments containing Humira, Enbrel, or Remicade, the temperature compliance flag may remain True unless the temperature of the drug is detected outside the range of 2 to 8 degrees Celsius. In some embodiments, the temperature compliance flag may not necessarily be changed until extended storage at room temperature is detected. In the embodiments of Humira and Enbrel, the temperature compliance flag may become False when the injection device 400 containing the drug is stored at room temperature for over 14 days. In embodiments having Remicade, the temperature compliance flag may become False when the injection device 400 is stored at room temperature for over 24 hours.

In some embodiments, the predetermined temperature range thresholds may correspond to the particular pharmaceutical in the corresponding injection device 400. The predetermined temperature range thresholds may be set by a manufacturer, the pharmacist, an insurance provider, and/or a health care provider.

In some embodiments, the injection device 400 may include a temperature safety feature to prevent the injection of degraded pharmaceuticals. For example, the locking mechanisms 512 may remain locked after the temperature compliance flag of the temperature data 812 becomes False, regardless of verification of patient identification.

In some embodiments, the microprocessor 510 may be configured to calculate a degradation risk correlating to the pharmaceutical. In these embodiments, if the degradation risk is above a predetermined threshold, then the locking mechanism 512 may prevent injection, even if the other criteria, such as patient verification, are satisfied. In some embodiments, the microprocessor 510 may include a timing circuit configured to calculate the degradation risk. In some embodiments, the timing circuit may be used with the temperature sensor 502 to detect when the injection device 400 and/or pharmaceutical is removed from temperature-controlled storage. The timing circuit may be used to ensure that the injection is made before a predetermined elapsed time. In these instances, the locking mechanism 512 may prevent injection after the predetermined clapsed time from removal from storage, even if the other criteria are satisfied.

In some embodiments, the injection device 400 may be a multi-use system, such that the injection device may be reusable and/or the reporting components 416 may be reusable. In these embodiments, the needle 404 may be replaceable and the reporting components 416 and/or the administration data 800 may be reset upon changing the needle 404. Furthermore, the reporting components 416 and/or the administration data 800 may be reset upon snap-fit of the reporting components 416 to a new injection device 400. Resetting the reporting components 416 and/or the administration data 800 may be triggered by a mechanical switch, such as when the mechanical switch is closed or opened. Changing the needle 404 and/or snap fitting the reporting components 416 to the injection device 400 may trigger the mechanical switch. However, many biologics may be provided as prefilled injection devices 400 intended for single-use administration. In these embodiments, the needle 404 may not necessarily be changed.

In some embodiments, the method 1100 may be performed with respect to an attachable reporting module.

Figure 12A:
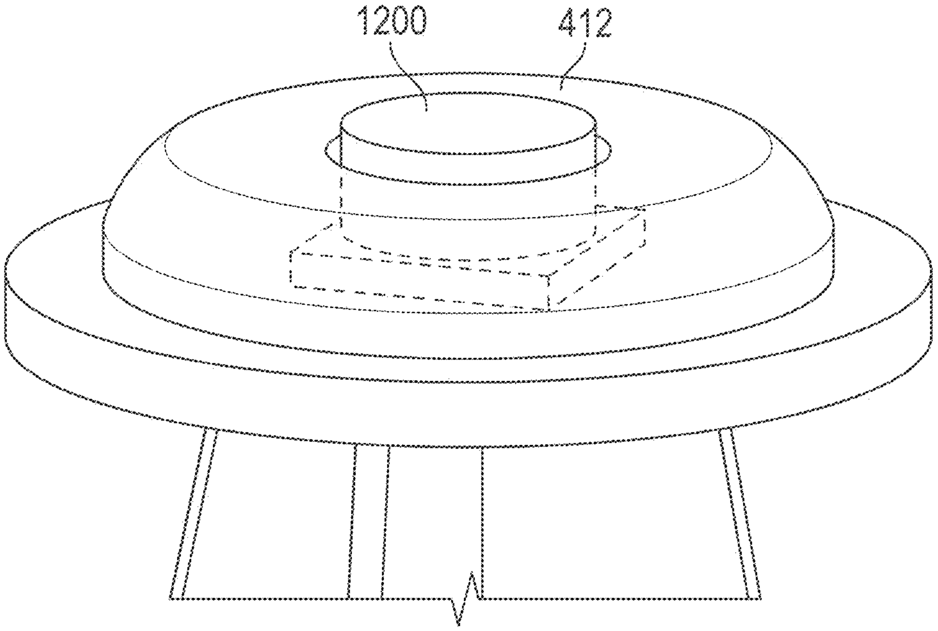
FIG. 12A is a diagram that illustrates a head of the reporting injection device comprising a load sensor according to some embodiments of the present disclosure.
Figure 12B:
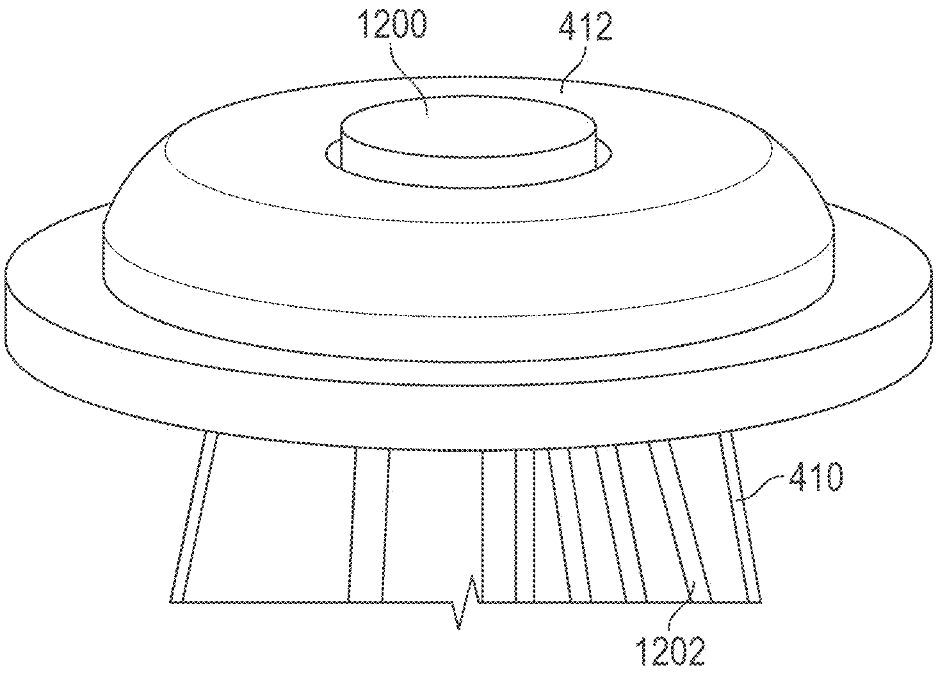
FIG. 12B is a diagram that illustrates a conductor of the reporting injection device according to some embodiments of the present disclosure.
Figure 12C:
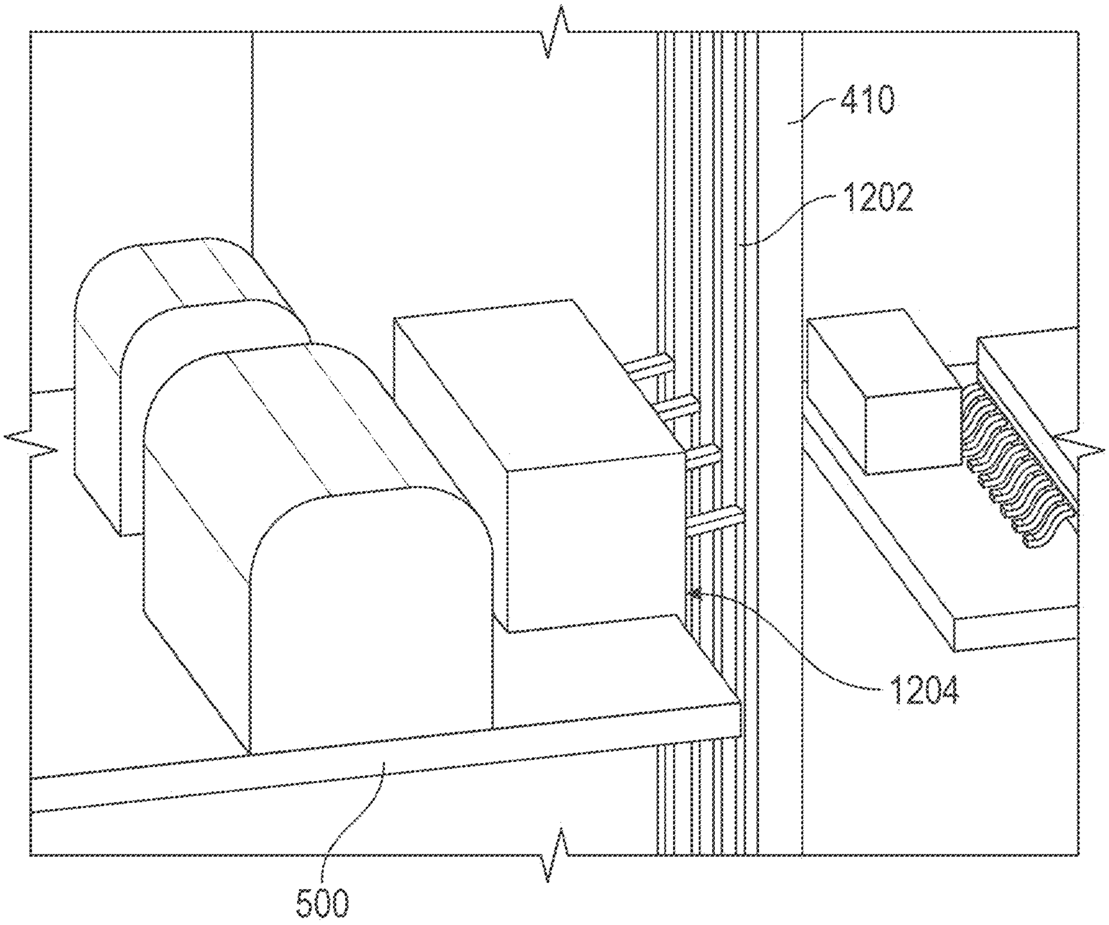
FIG. 12C is a diagram that illustrates the interaction of a stalk of the reporting injection device and a load sensor receiver according to some embodiments of the present disclosure.

FIGS. 12A-12C illustrate embodiments of the injection device 400 including a load sensor. The load sensor may be positioned on the needle proximate the barrel 402. In some embodiments, the load sensor may be positioned within the barrel 402 such that a pressure gradient in the injection device may be detected. The load sensor may be in electronic communication with the microprocessor 510 such that the load sensor may send detected pressure to the microprocessor 510. The microprocessor 510 may record and/or send the pressure data with the administration data 800. The load sensor may detect, for example, subcutaneous applied pressure, such as to determine that an intermuscular injection is occurring. In some embodiments, the locking mechanism 512 may lock in response to an absence of appropriate pressure detection by the load sensor, thereby preventing injection. In some embodiments, the injection may be allowed, by the locking mechanism 512 being unlocked, but administration data 800 may include a pressure data reflecting improper pressure detected. In some embodiments, the administration data 800 includes pressure data from the load sensor, regardless of whether appropriate pressure has been detected.

FIG. 12A illustrates embodiments of the injection device 400 wherein the head 412 of the injection device 400 comprises a load sensor 1200. In some embodiments, the load sensor 1200 may be present with the magnet 414. The load sensor 1200 may include a force sensor. For example, some force sensors include a force-sensing resistor that includes a material that changes resistance when a force, pressure, or mechanical stress is applied. Such materials may include a conductive polymer. The changes in resistance may be interpolated to correspond to the force applied, such that the force applied to inject the drug from the barrel 402 can be measured. The measured force may be higher when injecting into a patient, such as an intermuscular injection, rather than dispensing the drug through the needle without injection. By way of example, the additional force may result from mechanical resistance of the body of the patient to the injection compared to the relatively lower resistance when dispensing the drug into the air.

In some embodiments, a predetermined force threshold may be used to determine whether dispensing the drug resulted in a compliant injection or a noncompliant fraud, waste, and abuse. For example, a measured force greater than the predetermined force threshold may correspond to a compliant administration of the drug. Furthermore, measured force less than the predetermined threshold may correspond to a wasteful or fraudulent occurrence, such as dispensing the drug into a sink.

Example force sensors may include the Honeywell FSA series, FSG series, FSS series, TBF series, or 1865 series. For example, the load sensor 1200 may be able to measure from about 1 bar to about 10 bar, about 400 kPa to about 1 MPa, or about 15 psi to about 450 psi in pressure. The load sensor 1200 may include millivolt analog output. Alternative embodiments may include other load cells that may be electronically read by the microprocessor.

FIG. 12B illustrates embodiments of the injection device 400 including a conductor 1202. The load sensor 1200 may be in electrical and/or electronic communication with the conductor 1202. The conductor 1202 may include one or more electrically conductive traces and/or wires that run the length of the stalk 410 such that the conductor 1202 may remain in electrical communication with the circuit board 500 during the injection. In some embodiments, the conductor 1202 may allow the load sensor 1200 to be in electrical communication with the circuit board 500 and/or the microprocessor 510 before, during, and/or after the injection. In some embodiments, the load sensor 1200 provides an analog output, the output can be relayed to the microprocessor for comparison to the predetermined force threshold or converted to digital measurement and comparison to the predetermined threshold.

FIG. 12C illustrates embodiments of the reporting injection device 400 wherein the stalk 410 includes a load sensor receiver 1204. In some embodiments, the load sensor receiver 1204 may be in electrical communication with the conductor 1202 and/or the circuit board 500. In this manner, the load sensor receiver 1204 may relay electrical and/or electronic signals and/or information from the conductor 1202 to the microprocessor 510. In some embodiments, the load sensor receiver 1204 may convert analog signals to digital signals. In some embodiments, the load sensor that may convert the analog signal to digital, and the load sensor receiver 1204 may relay the digital signal to the microprocessor 510. In some embodiments, the load sensor receiver 1204 may relay the analog signal to the microprocessor 510 for conversion by the microprocessor 510, in embodiments wherein conversion is performed before comparison to the predetermined force threshold.

In some embodiments, the injection device 400 may include an automatic injection system in communication with the microprocessor 510. The automatic injection system may facilitate the automatic injection of one or more doses of a pharmaceutical from the injection device 400. The automatic injection system may facilitate automatic injection of the one or more doses at one or more of a specific injection rate, at a specified injection depth, and at a predetermined injectable temperature, the rate, depth, and temperature being measured by one or more of the sensors of the injection device 400, including the temperature sensor 502 and/or the load sensor. In some embodiments, the automatic injection system may be configured to facilitate the delivery of the dose by the injection device 400 according to an injection program among a library of injection programs stored in the microprocessor 510 or associated memory. In some embodiments, the automatic injection system may include a withdrawal mechanism, the withdrawal mechanism being configured to facilitate automatic withdrawal of the needle 404 from an injection site. In some embodiments, the automatic injection system may facilitate the delivery of the dose based on a prescribed profile for the recipient of the dose.

Figure 13A:
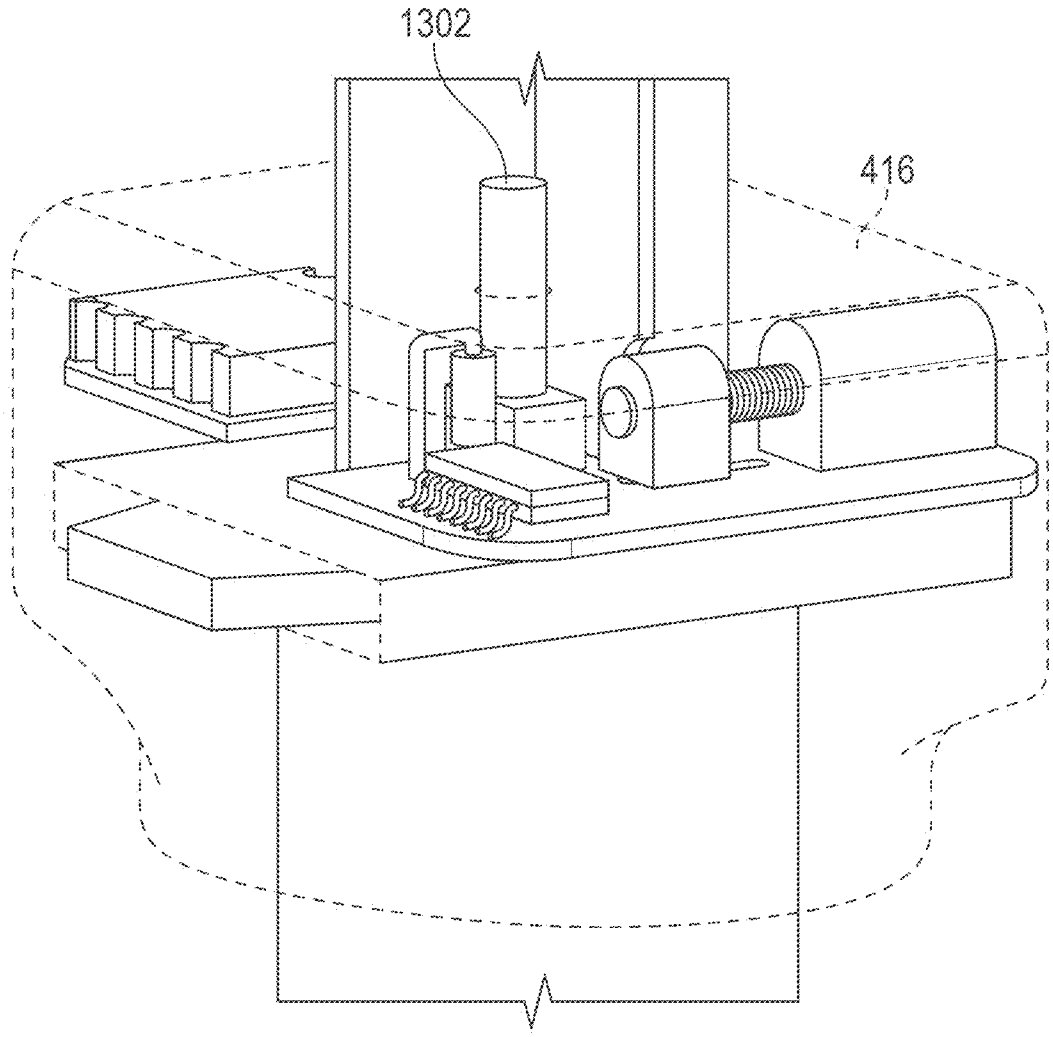
FIG. 13A is a diagram that illustrates a mechanical switch of the injection device according to some embodiments of the present disclosure.

FIG. 13A illustrates embodiments of the injection device 400 including a mechanical switch 1302. In some embodiments, the mechanical switch 1302 may replace the switch 506. The mechanical switch 1302 may be in electrical communication with the reporting components 416 such that the administration data 800 may be sent upon pressing the mechanical switch 1302. The mechanical switch 1302 may include a resistance spring. The mechanical switch 1302 may further include a circuit. Upon pressing the mechanical switch 1302, the circuit may become opened or closed. The change in the state of the circuit of the mechanical switch 1302 may trigger alteration and/or sending of the administration data 800.

Figure 13B:
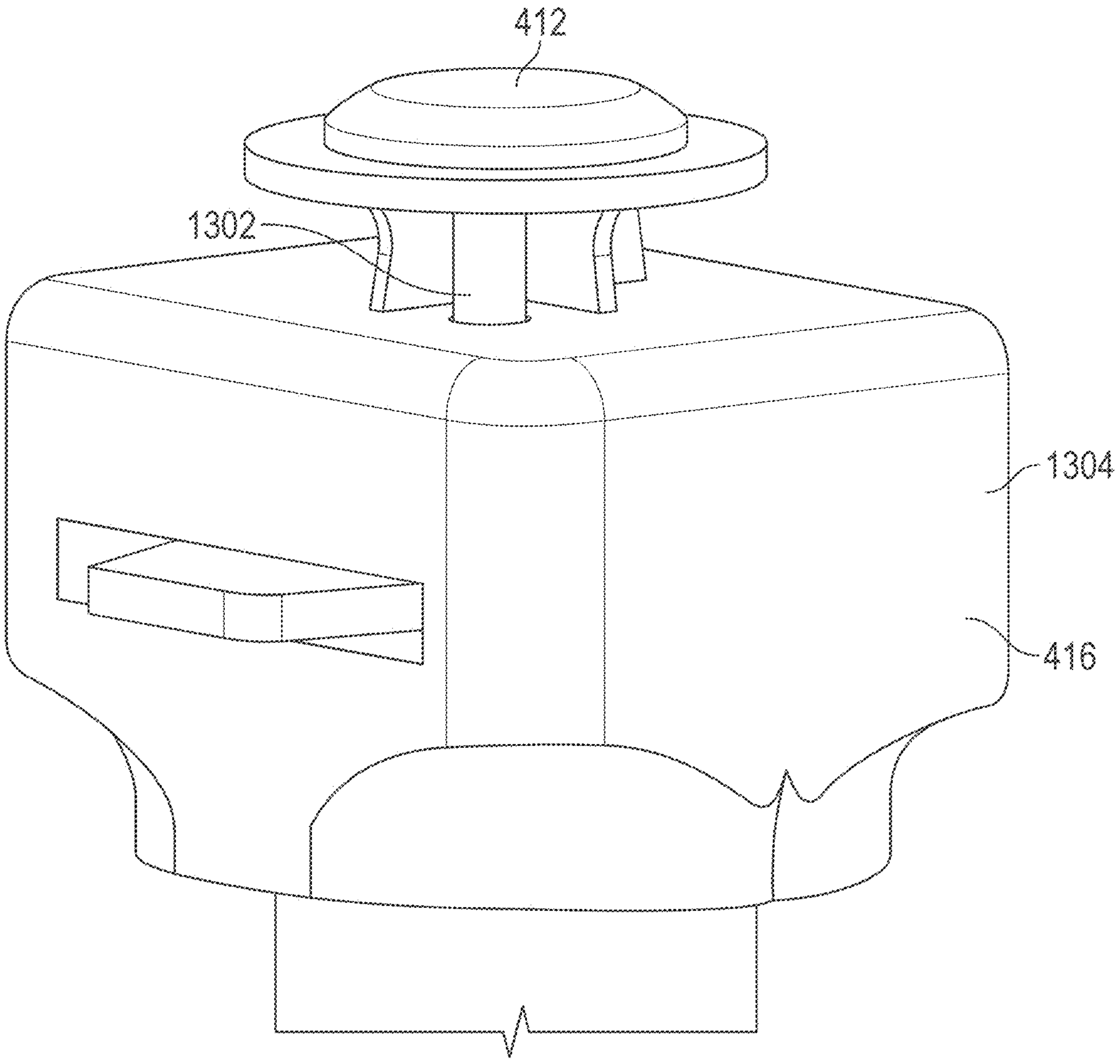
FIG. 13B is a diagram that illustrates an alternative view of the mechanical switch according to some embodiments of the present disclosure.

FIG. 13B illustrates embodiments of the injection device 400 including the mechanical switch 1302. The mechanical switch 1302 may extend beyond a housing 1304 of the reporting components 416. In some embodiments, the head 412 may not include the magnet 414. Rather, the head 412 may press the mechanical switch 1302 upon injection completion (e.g., when the head 412 is pressed to the housing 1304).

Figure 13C:
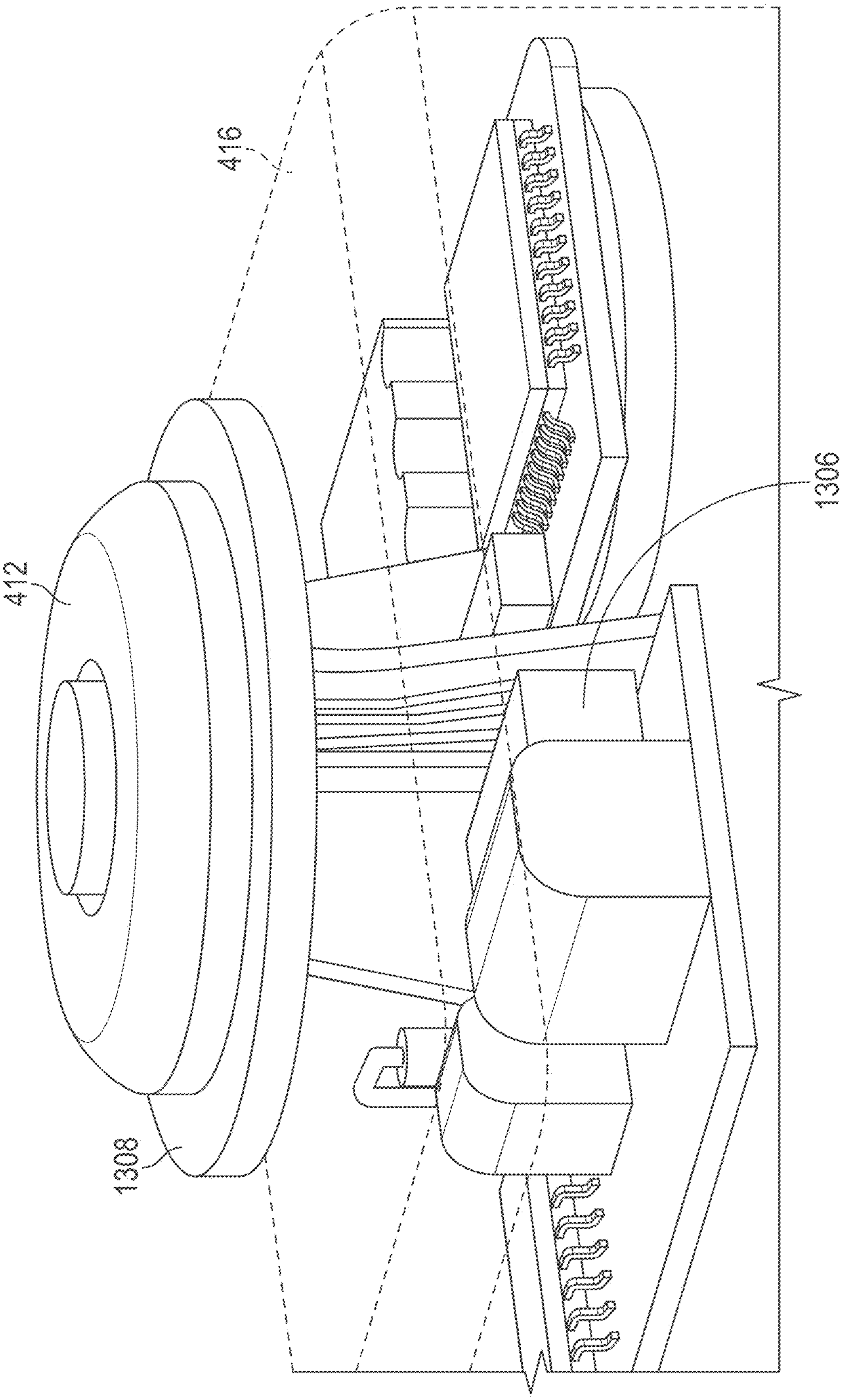
FIG. 13C is a diagram that illustrates another alternative view of the mechanical switch according to some embodiments of the present disclosure.

FIG. 13C illustrates embodiments of the injection device 400 including the mechanical switch 1302. The head 412 may include a stamping 1308 that may press the mechanical switch 1302 when fully pressed. The mechanical switch 1302 may include a mechanical switch contact 1306 that may be in electrical and/or electronic communication with the reporting components 416. Upon pressing the mechanical switch 1302, the reporting components 416 may generate or alter the administration data 800. Upon pressing the mechanical switch 1302, the reporting components 416 may send the administration data 800.

Figure 14A:
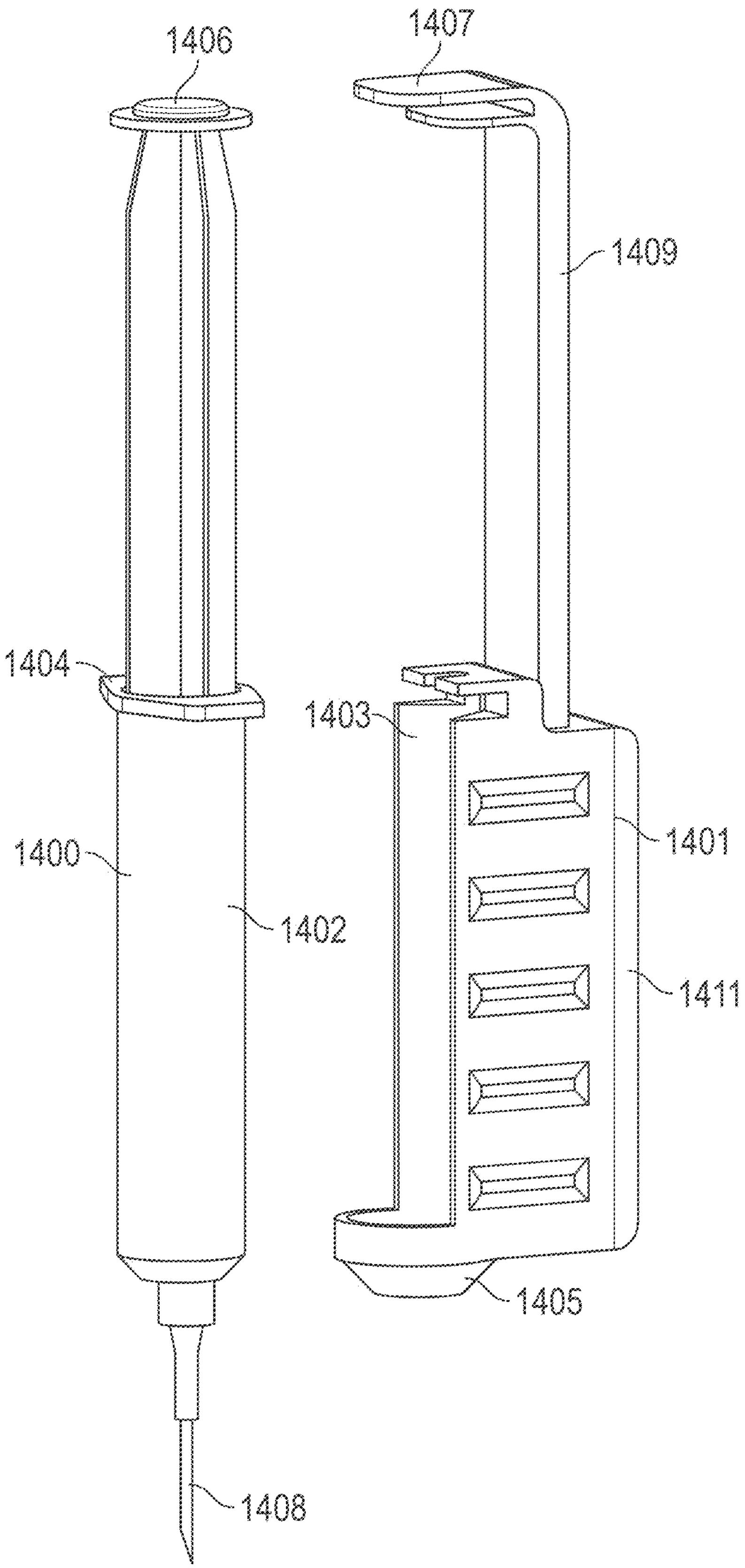
FIG. 14A is a diagram that illustrates an attachable reporting module according to some embodiments of the present disclosure.

FIG. 14A illustrates embodiments of the injection device 400 including an attachable reporting module 1401. The reporting module 1401 may be attachable and/or detachable from a standard injection device 1400. For example, the reporting module 1401 may include a barrel receiver 1405, a grip receiver 1403, and/or a head receiver 1407. The reporting module 1401 may further include a slide 1409 such that the head receiver 1407 may be pressed with a head 1406 of the standard injection device 1400. These structures may allow the reporting module 1401 to be attached to the standard injection device 1400 by frictional engagement. For example, a barrel 1402 of the standard injection device 1400 may be received in the barrel receiver 1405. The barrel receiver 1405 may include a conical or frusto-conical shape configured to receive and/or frictionally engaged the barrel 1402 proximate a needle 1408.

In some embodiments, the grip receiver 1403 may be configured to receive and/or frictionally engage a grip 1404 of the needle 1408. The grip receiver 1403 may be positioned the length of the barrel 1402 from the barrel receiver 1405. The grip 1404 may include flat flanges extending orthogonally from an end of the barrel 1402. The grip receiver 1403 may include a first support and a second support set apart at a sufficient distance to frictionally engage the flanges of the grip 1404 when inserted.

In some embodiments, the head receiver 1407 may be in slidable communication with a base 1411 of the reporting module 1401 via slide 1409 such that the head receiver 1407 may rest against and/or frictionally engage the head 1406 such that pressing the head receiver 1407 may press the head 1406 thereby administering an injection. The head receiver 1407 may include a single projection orthogonal to the slide 1409. Alternative embodiments include a first projection and a second projection. The first projection and second projection may be spaced apart such that the first projection may engage a distal side of the head 1406. The second projection may be distance sufficiently to engage a proximate side of the head 1406. In some embodiments, the second projection may frictionally fit against a feature, such as a stamping of the head 1406.

Figure 14B:
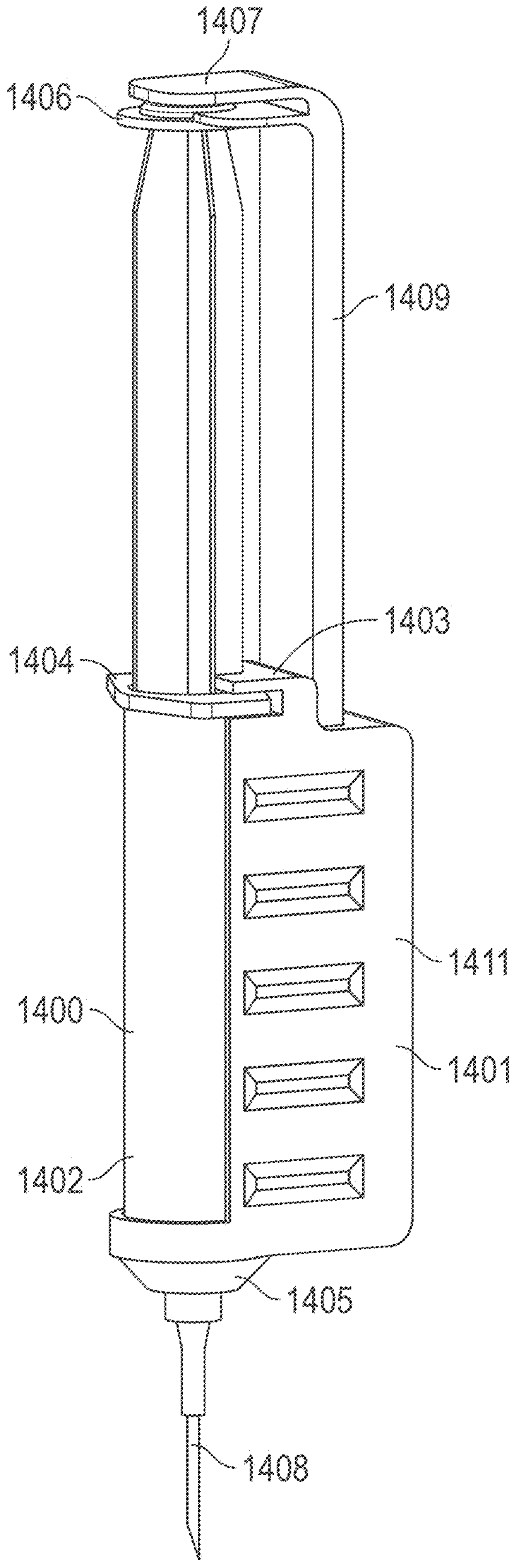
FIG. 14B is a diagram that illustrates the reporting module attached to a standard injection device according to some embodiments of the present disclosure.
Figure 14C:
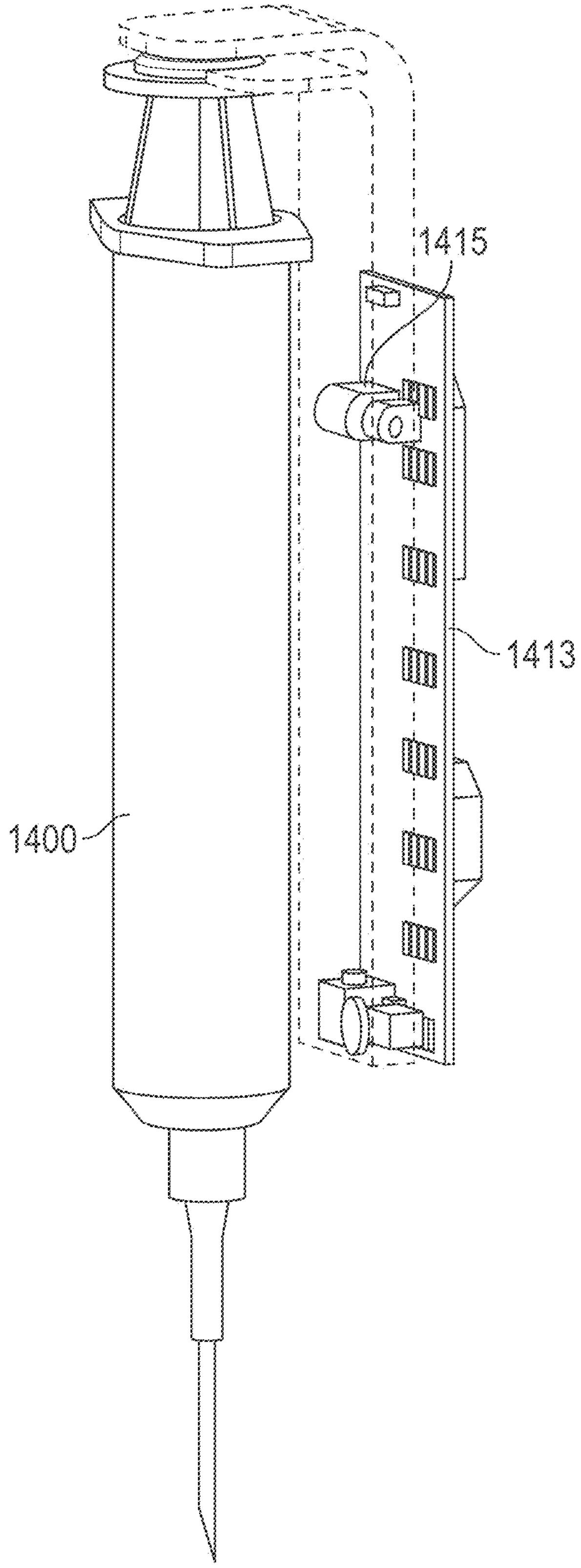
FIG. 14C is a diagram that illustrates the reporting components of the reporting module according to some embodiments of the present disclosure.

FIGS. 14B-14C illustrate embodiments wherein the reporting module 1401 is attached to a standard injection device 1400. The standard injection device 1400 may be frictionally engaged with the reporting module 1401. In some embodiments, the second projection of the head receiver 1407 may frictionally engage one or more features of a head 1406 of the standard injection device 1400, such as the stamping.

FIG. 14D-14G illustrate embodiments of the reporting components 1413 of the reporting module 1401. In some embodiments, the reporting components 1413 may be substantially similar to the reporting components 416. For example, the reporting components 1413 may include one or more of a temperature sensor, a wireless module, a switch, a battery, a microprocessor, a locking mechanism, etc. In some embodiments, the components may be in electrical and/or electronic communication with one another, such as via a circuit board. For example, locking mechanism 1415 may include a mortise formed in the slide 1409 that may receive a tenon of the locking mechanism 1415 to prevent injection when the reporting module 1401 is engaged to the standard injection device 1400.

Figure 14D:
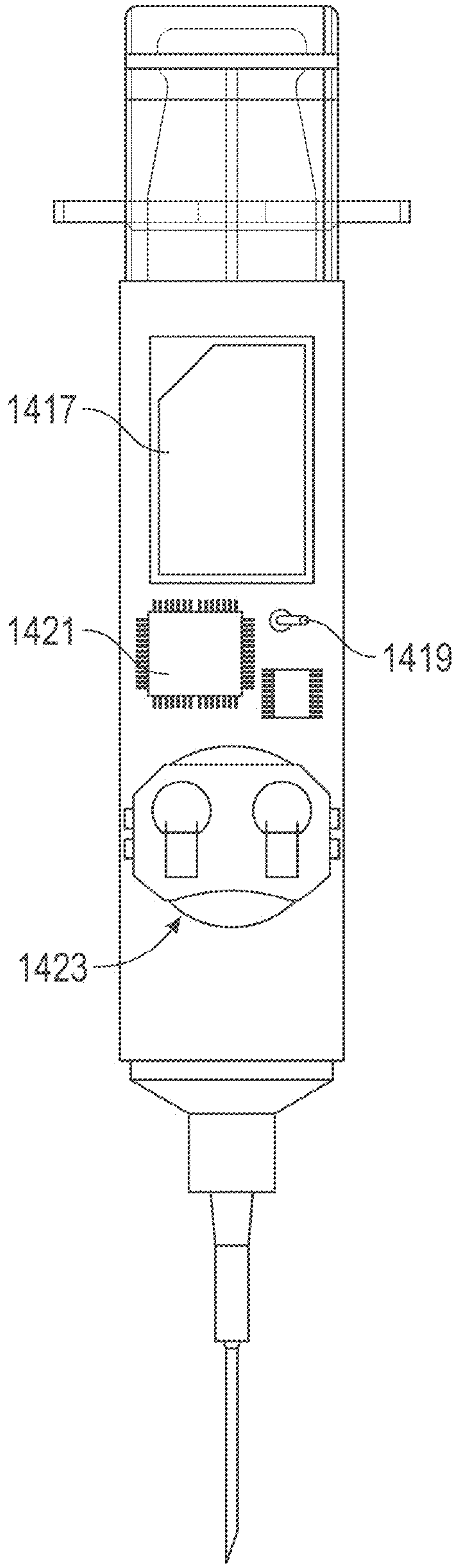
FIG. 14D is a diagram that illustrates an alternative view of the reporting components according to some embodiments of the present disclosure.
Figure 14E:
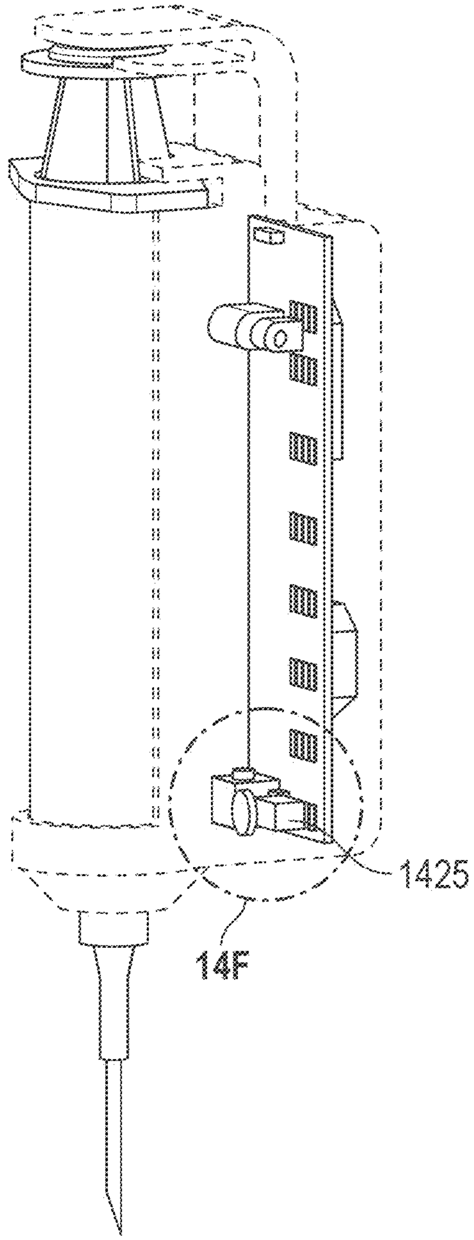
FIG. 14E is a diagram that illustrates an internal view of the reporting components according to some embodiments of the present disclosure.

With reference to FIG. 14D, in some embodiments, the reporting components 1413 may include a wireless module 1417, a temperature sensor 1419, a microprocessor 1421, and/or a battery 1423. The wireless module 1417, the temperature sensor 1419, the microprocessor 1421, and/or the battery 1423 may be substantially similar to the corresponding components of the reporting injection device 400. In some embodiments, the reporting components 1413 may include a switch 1425. The switch 1425 may include any structure sufficient for generating an electrical signal to the processor upon triggering the switch 1425. The switch 1425 may be a mechanical switch that is substantially similar to mechanical switch 1302. In other embodiments, the switch 1425 may be an electronic switch that is substantially similar to switch 506. In some embodiments, the switch 506 may be the mechanical switch 1302. In embodiments wherein the switch 1425 includes a Reed switch, the slide 1409 may include a magnet positioned to trigger the switch 1425 when fully pressed.

Figure 14F:
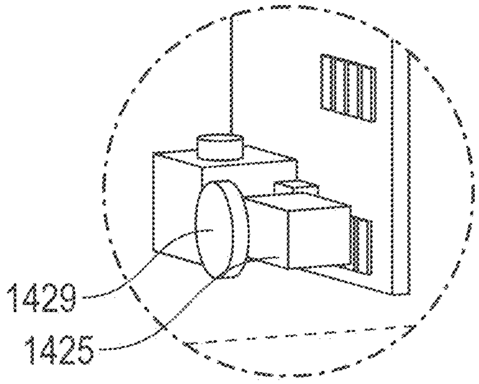
FIG. 14F is a diagram that illustrates a zoomed-in partial view of the reporting components according to some embodiments of the present disclosure.
Figure 14G:
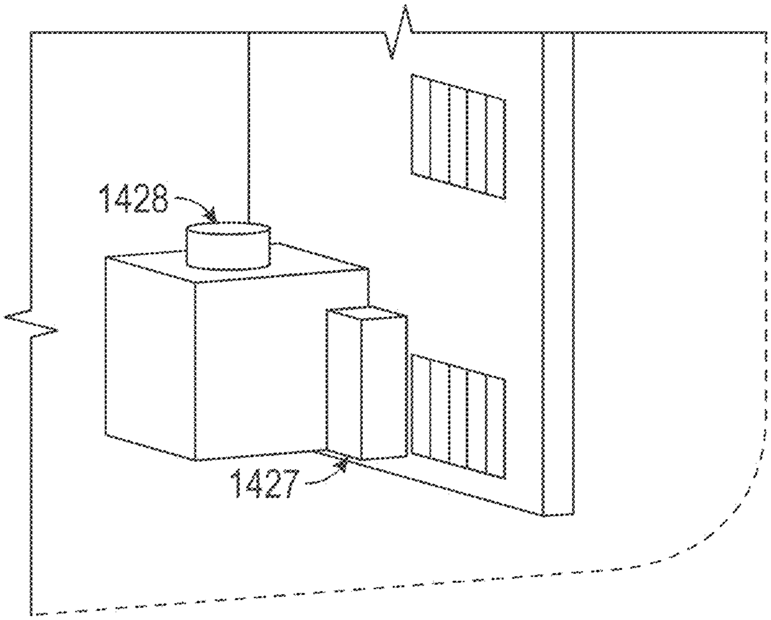
FIG. 14G is a diagram that illustrates an alternate zoomed-in partial view of the reporting components according to some embodiments of the present disclosure.

With reference to FIG. 14F, in some embodiments, the switch 1425 may include a Reed switch 1427 and a magnet 1429. The magnet 1429 may induce a magnetic field to trigger the Reed switch 1427 when the slide 1409 is compressed. The switch 1425 may include a microswitch 1428. The microswitch 1428 may include a miniature snap-action switch. The microswitch may include an electric switch that may be actuated by relatively low physical force, such as through the use of a tipping-point mechanism or an "over-center" mechanism.

Figure 14H:
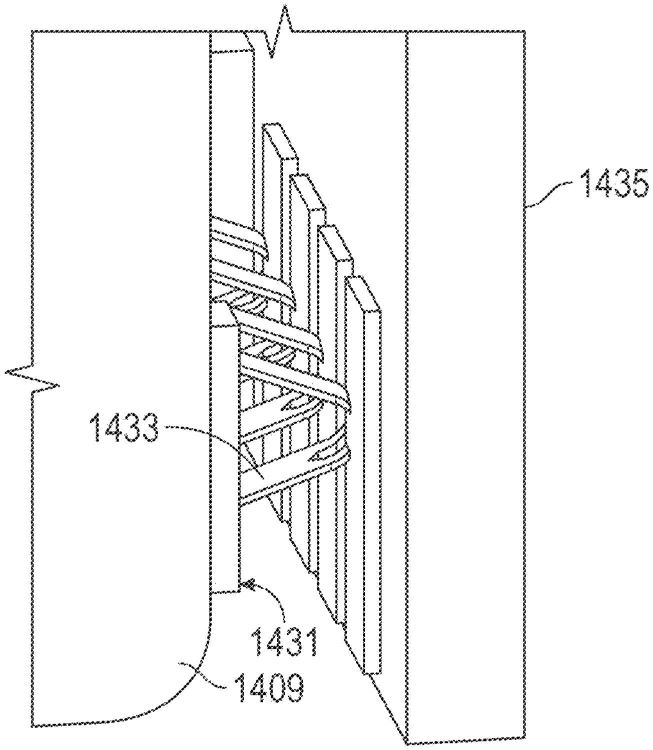
FIG. 14H is a diagram that illustrates a mechanical switch with a spring-loaded printed circuit board that may be pressed to open or close to trigger generation and/or sending administration data from the reporting components according to some embodiments of the present disclosure.

With reference to FIG. 14H, in some embodiments, the switch 1425 may include a mechanical switch 1431. The mechanical switch 1431 may include one or more spring-loaded PCB (printed circuit board) contacts. When the slide 1409 (also FIGS. 14A and 14B) is compressed, the spring-loaded PCB contacts 1433 may be pressed to open or close a circuit. The action of the spring-loaded PCB contacts may trigger generation and/or sending the administration data 800. A circuit board 1435 of the reporting components 1413 may include pressure-sensitive spring-loaded PCB contacts. In some embodiments, the circuit board 1435 may simply include contacts and the slide 1409 may include the spring-loaded contacts that provide electrical communication to trigger generating and/or sending the administration data 800 when the spring-loaded contacts are aligned with the circuit board contacts.

In some embodiments, the switch 1425, such as the spring-loaded PCB contacts, may reset the administration data 800. In this manner, the spring-loaded PCB or other mechanical switches may be pressed when attaching the reporting module 1401 to the standard injection device 1400 illustrated in FIGS. 14E and 14F.

Detailed embodiments of the present disclosure are disclosed herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 15:
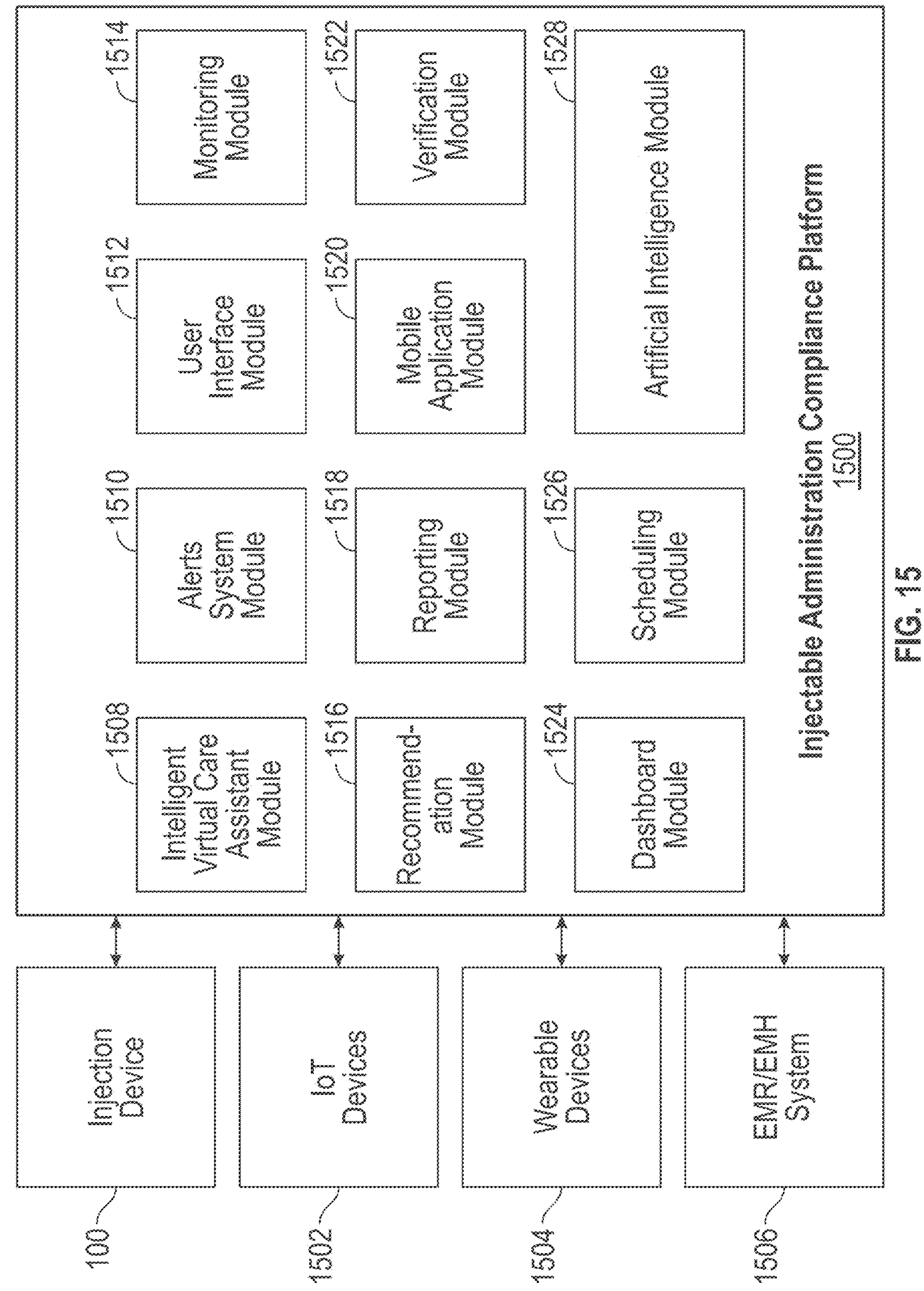
FIG. 15 is a block diagram that illustrates an injectable administration compliance management platform according to some embodiments of the present disclosure.

FIG. 15 illustrates embodiments of an injectable administration compliance management platform 1500. In some embodiments, the injection device 400 may be configured to transmit the administration data 800 to the injectable administration compliance management platform 1500. The management platform 1500 may be a software-based system and/or and Internet of Things (IoT)-based system and may be implemented in the server 704, may be cloud-based, may be a distributed system at least partially implemented in the microprocessor 510 of the injection device 400 and/or in a wearable device, or in any other suitable implementation. The management platform 1500 may be configured for real-time monitoring and management of adherence to an injectable administration plan. The management platform 1500 may receive data collected by one or more IoT devices 1502, one or more wearable devices 1504, one or more emergency medical record (EMR) and/or emergency health record (EHR) systems 1506. The one or more IoT devices may each include a camera, a wearable device, or a combination thereof. In some embodiments, the management platform 1500 may use one or more of the administration data 800, the IoT device data, the wearable device data, and data from the one or more EMR/EHR systems 1506 to make one or more of medical determinations, insurance coverage determinations, and manufacturing determinations. For example, one or more of the wearable devices 1504 and/or the IoT devices 1502 may record eating and/or sleeping data of a wearer of the one or more wearable devices 1504 and/or the IoT devices 1502 and transmit the recorded data to the management platform 1500. The management platform 1500 may automatically determine to change dosage, timing, or other attributes of injection by the wearer based on the recorded data and/or history thereof and transmit such determinations to the wearer.

In some embodiments, the management platform 1500 may be integrated with an EMR and/or EHR system 1506. Upon receipt of the administration data 800, the management platform 1500 may automatically populate one or more fields of the EMR and/or EHR system 1506 with some or all of the administration data 800.

In some embodiments, the management platform 1500 may include an intelligent virtual care assistant module 1508. The intelligent virtual care assistant module 1508 may be configured to perform tasks or services for a user or patient. In some embodiments, the tasks or services may be performed based on user commands. The tasks or services may be performed based on a plan specified by at least one of a physician, a physician's assistant (PA), a health care worker, and a caregiver. The intelligent virtual care assistant module 1508 may be configured to deliver alerts related to health, biometrics, medications, and/or injections, such as by delivering alerts via the wearable device 1504. For example, the intelligent virtual care assistant module 1508 may receive data indicative of an injection schedule according to which a patient should self-administer a drug via the injection device 400. At one or more times specified via the data indicative of the injection schedule, the intelligent virtual care assistant module may output an alert signal to the wearable device 1504. The wearable device 1504 can be configured to display an alert to the patient indicating that a self-injection via the injection device 400 is due according to the injection schedule. In some embodiments, the intelligent virtual care assistant module 1508 may be configured to provide a visual and/or an audible output, use an augmented reality system, use a virtual reality system, and/or be activated using a wake-word. For example, the intelligent virtual care assistant module 1508 may be configured to send a signal to a pair of smart glasses being worn by a patient, thereby causing the smart glasses to display an alert visible to a patient, display biometrics or other information to the patient such as via a chart, display an injection site to the patient, and/or display any other suitable two-dimensional or augmented reality information to the patient.

In some embodiments, the management platform 1500 may include an alerts module 1510. The alerts module 1510 may be configured to provide alerts to a patient and/or a user of the injection device 400. The alerts module 1510 may be configurable by the user and/or a health care provider. The alerts module 1510 may be automatically configured based on a prescribed injectable administration plan for the patient and/or user.

In some embodiments, the management platform 1500 may include a user interface module 1512 for controlling and/or configuring a user interface. The user interface module 1512 may be configurable by a patient, e.g., a user of the injection device 400. In some embodiments, the user interface module 1512 may be configured to automatically populate the user interface based on data from the injection device 400, such as the administration data 800 and/or a profile of the patient or other data collected from the patient, such as by the wearable. In some embodiments, the user interface module 1512 may be configured to receive data from the intelligent virtual care assistant module 1508 and configure and/or populate the user interface based on the data received. For example, the intelligent virtual care assistant module 1508 may send data indicative of a scheduled injection to the user interface module 1512, such as data indicating that an injection is due according to an injection schedule. In response to receiving the data, the user interface module 1512 may configure a user interface of the wearable device 1504 such that the user interface of the wearable device 1504 indicates to a patient that the injection is due.

In some embodiments, the management platform 1500 may include a monitoring and compliance module 1514 for monitoring user compliance. The monitoring and compliance module 1514 may distribute monitoring data to one or more of a set of health care providers, a set of health care payors, and a set of family members.

In some embodiments, the management platform 1500 includes a recommendation module 1516 for generating user recommendations. The recommendation module 1516 may generate recommendations based on one or more of a patient profile and a health care plan for a patient. The recommendation module 1516 may generate recommendations based at least in part on one or more similarities between a patient and a set of other patients.

In some embodiments, the management platform 1500 may include a reporting module 1518 for generating reports. The reporting module 1518 may automatically distribute reports to at least one of a patient, a health care worker, a manufacturer, and a health care payor. The reporting module 1518 may be configured based on at least one of a patient profile and a prescribed health care plan for the patient. In some embodiments, the reporting module 1518 may be configured to facilitate management of health care documentation by patients, health care workers, manufacturers, and/or payors, such as by facilitating electronic filling and/or signing of documentation, facilitating patient privacy, such as HIPAA compliance regarding healthcare documentation, allowing patients and family members to indicate opt-in or opt-out choices and/or other choices regarding treatment options, and managing and/or facilitating any other suitable aspect of health care documentation.

In some embodiments, the management platform 1500 may include a mobile application module 1520 for configuring, controlling, and/or transmitting data to and from a mobile application. The mobile application may be configured to communicate with the injection device 400 and/or the microprocessor 510. The mobile application may be configured based on at least one of a patient profile and a prescribed health care plan for the patient, i.e., the user of the mobile application.

In some embodiments, the management platform 1500 may include a user verification module 1522 for verifying the identity and proper control by users. The locking mechanism 512 may be configured to remain locked until the user is verified via the user verification module 1522. In some embodiments, the user may be verified via the mobile application. In some embodiments, the user may be verified by one or more biometric indicators, such as facial recognition, fingerprint recognition, DNA matching, vein pattern recognition, voice recognition, or recognition via any other suitable biometric. For example, the user verification module 1522 may be configured to send an unlock signal to the locking mechanism 512 in response to matching a fingerprint of a user attempting to administer injection with a stored fingerprint of a verified user. In some embodiments, the verification system may include verification by two-factor authentication, such as requiring that a user attempting to administer rejection meet two or more requirements of inputting a password or PIN, such as via a smartphone or the wearable device 1504, matching one or more biometric indicators of a verified user, and/or any other suitable method of verifying a user attempting to use the injection device 400.

In some embodiments, the management platform 1500 may include a dashboard configured to provide visual information related to injection administration compliance and a dashboard module 1524 for configuring and/or controlling the dashboard. The dashboard may be configured based on one or both of a patient profile and a prescribed health care plan for a patient. The dashboard may be automatically populated with data from the injection device 400, such as the administration data 800. The dashboard may be configured to provide one or more alerts based on one or more events detected by the injection device 400, such as injection, fraud, pharmaceutical degradation, etc.

In some embodiments, the management platform 1500 may include a scheduling module 1526 for scheduling user actions related to injection administration. The scheduling module 1526 may be configured based on one or more of a patient profile, a profile for a specified injectable item, and a prescribed health care plan for a patient. The scheduling module 1526 may be configured based on events collected from the injection device 400.

In some embodiments, the management platform 1500 may include an artificial intelligence module 1528 capable of providing many machine learning, deep learning, and various artificial intelligence services. The artificial intelligence module 1528 may be configured to learn on a training set of data to train to determine and/or optimize the scheduling of future actions of a user, such as injection administration, medication intake, and/or general wellness habits. The artificial intelligence module 1528 may be configured based on one or more of a patient profile, a profile for a specific pharmaceutical, a profile for the injection device 400, and a prescribed health care plan for a patient.

In some embodiments, the artificial intelligence module 1528 may be configured and/or trained to determine that a detected user behavior may negatively impact a user's wellness or injection program. The artificial intelligence module 1528 may be configured to generate an alert to warn the user about the detected behavior. In some embodiments, the alerts module 1510 may be configured based on user behavior detected by the artificial intelligence module 1528 to deliver alerts based thereon.

In some embodiments, the artificial intelligence module 1528 may be configured and/or trained to determine whether the injection device 400 was fraudulently used or wasted. The artificial intelligence module 1528 may be configured and/or trained based on events collected from the injection device 400, such as the administration data 800.

In some embodiments, the artificial intelligence module 1528 may be configured and/or trained to generate a compliance score for an injection. The compliance score may be a quantitative or qualitative value related to one or more aspects of injection via the injection device 400, such as the administration data 800. The artificial intelligence module 1528 may be trailed to generate the compliance score from historical data from the injection device 400, such as the administration data 800.

In example embodiments, a generative artificial intelligence engine (GAIE) may be combined with a machine learning system in an intelligent dosing platform and associated environment. Input to the GAIE may include EMR data, historical medical data, dosing data, guideline data, scans, images, video, audio, text, programmatic code, data, and the like. Outputs from a GAIE may include structured and organized prose, images, video, audio content, software/programming source code, formatted data (e.g., arrays), algorithms, definitions, context-specific structures (e.g., smart contacts, transaction platform configuration data sets, and the like), machine language-based data (e.g., API-formatted content), and the like. For GAIE instances in which the models are designed to process text data, the GAIE may interface to other programmatic systems (such as traditional machine learning engines, and/or intelligent dosing facilities as shown in FIG. 1 and described herein) to process other forms of data into text or other data. In example embodiments, the other programmatic systems, including systems executing machine learning algorithms, may produce textual based (optionally at volume) that may be consumed by GAIE. For example, consider such another system building a series of one thousand text-based observations on the other-formatted data; this may be a useful input for a GAIE model to learn and process (e.g., summarize) into text-formatted output information. In example embodiments, an interface between the GAIE and its combined machine learning system may be extended to include a dialogue between the systems, including the intelligent dosing platform as described herein, where the GAIE includes and/or accesses a capability to ask the machine learning system specific questions to facilitate the refining of its knowledge. For example, the dialogue capability may include a request of the machine learning system to provide an assessment of a clinic's medication inventory, historical ordering pattern(s), and projected medication needs for injectables and related medical components. In another example, the dialogue capability may encode numeric outputs from the machine learning engine into text (e.g., words, such as high, medium, low) that may be input for interpretation by the GAIE.

In example embodiments, the data processed by a GAIE may include one or more types of content. For example, a GAIE may receive, as input, data that represents one or more natural-language expressions, single- or multidimensional shapes or models, real-world and/or virtual scene representations, LIDAR point-cloud representations, sensor inputs and/or outputs (including but not limited to inputs and/or outputs related to an injection device such as a syringe), vehicle and/or machine telemetry, geographic maps, authentication credentials, financial transactions, smart contracts, processing directives and/or resources such as shaders, device configurations such as HDL specifications for programming FPGAs, databases and/or database structural definitions, or the like, including metadata associated with any such data types. Input to the GAIE may also include data that represents one or more features of another machine learning model, such as a configuration (e.g., model type, parameters, and/or hyperparameters), input, internal state (e.g., weights and biases of at least a portion of the model), and/or output of the other machine learning model. These and other forms of content may be received as various forms of data. For example, a natural-language expression received as input by a GAIE could be encoded as one or more of: encoded text, an image of a writing, a sound recording of human speech, a video of an individual exhibiting sign language, an encoding according to a machine learning model embedding, or the like, or any combination thereof. In example embodiments, an input received and processed by the GAIE can include an internal state of the GAIE, such as a partial result of a partial processing of an input, or a set of weights and/or biases of the GAIE as a result of prior processing (e.g., an internal state of a recurrent neural network (RNN)).

In some embodiments, the data and/or content received and processed by a GAIE originates from one or more individuals, such as a person speaking a natural-language expression. In some embodiments, the data and/or content received and processed by a GAIE originates from one or more natural sources, such as patterns formed by nature. In some embodiments, the data and/or content received and processed by a GAIE originates from one or more other devices, such as another machine learning model executing on another device, or from another component such as a syringe or other injection device, or a sensor in an Internet-of-Things (IoT) and/or cloud architecture. In some embodiments, the data and/or content received and processed by a GAIE may be artificially synthesized, such as synthetic data generated by an algorithm to augment a training data set. In some embodiments, the data and/or content received and processed by a GAIE may be generated by the same GAIE, such as an internal state of the GAIE in response to previous and/or concurrent processing, or a previous output of the GAIE in the manner of a recurrent neural network (RNN).

In some embodiments, at least some or part of the data and/or content received and processed by a GAIE is also used to train the GAIE. For example, a variational GAIE could be trained on an input and a corresponding acceptable output and could later receive the same input in order to output one or more variations of the acceptable output. In some embodiments, at least some or part of the data and/or content received and processed by a GAIE is different than data and/or content that was used to train the GAIE. In some such embodiments, the data and/or content received and processed by the GAIE is different than but similar to the data and/or content that was used to train the GAIE, such as new inputs that are exhibit a similar statistical distribution of features as the training data. In some such embodiments, the data and/or content received and processed by the GAIE is different than and dissimilar to the data and/or content that was used to train the GAIE, such as new inputs that exhibit a significantly different statistical distribution of features than the training data. In scenarios that involve dissimilar inputs, one or more first outputs of the GAIE in response to a new input may be compared to one or more second outputs of the GAIE in response to inputs of the training data set to determine whether the first outputs and the second outputs are consistent. The GAIE may request and/or receive additional training based on the new inputs and corresponding acceptable outputs. In scenarios that involve dissimilar inputs, the GAIE may present an alert and/or description that indicates how the new inputs and/or corresponding outputs differ from previously received inputs and/or corresponding outputs.

In example embodiments, the output of a GAIE may include one or more types of content, including but not limited to content related to the status, performance, activity, availability, or some other information related to an injection device associated with the intelligent dosing platform, such as an intelligent syringe or other injection device. A GAIE may generate, as output, data that represents one or more natural-language expressions, single- or multidimensional shapes or models, real-world and/or virtual scene representations, LIDAR point-cloud representations, sensor inputs and/or outputs, vehicle and/or machine telemetry, geographic maps, authentication credentials, financial transactions, smart contracts, processing directives and/or resources such as shaders, device configurations such as HDL specifications for programming FPGAs, databases and/or database structural definitions, or the like, including metadata associated with any such data types. Output of the GAIE may also include data that represents one or more features of another machine learning model, such as a configuration (e.g., model type, parameters, and/or hyperparameters), input, internal state (e.g., weights and biases of at least a portion of the model), and/or output of the other machine learning model. These and other forms of content may be generated by the GAIE as various forms of data. For example, a natural-language expression generated as output by the GAIE could be encoded as one or more of: encoded text, an image of a writing, a sound recording of human speech, a video of an individual exhibiting sign language, an encoding according to a machine learning model embedding, or the like, or any combination thereof. In example embodiments, an output of the GAIE can include an internal state of the GAIE, such as a partial result of a partial processing of an input, or a set of weights and/or biases of the GAIE as a result of prior processing (e.g., an internal state of a recurrent neural network (RNN)).

In example embodiments, a language-based dialogue-enabled GAIE may be configured to produce (e.g., write) new machine learning models that may process various types of data to provide new and extended text input for processing by the GAIE. In example embodiments, humans may observe and interact with this ongoing dialogue between the two systems. In example embodiments, the dialogue is initiated by an expression of a conversation partner (e.g., a human or another device), and the GAIE generates one or more expressions that are responsive to the expression of the conversation partner. In example embodiments, the GAIE generates an expression to initiate the dialogue, and further responds to one or more expressions of the conversation partner in response to the initiating expression. In example embodiments, the ongoing dialogue occurs in a turn-taking manner, wherein each of the conversational partner and the GAIE generating an expression based on a previous expression of the other of the conversation partner and the GAIE. In example embodiments, the ongoing dialogue occurs extemporancously, with each of the conversation partner and the GAIE generating expressions irrespective of a timing and/or sequential ordering of previous and/or concurrent expressions of the conversation partner and/or the GAIE.

In example embodiments, the dialogue may occur between a GAIE and a plurality of conversation partners, such as two or more humans, two or more other GAIEs, or a combination of one or more humans and one or more other GAIEs. In some such example embodiments, the GAIE and each of the other conversation partners take turns generating expressions in response to prior expressions from the GAIE and the other conversation partners. In some such embodiments, one or more sub-conversations occur among one or more subsets of the GAIE and the plurality of conversation partners. Such sub-conversations may occur concurrently (e.g., the GAIE concurrently engages in a first conversation with a first conversation partner and a second conversation with a second conversation partner) and/or consecutively (e.g., the GAIE concurrently engages in a first conversation with a first conversation partner, followed by a second conversation with a second conversation partner). Such sub-conversations may involve the same or similar topics or expressions (e.g., the GAIE may present the same or similar conversation-initiating expression to each of a plurality of conversation partners and may concurrently engage each of the plurality of conversation partners in a separate conversation on the same or similar topic). Such sub-conversations may involve different topics or expressions (e.g., the GAIE may present different conversation-initiating expressions to each of a plurality of conversation partners and may concurrently engage each of the plurality of conversation partners in a separate conversation on different topics). In example embodiments, a first conversation among a first subset of the GAIE and conversation partners may be related to a second conversation among a second subset of the GAIE and conversation partners (e.g., the second subset may engage in a second conversation based on content of the first conversation among a first subgroup).

In example embodiments, one or more of the GAIE and the conversation partner may embody one or more roles. For example, the GAIE may generate expressions based on a role of a conversation starter, a conversation responder, a teacher, a student, a supervisor, a peer, a subordinate, a team member, an independent observer, a researcher, a particular character in a story, an advisor, a caregiver, a therapist, an ally or enabler of a conversation partner, or a competitor or opponent of a conversation partner (e.g., a "devil's advocate" that presents opposing and/or alternative viewpoints to a belief or argument of a conversation partner). In example embodiments, at least one of the one or more conversation partner embodies one or more aforementioned roles or other rules. In an example, one conversation partner may be a patient that is need of administering an injection from an injection device that is in communication with the platform 100. In this example, the conversation partner of the patient may be a GAIE conversation partner embodying the role of a healthcare provider that is knowledgeable about the rules regarding the administration of the injection the patient needs. The conversation may include the GAIE partner guiding the patient through the injection process, telling the patient the approved manner of administering the injection in accordance with the rules governing such administrations, and as stored and embodied on the platform 100. In example embodiments, a role of a GAIE is relative to a role of a conversation partner (e.g., the GAIE may embody a superior, peer, or subordinate role with respect to a role of a conversation partner). In example embodiments, a role of a GAIE in a first conversation among a first subset of the GAIE and a plurality of conversation partners may be the same as or similar to a role of a GAIE in a second conversation among a first subset of the GAIE and the plurality of conversation partners. In example embodiments, a role of a GAIE in a first conversation among a first subset of the GAIE and a plurality of conversation partners may differ from a role of a GAIE in a second conversation among a first subset of the GAIE and the plurality of conversation partners (e.g., the GAIE may embody a role of a teacher in a first conversation and a role of a student in a second conversation). In example embodiments, a role of a GAIE in a conversation may change over time (e.g., the GAIE may first embody a role of a student in a conversation and may later change to a role of a teacher in the same conversation). In example embodiments, a GAIE may embody two or more roles in a conversation (e.g., the GAIE may exhibit two personalities in a conversation that respectively represent one of two characters in a story). In example embodiments, a GAIE generates expressions between two or more roles in a conversation (e.g., the GAIE may generate a dialogue between each of two characters in a story). In example embodiments, a GAIE may engage in each of multiple conversations in a same or similar modality (e.g., engaging in multiple text-based conversations concurrently). In example embodiments, a GAIE may engage in each of multiple conversations in different modalities (e.g., engaging in a first conversation via text and a second conversation via voice).

In example embodiments, a GAIE participating in a conversation is associated with an avatar (e.g., a name, color, image, two- or three-dimensional model, voice, or the like). Expressions generated by the GAIE may be presented as if originating from the GAIE (e.g., in the voice associated with the GAIE, or in a speech bubble that is displayed near a visual position of a GAIE in a virtual or augmented-reality environment). In example embodiments, an avatar of a GAIE may be based on a role of the GAIE (e.g., a GAIE embodying a role of a teacher may be associated with an avatar depicting a teacher). In example embodiments, an avatar of a GAIE may be included in a real-world actor, such as a robot in a real-world environment such as a stage performance.

In example embodiments, a GAIE may include generative pretrained transformer elements that may be configured as a language model designed to understand various types of input and produce chat commands for a chat-type interface system. These commands may include software development tasks, API calls, and the like. In example embodiments, such a language model may include input functions that support receiving images, including video, to build textual output, functions, and additional questions that may be injected into the dialogue between the two systems in the dialogue embodiment described above. In example embodiments, this multimodal support may allow for contextual analysis of images and other media formats. In an example, users/customers may upload images or other media into a GAIE enabled platform. Based on aspects of a corresponding input prompt, a multi-modal GAIE may be configured for use in a valuation workflow to identify both macro and micro attributes and their correlated effects on valuation from a plurality of perspectives. In this example, photographs/images of an old car may be input along with a valuation-related prompt. In response, the GAIE may identify one or more typical values based on detected attributes of the car, such as the make/model, etc. The GAIE may further consider finer details in the image to suggest potential value-altering metrics. In one example, a finer detail in the image such as damaged body panels may reduce the car value below a typical value. In another example, a finer detail in the image that shows a marking consistent with a limited production run may increase the valuation.

In example embodiments, such a GAIE may facilitate workflow orchestration for a process that uses a conversational, generative AI agent and another AI-supported process in an orchestrated sequence. In example embodiments, a GAIE may generate, perform, maintain, and/or supervise one or more workflows in a robotic process automation (RPA) environment. For example, a GAIE may be trained to monitor expressions and/or actions of an individual during interaction with other individuals and may generate similar expressions and/or perform similar actions during similar interactions between the GAIE and other individuals. In some such scenarios, the GAIE passively observes the individual during the interactions with other individuals and self-trains to behave similarly to the individual in similar interactions with other individuals. In some such scenarios, the individual actively trains and/or teaches the GAIE to generate expressions and/or actions (e.g., by creating and/or performing example or pedagogical interactions the GAIE), and based on the training and/or teaching, the GAIE behaves similarly during subsequent interactions between the GAIE and other individuals. In example embodiments, the GAIE is trained and/or taught by an individual to perform a behavior while interacting with individuals, and subsequently performs the behavior while interacting with the same individual who provided the training and/or teaching.

In example embodiments, a pretrained GAIE system may have a smart contract analysis engine that determines one or more features of a smart contract that is under consideration by a user. The GAIE may further have a conversation engine that explains the features of the smart contract to the user, including summarizing contents of smart contracts.

Candidate areas of innovation enabled by and/or associated with GAIE advances may include user behavior models (optionally with feedback and personalization), group clustering and similarity, personality typing, governance of inputs and process, explaining the basis of GAIE knowledge and proof points, genetic programming with feedback functions, intelligent agents, voice assistants and other user experiences, transactional agents (counterparty discovery and negotiation), agents that deal with other agents, opportunity miners, automated discovery of opportunities for agent generation and application, user interfaces that adapt to the user and context, hybrid content generation, collaboration units of humans and generative AI, purpose-specific data integration, a selected set of data sources, curation of data as models as input to generative AI, and the like.

In example embodiments, a GAIE may be configured to support interpretability and/or explainability of its outputs. In example embodiments, a GAIE provides, along with an output, a description of a basis of the output, such as an explanation of the reason for generating this particular output in response to an input. In example embodiments, a GAIE provides, along with an output, a description of an internal state of the GAIE that resulted in the output, such as a set of variational parameters of a variational encoder that were processed in combination with an input to produce an output, and/or an internal state of the GAIE due to a previous processing of the GAIE that resulted in the output (e.g., similar to a recurrent neural network (RNN)). In example embodiments, a GAIE provides, along with an output, an indication of one or more subsets of features of an input that are particularly associated with the output (e.g., in a GAIE that outputs a caption or summary of an image, the GAIE can also identify the particular portions or elements of the image that are associated with the caption or portions of the summary).

In example embodiments, an advanced GAIE, such as one pretrained for subject matter specific operation, may be trained for improved epistemology, to help determine evidence of the content that it represents as facts in responses that it provides. One example of improved epistemology may include citing sources of knowledge pertinent to facts in a response as a step toward proof of facts of a response-essentially a way of the GAIE "showing its work," or at least where its work originates. In example embodiments, a GAIE generates output based on information received from one or more external sources (e.g., one or more messages in a message set, or one or more websites on the Internet), and the GAIE indicates one or more portions of the information that are associated with the output (e.g., one or more websites on the Internet that provided information that is included in the output of the GAIE).

An advanced GAIE as described and envisioned herein may maintain contextual awareness across chat (user-prompt/GAIE-response) interactions. Maintaining contextual awareness may help avoid the GAIE beginning each chat session from scratch, with no context as to prior chats with the same user. Maintaining contextual awareness may also enable picking up and resuming a conversation from earlier interactions between the GAIE and a user. Yet further maintaining contextual awareness and awareness of passage of time between interaction sessions may facilitate adapting responses to prompts in a later resumed chat session based on trained knowledge of the intervening passage of time and/or changing circumstances. In an example, a GAIE may determine that a deadline described in an earlier chat has expired, a consequential intervening event has occurred (your home-town team lost the big game), and the like. Further, contextual awareness across time-separate chat sessions may be highly valuable when being employed for projects that may have real-world physical constraints on time (e.g., smart contract negotiation may involve human evaluation, discussion, and decision making that may take time based, for example on other priorities seeking involvement of the human). This may determine the difference between treating each conversation as individual/compartmentalized/isolated, and treating ongoing, time-separated conversations as resumable, optionally as if (almost) no time had passed. In example embodiments, a GAIE may be configured with a contextualization module that maintains some notion of conversation sessions and interconnections that may be referred (e.g., a conversation from yesterday) for details and continuity. This contextualization may further enable avoiding repeating responses, making it more efficient to reference a previous conversation. Yet further, a contextualization module may provide context to the GAIE of other conversations between the user and the system, between other users and the system, and the like.

In such a contextually maintained instance, a context-enabled GAIE may provide a response regarding the administration of an medication injection using an injection device that references at least one earlier instance of an administration of the same medication using the same injection device. In an example, a context-enabled GAIE may provide a context-related response such as, "During the prior administration of this medication, the entry angle of the injection device was at first incorrect. Please note that the correct entry angle of the injection device into the patient's upper limb is preferably perpendicular to the limb."

In example embodiments, a GAIE may be pre-trained for use by and/or in cooperative operation with a digital twin engine, such as an instance of an executive digital twin and the like. In an exemplary deployment, a GAIE may interact with a digital twin to provide a narrative about a topic of the digital twin to give to a viewer. In this example, the digital twin may interact with the GAIE (e.g., through an API and the like) to generate a narrative summary for a CEO and a detailed narrative for a CFO. For example, preceding, during or following the presentation of the context-related response of "During the prior administration of this medication, the entry angle of the injection device was at first incorrect. Please note that the correct entry angle of the injection device into the patient's upper limb is preferably perpendicular to the limb," a digital twin may be created by the platform 100, one output of which may be an image, video or other media showing the patient at least one view of the injection device placed in the proper perpendicular angle for administration of the medication into the upper limb.

Executive digital twins may be configured for a particular role or user. Therefore, a GAIE system with a digital twin interface may improve executive digital twin capabilities by curating the data for and populating content for consumption by executive digital twins for different roles. In an example a GAIE may receive information about the executive digital twin as well as about the intended human being represented by the executive digital twin (e.g., the role of the user). The GAIE may determine a degree of narrative detail for each executive digital twin. This may be based on generic executive digital twin/user role criteria and/or refined through interaction with a particular user for the executive digital twin. In example embodiments, a surgeon may receive more "in-depth" narrative relating to use of an injection device, whereas a lab technician may receive narratives that are more focused on basic injection device usage.

In example embodiments, a GAIE system that interacts with a digital twin engine (e.g. an executive digital twin instance and/or engine) may determine of the potential universe of content on which it is trained, what may be relevant and what may be noise or unrelated for the specific narrative topic, the target human consumer, and the like. Based on this relevance determination, the GAIE system may generate the output data based on the relevant data and the determined degree of detail.

Further, the GAIE system may also select real time data sources to connect to a target/requesting executive digital twin. The GAIE may further configure consumption pipelines for those sources on the spot (e.g., data source identification, data requests for identified data sources, API configuration, and the like). Therefore, in this example the GAIE system would be identifying data sources and connecting them to an executive digital twin instance/engine.

An example use case may include an executive digital twin that has access to full medical data from a previous time-frame (e.g., a previous year, and the like). The executive digital twin may enable access by the GAIE to all of this data. The GAIE may determine a degree of detail of the data for the intended viewer (e.g., target consumer of a narrative regarding a topic captured in the full medical data).

A pre-trained GAIE may be used to generate, manage, and/or manipulate digital twins, such as by describing attributes of a digital twin, describing interactions with other digital twins or environments, describing simulations, using digital twin simulation data to generate content, enabling context-adaptive executive digital twins, facilitating development of narratives about ongoing, real time operations, tuned to the preferred conversation style of a user represented by a digital twin, and the like. In example embodiments, a context-adaptive executive digital twin integrated with a generative conversational AI system may be configured to generate a set of narratives about operations of an enterprise based on an input data set of real-time sensor data from the operations of the enterprise. The digital twin (or human user) may prompt the GAIE and/or conversational AI system to compare financials with real-time sensor data.

A GAIE may be adapted (e.g., pre-trained) to facilitate enhancement of AI training data associated with a digital twin application. In example embodiments, a method may include using an AI conversational agent to create synthetic training data.

Further in association with digital twin technology, a GAIE may be adapted for summarizing highly granular data for consumption by an executive digital twin. In this regard, an executive digital twin system may include an intelligent agent that receives a set of customization features from a user (e.g., an executive represented by the digital twin) that include a role of the user within an organization. The intelligent agent may also determine a respective granularity level of a report based on the customization features. In example embodiments, the set of customization features include granularity designations for different types of reports. Yet further, the intelligent agent determines the granularity level of a report based on the role of the user within an organization. Further, the subject matter of the report may be generated based on the role of the user within the organization.

A fine-tuned GAIE system may play a role in systematic risk identification, management, and opportunity mining. GAIE-based risk identification systems may respond to risk-related prompts, such as "What may else might we know and should be paying attention to?" by curating data sets and automating the processes of identification of systemic risks, identifying a set of likely scenarios and the risks and opportunities arising from those scenarios, identifying paths for resolution and recommending resolutions. For example, prior to the administration of a medication using an injection device, the platform 100 may present a risk-related prompt for the party administering the medication to double-check for contraindications regarding the medication to be administered and the other medications that the patient is taking. The platform 100 may require the party administering the medication to affirmatively respond that there are no contraindications prior to the platform releasing the injection device (e.g., removing a lock on the device or removal of some other type of security measure) to administer the medication to the patient.

Yet another area of risk identification and/or management may involve security concerns with GAIE systems that are configured to generate computer executable code. At the least relying on computers to write computer code raises questions about what security measures are effective and what measures are able to be circumvented by the AI.

Yet another risk-identification related area includes fraud detection. Integrating customer fraud reporting and questioning into pretraining data may enrich holistic scoring, which may comprise a composite score that bridges customer evidence, transactions, and environmental trends. In an example, an AI based fraud detection system may integrate customer and/or industry fraud reports and questioning into a training/query data set to produce a holistic scoring system, utilizing a composite score that combines customer evidence, transaction data, and environmental trends to provide a comprehensive approach to fraud detection. In an example, an injection device may include a component that is used by the platform to validate its authenticity and suitability as a patient delivery system. In another example, in the event of a known type of fraudulent injection device and/or medication within injection devices, a characteristic of the fraudulent device or medication may be stored by the platform and future device specifically checked for the presence of the characteristic. If such characteristic is detected, an alert or other warning, prevention mechanism, lock or other process may be implemented to prevent the use of the detected fraudulent injection device.

Imaging applications may benefit from fine-tuned GAIE systems. In example embodiments, optical content (e.g., screen shots and the like) may be processed by machine vision systems so that the GAIE may describe a scene in the optical content using a generative conversational AI agent. In example embodiments, a GAIE may be configured as a first AI/NN sub-system in a Dual Process Artificial Neural Network (DPANN) architecture. Such a DPANN architecture may include, as a second NN sub-system, a formal logic-based and/or fuzzy-based system. Together these DPANN systems may implement learning processes, model management, and the like. In example embodiments, a DPANN architecture may include features that describe building and managing large scale models.

Figure 16:
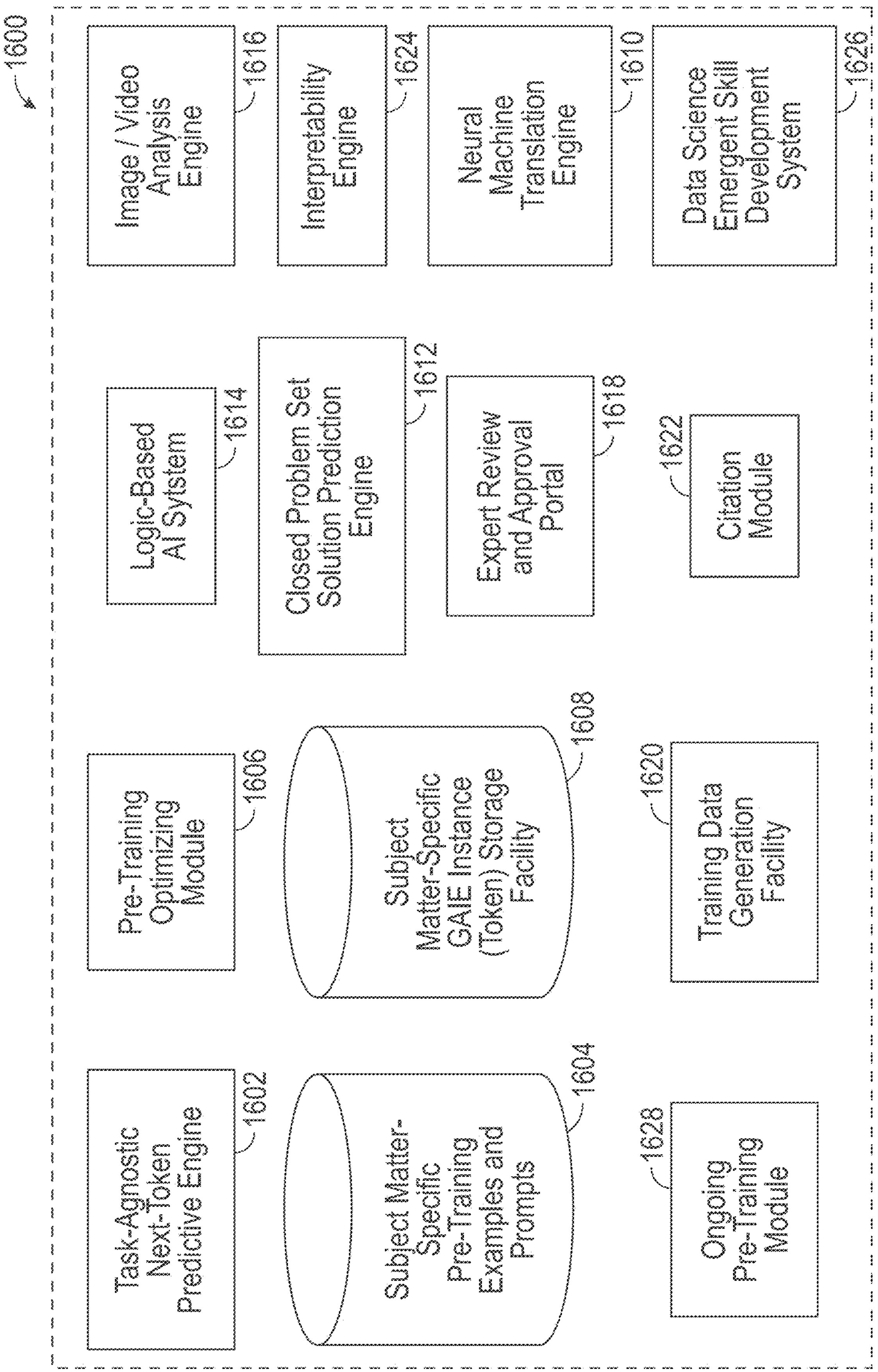
FIG. 16 depicts a block diagram of exemplary features, capabilities, and interfaces of a generative artificial intelligence platform of an intelligent dosing platform.

Referring to FIG. 16, the platform 100, as described herein, may include a generative AI module 1600 that may include a robust task-agnostic next-token prediction artificial intelligence engine 1602 that operates to predict a next token given a set of inputs encoded as embedded tokens. A robust task-agnostic next-token prediction AI engine 1602 may include deep learning models, which use multi-layered neural networks to process, analyze, and make predictions with complex data, such as language. An objective of the robust next-token prediction AI engine 1602 may include data science modeling through, among other things, use of topic-specific embeddings, attention mechanisms, and decoder-only transformer models. Capabilities of such an engine 1602 may include a pre-training capability to facilitate configuring next-token prediction for specific subject matter (e.g., marketplace item valuation), a tokenizing capability to facilitate converting complex terms into actionable tokens (e.g., converting compound chemical names into fundamental elements), access to distributed training (e.g., data-parallel training and/or model-parallel training, and the like), few-shot learning to reduce training demand for updates, such as new medical intelligence data, and the like. In general, the next-token prediction AI engine 1602 may combine large language modeling techniques and decoder-only transformer models to generate powerful foundation models for next-token prediction AI content generation.

In example embodiments, the next-token prediction AI engine 1602 may be structured with a machine learning (sparse Multi-Layer Perceptron) architecture configured to sparsely activate conditional computation using, for example mixture-of-experts (MoE) techniques. A machine learning architecture may be configured with expert modules that may be used to process inputs and a gating function that may facilitate assigning expert modules to process portion(s) of input tokens. A machine learning architecture may further include a combination of deterministic routing of input tokens to expert modules and learned routing that uses a portion of input tokens to predict the expert modules for a set of input tokens.

A generative AI engine (GAIE) may be trained to operate within a domain, such as written language, computer programming language, subject matter-specific domains (e.g., a software orchestrated marketplace domain), and the like to generate content (constructs) that comply with rules of the domain. In general, a GAIE may generate content for any topic for which the GAIE is trained. So, for example, a GAIE may be trained on a topic and may therefore generate language-based descriptions, images, contracts, breeding guidance, textual output, and the like for any of a potentially wide range of sub-topics.

Adapting a generative AI engine for subject matter-specific applications may include pretraining a next-token prediction AI model-based system through the use of, for example, in-context (e.g., application, domain, topic-specific) examples that are responsive to a corresponding prompt. While the next-token predictive capabilities of the underlying next-token prediction AI engine may remain unaffected by this pre-training, subject matter-specific pre-trained instances may be developed/deployed.

In example embodiments, a platform for the application of module 1600 may include a set of subject matter-specific pretrained examples and prompts 1604. This set 1604 may be configured by analyzing (e.g., by a human expert and/or computer-based expert and/or digital twin) information that characterizes various aspects of the domain to generate example prompts and preferred and/or correct responses. Pretraining may also include training the next-token prediction AI engine 1602 by sampling some text (e.g., prompt/response sets) from the set of subject matter-specific pre-trained examples and prompts 1604 and training it to predict a next word, object, and/or term. Pretraining may also include sampling some images, contracts, architectures, and the like to predict a next token. These prompt-response sub-sets may facilitate pre-training the prediction AI engine 1602 for predicting a next token (e.g., word, object, image element, and the like) for various aspects.

When an instance is implemented for textual generation, such a GAIE instance may be referred to as a natural language generation system that constructs words (e.g., from sub-word tokens), sentences, and paragraphs for a target subject and/or domain.

In example embodiments, real-world instances of the module 1600 may require ongoing updates to facilitate the module 1600 being responsive as aspects of a domain (e.g., a medical entity in the domain) change, such as business goals change, new products are released, competitors merge, new markets emerge, and the like. In this regard, training the module 1600 with in-context prompts and examples may be automated and repeated as new data is released for an enterprise to prevent snapshot-in-time data aging-based errors. The platform the application of module 1600 may include an ongoing pre-training module 1628 that processes new and updated content into prompt and/or response sets and interactively iterates through rounds of pre-training. Now and updated data and/or information may regularly be found in various subject matter specific information sets, such as: a dataset of medical records (e.g., to assist with medical diagnoses), a dataset of legal documents and court decisions (e.g., to provide legal advice), a release of a new product (e.g., images of the product), or a medical-related dataset such as FDA recommendations or other reports. In example embodiments, uses of the module 1600 may include applying the pre-training and optimizing techniques to a range of different domains (e.g., medical diagnosis, business operation, marketplace operation, and the like) to produce a fine-tuned domain specific token-predictive engine including ongoing refinement through (daily) in-context pretraining.

In example embodiments, an ongoing pre-training module 1628 may work with the next-token prediction AI engine 1602 to update a set of subject matter specific tokens that may be maintained in a subject matter specific instance token storage facility 1608. This subject matter specific instance token storage facility 1608 may be referenced by a subject matter specific instance of the next-token prediction AI engine 1602 during an operational mode (e.g., when processing inputs/prompts). In example embodiments, the module 1600 may include a plurality of sets of subject matter specific tokens that may be maintained by corresponding ongoing pre-training modules 1628.

Training, however, may not ensure that the responses to prompts are correct every time. In general, an entity is likely to be less interested in a tool that provides answers that are probably right and may differ from time to time. A product that can provide accurate responses (e.g., including taking actions) based on what the end-user wants vastly increases the potential use cases and product value. A high level of accuracy and integration with operational systems may enable such a tool to go beyond just generating new content to be more productive; through integration with workflows, it may facilitate automating workflow actions. In this regard, the platform for the application of module 1600 may also include a pre-training optimizing module 1606 that may work cooperatively with the ongoing pre-training module 1628 to further refine accuracy of responses to prompts for a domain. The pre-training optimizing circuit 1606 may facilitate improved accuracy of in-context responses, task-specific fine-tuning, and for sparse model variants of the module 1600, enrich few-shot learning capabilities. In example embodiments, fine tuning may further benefit the platform by reducing bias that may be present in the training data. This may be essential to ensure subject matter specific jargon is adapted as training data changes. Further, a pre-training optimizing engine 1606 may provide a wider range of prompts and responses based on user preferences (e.g., speaking styles) to enrich the platform's ability to provide user-centric responses. In example embodiments, user-centric responses may include fine tuning the module 1600 for different roles in an organization. As an example, when a user in a medical provider role inquires about an injection device topic, responses may be directed toward the medical provider role, as opposed to a patent or other role about the same topic.

A platform for the application of module 1600 may be used to produce text-based content for an entity with employees who speak different languages. While the module 1600 may be trained (and pre-trained) to operate interactively in a plurality of languages, generating automated content may benefit from use of a neural machine translation module 1610. In example embodiments, a portion of the entity in a first jurisdiction may produce content in a first language and resulting recurring generated output (e.g., types of reports and the like) may be generated in the first language. However, employees who speak a second language may benefit from the type of report when translated into the employee's native language. Therefore, associating the neural machine translation module 1610 with the platform may prove valuable while reducing compute demand for the module 1600.

Emerging next-token prediction AI systems feature increasingly adaptable next token prediction capabilities. These capabilities may be further adapted to assist in closed problem set solution prediction, such as allocation of resources, deployment of a robotic fleet and the like. To achieve greater prediction capabilities, a subject matter specific next-token prediction AI-based engine, such as the platform for the application of module 1600, may include a solution-predictive engine 1612 that leverages next-token (e.g., next word) predictive capabilities to predict a most-likely solution to a closed solution-set problem. This may be accomplished optionally through use of sets of problem domain-specific pre-training prompts and examples. Such examples may be adapted for different user preferences. In example embodiments, each user in a closed problem set environment may generate prompts and responses that may enable the module 1600 to respond to the user based on the user's inquiry style. Alternatively, the solution-predictive engine 1612 may adapt a user's prompt and/or configure a prompt based on user preferences to attempt to deliver responses that are consistent with a user's preferences (e.g., nurse-based responses for a nurse role-user and patient-based responses for a patient).

For more complex analysis and decision making/predicting, a formal logic-based AI system 1614 may be incorporated into and/or be referenced by the subject matter specific module 1600.

Further, the basic concepts of next-token prediction of a generative AI engine, such as the platform for subject matter-based application of module 1600 may be applied to analyzed expressions of images, audio (e.g., encoded text), video (e.g., sequences of related images), programmatic code (domain-specific text with readily understood rules), and the like. Therefore, a next-token prediction AI platform (e.g., module 1600) may further include an image/video analysis engine 1616 (optionally NN-based) that adds a spatial aspect to the next-token predictive capabilities of a next-token prediction AI system. Images used for training may include 3D CAD images, syringe injection angle or radiologic images (for a medical analysis), business performance graphs, schematics, and the like. In example embodiments, aspects of the underlying task-agnostic next-token prediction AI engine 1602 may be adapted (e.g., different embeddings, neural network structures and the like) for different input formats, such as images, temporal-spatial content, and the like.

The module 1600 may further include an expert review and approval portal 1618 through which an expert (e.g., human/digital twin, and the like) can review, edit, and approve content generated. Examples include review and adaptation by a subject matter specific data story expert; a data scientist, and the like. The expert review and approval portal 1618 may operate cooperatively with, for example, the pre-training optimizing module 1606 that may receive and analyze expert feedback (e.g., edits to the content and the like) for opportunities to further optimize the module 1600.

The module 1600 may further include a training data generation facility 1620 that may generate natural language prompts, such as subject matter specific prompts that may be applied by, for example, the pre-training optimizing engine 1606 to increase platform response accuracy and/or efficiency while fine tuning a subject matter specific instance.

In example embodiments, the module 1600 may further be configured to access a corpus of domain and/or problem relevant content as a step in responding to a prompt. In example embodiments, the platform may be pre-trained on the content of the corpus While the content of the corpus may not be directly included in the response, such as if it provides a level of detail beyond what the module 1600 has been trained to provide in a response, it may be cited in the response to facilitate identifying and expressing sources from which a response is derived. These external source references may be handled via a citation module 1622.

Medical decisions are often context-based. Understanding both the context for a decision and aspects and/or assumptions of the decision process may prove highly valuable for evaluating, for example, competing decisions and/or recommendations. Context may include both tangible and intangible factors. An intangible factor may include historical interactions between parties involved in the evaluation process, for example. A decision process may include not only assumptions on which a decision or recommendation is based, but also criteria by which tangible factors are processed, evaluated, analyzed, and the like. To provide such context for generated output of the module 1600, an interpretability engine 1624 may be incorporated into and/or be accessible to the module 1600. An objective of use of the interpretability engine 1624 may be to generate additional content that reflects context for, among other things, how the next-token prediction AI instance operates and/or generates a corresponding output.

In example embodiments, the next-token predictive capabilities of a next-token prediction AI engine 1602 may be utilized for developing a set of emergent data science predictive and/or interpretive skills. While such a platform may be trained directly on various data sets, context for elements and results in such data sets may be a rich source of complementary training data. By associating data elements with descriptions thereof, the module 1600 may gain data science capabilities, such as to group by or pivot categorical sums, infer feature importance, derive correlations, predict unseen test cases, and the like. In this regard, a data science emergent skill development system 1626 may be utilized by the platform to enhance further subject matter specific applicability and utility.

Special-purpose systems include hardware and/or software and may be described in terms of an apparatus, a method, or a computer-readable medium. In various embodiments, functionality may be apportioned differently between software and hardware. For example, some functionality may be implemented by hardware in one embodiment and by software in another embodiment. Further, software may be encoded by hardware structures, and hardware may be defined by software, such as in software-defined networking or software-defined radio.

The methods and/or processes described in the disclosure, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable devices, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

In this application, including the claims, the term module refers to a special-purpose system. The module may be implemented by one or more special-purpose systems. The one or more special-purpose systems may also implement some or all of the other modules. In this application, including the claims, the term module may be replaced with the terms "controller" or "circuit." In this application, including the claims, the term platform refers to one or more modules that offer a set of functions. In this application, including the claims, the term system may be used interchangeably with module or with the term special-purpose system.

The special-purpose system may be directed or controlled by an operator. The special-purpose system may be hosted by one or more of assets owned by the operator, assets leased by the operator, and third-party assets. The assets may be referred to as a private, community, or hybrid cloud computing network or cloud computing environment. For example, the special-purpose system may be partially or fully hosted by a third party offering software as a service (SaaS), platform as a service (PaaS), and/or infrastructure as a service (IaaS). The special-purpose system may be implemented using agile development and operations (DevOps) principles. In example embodiments, some or all of the special-purpose system may be implemented in a multiple-environment architecture. For example, the multiple environments may include one or more production environments, one or more integration environments, one or more development environments, etc.

A special-purpose system may be partially or fully implemented using or by a mobile device. Examples of mobile devices include navigation devices, cell phones, smart phones, mobile phones, mobile personal digital assistants, palmtops, netbooks, pagers, electronic book readers, tablets, music players, etc. A special-purpose system may be partially or fully implemented using or by a network device. Examples of network devices include switches, routers, firewalls, gateways, hubs, base stations, access points, repeaters, head-ends, user equipment, cell sites, antennas, towers, etc.

A special-purpose system may be partially or fully implemented using a computer having a variety of form factors and other characteristics. For example, the computer may be characterized as a personal computer, as a server, etc. The computer may be portable, as in the case of a laptop, netbook, etc. The computer may or may not have any output device, such as a monitor, line printer, liquid crystal display (LCD), light emitting diodes (LEDs), etc. The computer may or may not have any input device, such as a keyboard, mouse, touchpad, trackpad, computer vision system, barcode scanner, button array, etc. The computer may run a general-purpose operating system, such as the WINDOWS operating system from Microsoft Corporation, the MACOS operating system from Apple, Inc., or a variant of the LINUX operating system. Examples of servers include a file server, print server, domain server, internet server, intranet server, cloud server, infrastructure-as-a-service server, platform-as-a-service server, web server, secondary server, host server, distributed server, failover server, and backup server.

The term hardware encompasses components such as processing hardware, storage hardware, networking hardware, and other general-purpose and special-purpose components. Note that these are not mutually-exclusive categories. For example, processing hardware may integrate storage hardware and vice versa.

Examples of a component are integrated circuits (ICs), application specific integrated circuit (ASICs), digital circuit elements, analog circuit elements, combinational logic circuits, gate arrays such as field programmable gate arrays (FPGAs), digital signal processors (DSPs), complex programmable logic devices (CPLDs), etc.

Multiple components of the hardware may be integrated, such as on a single die, in a single package, or on a single printed circuit board or logic board. For example, multiple components of the hardware may be implemented as a system-on-chip. A component, or a set of integrated components, may be referred to as a chip, chipset, chiplet, or chip stack. Examples of a system-on-chip include a radio frequency (RF) system-on-chip, an artificial intelligence (AI) system-on-chip, a video processing system-on-chip, an organ-on-chip, a quantum algorithm system-on-chip, etc.

The hardware may integrate and/or receive signals from sensors. The sensors may allow observation and measurement of conditions including temperature, pressure, wear, light, humidity, deformation, expansion, contraction, deflection, bending, stress, strain, load-bearing, shrinkage, power, energy, mass, location, temperature, humidity, pressure, viscosity, liquid flow, chemical/gas presence, sound, and air quality. A sensor may include image and/or video capture in visible and/or non-visible (such as thermal) wavelengths, such as a charge-coupled device (CCD) or complementary metal-oxide semiconductor (CMOS) sensor.

The methods and systems described herein may be deployed in part or in whole through a machine that executes computer software, program codes, and/or instructions on a processor. The present disclosure may be implemented as a method on the machine, as a system or apparatus as part of or in relation to the machine, or as a computer program product embodied in a computer readable medium executing on one or more of the machines. In example embodiments, the processor may be part of a server, cloud server, client, network infrastructure, mobile computing platform, stationary computing platform, or other computing platforms. A processor may be any kind of computational or processing device capable of executing program instructions, codes, binary instructions and the like, including a central processing unit (CPU), a general processing unit (GPU), a logic board, a chip (e.g., a graphics chip, a video processing chip, a data compression chip, or the like), a chipset, a controller, a system-on-chip (e.g., an RF system on chip, an AI system on chip, a video processing system on chip, or others), an integrated circuit, an application specific integrated circuit (ASIC), a field programmable gate array (FPGA), an approximate computing processor, a quantum computing processor, a parallel computing processor, a neural network processor, an approximate computing processor, a quantum computing processor, a parallel computing processor, a neural network processor, a signal processor, a digital processor, a data processor, an embedded processor, a microprocessor, and a co-processor. The co-processor may provide additional processing functions and/or optimizations, such as for speed or power consumption, or other type of processor. Examples of co-processors include a math co-processor, a graphics co-processor, a communication co-processor, a video co-processor, and an artificial intelligence (AI) co-processor. The processor may be or may include a signal processor, digital processor, data processor, embedded processor, microprocessor or any variant such as a co-processor (math co-processor, graphic co-processor, communication co-processor, video co-processor, AI co-processor, and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code.

The processor, or any machine utilizing one, may include non-transitory memory that stores methods, codes, instructions and programs as described herein and elsewhere. The processor may access a non-transitory storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache, network-attached storage, server-based storage, and the like. The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, network-attached storage, network storage, NVME-accessible storage, PCIE connected storage, distributed storage, and the like.

A processor may include one or more cores that may enhance speed and performance of a multiprocessor. In example embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server, cloud server, and other variants such as secondary server, host server, distributed server, and the like. The server may include one or more of memories, processors, computer readable transitory and/or non-transitory media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The processor may enable execution of multiple threads. These multiple threads may correspond to different programs. In various embodiments, a single program may be implemented as multiple threads by the programmer or may be decomposed into multiple threads by the processing hardware. The threads may be executed simultaneously to enhance the performance of the processor and to facilitate simultaneous operations of the application. A processor may be implemented as a packaged semiconductor die. The die includes one or more processing cores and may include additional functional blocks, such as cache. In various embodiments, the processor may be implemented by multiple dies, which may be combined in a single package or packaged separately.

The networking hardware may include one or more interface circuits. In some examples, the interface circuit(s) may implement wired or wireless interfaces that connect, directly or indirectly, to one or more networks. Examples of networks include a cellular network, a local area network (LAN), a wireless personal area network (WPAN), a metropolitan area network (MAN), and/or a wide area network (WAN). The networks may include one or more of point-to-point and mesh technologies. Data transmitted or received by the networking components may traverse the same or different networks. Networks may be connected to each other over a WAN or point-to-point leased lines using technologies such as Multiprotocol Label Switching (MPLS) and virtual private networks (VPNs).

Examples of cellular networks include GSM, GPRS, 3G, 4G, 5G, LTE, and EVDO. The cellular network may be implemented using frequency division multiple access (FDMA) network or code division multiple access (CDMA) network. Examples of a LAN are Institute of Electrical and Electronics Engineers (IEEE) Standard 1102.11-2020 (also known as the WIFI wireless networking standard) and IEEE Standard 1102.3-2018 (also known as the ETHERNET wired networking standard). Examples of a WPAN include IEEE Standard 1102.15.4, including the ZIGBEE standard from the ZigBee Alliance. Further examples of a WPAN include the BLUETOOTH™ wireless networking standard, including Core Specification versions 3.0, 4.0, 4.1, 4.2, 5.0, and 5.1 from the Bluetooth Special Interest Group (SIG). A WAN may also be referred to as a distributed communications system (DCS). One example of a WAN is the internet.

Storage hardware is or includes a computer-readable medium. The term computer-readable medium, as used in this disclosure, encompasses both nonvolatile storage and volatile storage, such as dynamic random access memory (DRAM). The term computer-readable medium only excludes transitory electrical or electromagnetic signals propagating through a medium (such as on a carrier wave). A computer-readable medium in this disclosure is therefore non-transitory, and may also be considered to be tangible.

Examples of storage implemented by the storage hardware include a database (such as a relational database or a NoSQL database), a data store, a data lake, a column store, and a data warehouse. Examples of storage hardware include nonvolatile memory devices, volatile memory devices, magnetic storage media, a storage area network (SAN), network-attached storage (NAS), optical storage media, printed media (such as bar codes and magnetic ink), and paper media (such as punch cards and paper tape). The storage hardware may include cache memory, which may be collocated with or integrated with processing hardware. Storage hardware may have read-only, write-once, or read/write properties. Storage hardware may be random access or sequential access. Storage hardware may be location-addressable, file-addressable, and/or content-addressable.

Examples of nonvolatile memory devices include flash memory (including NAND and NOR technologies), solid state drives (SSDs), an erasable programmable read-only memory device such as an electrically erasable programmable read-only memory (EEPROM) device, and a mask read-only memory device (ROM). Examples of volatile memory devices include processor registers and random access memory (RAM), such as static RAM (SRAM), dynamic RAM (DRAM), synchronous DRAM (SDRAM), synchronous graphics RAM (SGRAM), and video RAM (VRAM). Examples of magnetic storage media include analog magnetic tape, digital magnetic tape, and rotating hard disk drive (HDDs). Examples of optical storage media include a CD (such as a CD-R, CD-RW, or CD-ROM), a DVD, a Blu-ray disc, and an Ultra HD Blu-ray disc.

Examples of storage implemented by the storage hardware include a distributed ledger, such as a permissioned or permissionless blockchain. Entities recording transactions, such as in a blockchain, may reach consensus using an algorithm such as proof-of-stake, proof-of-work, and proof-of-storage. Elements of the present disclosure may be represented by or encoded as non-fungible tokens (NFTs). Ownership rights related to the non-fungible tokens may be recorded in or referenced by a distributed ledger. Transactions initiated by or relevant to the present disclosure may use one or both of fiat currency and cryptocurrencies, examples of which include bitcoin and ether. Some or all features of hardware may be defined using a language for hardware description, such as IEEE Standard 1364-2005 (commonly called “Verilog”) and IEEE Standard 1376-2008 (commonly called “VHDL”). The hardware description language may be used to manufacture and/or program hardware.

A special-purpose system may be distributed across multiple different software and hardware entities. Communication within a special-purpose system and between special-purpose systems may be performed using networking hardware. The distribution may vary across embodiments and may vary over time. For example, the distribution may vary based on demand, with additional hardware and/or software entities invoked to handle higher demand. In various embodiments, a load balancer may direct requests to one of multiple instantiations of the special purpose system. The hardware and/or software entities may be physically distinct and/or may share some hardware and/or software, such as in a virtualized environment. Multiple hardware entities may be referred to as a server rack, server farm, data center, etc.

Software includes instructions that are machine-readable and/or executable. Instructions may be logically grouped into programs, codes, methods, steps, actions, routines, functions, libraries, objects, classes, etc. Software may be stored by storage hardware or encoded in other hardware. Software encompasses (i) descriptive text to be parsed, such as HTML (hypertext markup language), XML (extensible markup language), and JSON (JavaScript Object Notation), (ii) assembly code, (iii) object code generated from source code by a compiler, (iv) source code for execution by an interpreter, (v) bytecode, (vi) source code for compilation and execution by a just-in-time compiler, etc. As examples only, source code may be written using syntax from languages including C, C++, JavaScript, Java, Python, R, etc. The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the devices described in the disclosure, as well as heterogeneous combinations of processors, processor architectures, or combinations of different hardware and software, or any other machine capable of executing program instructions. Computer software may employ virtualization, virtual machines, containers, dock facilities, portainers, and other capabilities. In example embodiments, methods described in the disclosure and combinations thereof may be embodied in computer executable code that, when executing on one or more computing devices, performs the steps thereof. In another aspect, the methods may be embodied in systems that perform the steps thereof and may be distributed across devices in a number of ways, or all of the functionality may be integrated into a dedicated, standalone device or other hardware. In another aspect, the means for performing the steps associated with the processes described in the disclosure may include any of the hardware and/or software described in the disclosure. All such permutations and combinations are intended to fall within the scope of the disclosure.

The elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described in the disclosure may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

Software also includes data. However, data and instructions are not mutually-exclusive categories. In various embodiments, the instructions may be used as data in one or more operations. As another example, instructions may be derived from data. The functional blocks and flowchart elements in this disclosure serve as software specifications, which can be translated into software by the routine work of a skilled technician or programmer. Software may include and/or rely on firmware, processor microcode, an operating system (OS), a basic input/output system (BIOS), application programming interfaces (APIs), libraries such as dynamic-link libraries (DLLs), device drivers, hypervisors, user applications, background services, background applications, etc. Software includes native applications and web applications. For example, a web application may be served to a device through a browser using hypertext markup language 5th revision (HTML5).

Software may include artificial intelligence systems, which may include machine learning or other computational intelligence. For example, artificial intelligence may include one or more models used for one or more problem domains. When presented with many data features, identification of a subset of features that are relevant to a problem domain may improve prediction accuracy, reduce storage space, and increase processing speed. This identification may be referred to as feature engineering. Feature engineering may be performed by users or may only be guided by users. In various implementations, a machine learning system may computationally identify relevant features, such as by performing singular value decomposition on the contributions of different features to outputs.

Examples of the models include recurrent neural networks (RNNs) such as long short-term memory (LSTM), deep learning models such as transformers, decision trees, support-vector machines, genetic algorithms, Bayesian networks, and regression analysis. Examples of systems based on a transformer model include bidirectional encoder representations from transformers (BERT) and generative pre-trained transformers (GPT). Training a machine-learning model may include supervised learning (for example, based on labelled input data), unsupervised learning, and reinforcement learning. In various embodiments, a machine-learning model may be pre-trained by their operator or by a third party. Problem domains include nearly any situation where structured data can be collected, and includes natural language processing (NLP), computer vision (CV), classification, image recognition, etc.

Some or all of the software may run in a virtual environment rather than directly on hardware. The virtual environment may include a hypervisor, emulator, sandbox, container engine, etc. The software may be built as a virtual machine, a container, etc. Virtualized resources may be controlled using, for example, a DOCKER container platform, a pivotal cloud foundry (PCF) platform, etc.

In a client-server model, some of the software executes on first hardware identified functionally as a server, while other of the software executes on second hardware identified functionally as a client. The identity of the client and server is not fixed: for some functionality, the first hardware may act as the server while for other functionality, the first hardware may act as the client. In different embodiments and in different scenarios, functionality may be shifted between the client and the server. In one dynamic example, some functionality normally performed by the second hardware is shifted to the first hardware when the second hardware has less capability. In various embodiments, the term "local" may be used in place of "client," and the term "remote" may be used in place of "server."

Some or all of the software may be logically partitioned into microservices. Each microservice offers a reduced subset of functionality. In various embodiments, each microservice may be scaled independently depending on load, either by devoting more resources to the microservice or by instantiating more instances of the microservice. In various embodiments, functionality offered by one or more microservices may be combined with each other and/or with other software not adhering to a microservices model.

Some or all of the software may be arranged logically into layers. In a layered architecture, a second layer may be logically placed between a first layer and a third layer. The first layer and the third layer would then generally interact with the second layer and not with each other. In various embodiments, this is not strictly enforced—that is, some direct communication may occur between the first and third layers.

Further Information and Use of Terms

The background description is presented simply for context, and is not necessarily well-understood, routine, or conventional. Further, the background description is not an admission of what does or does not qualify as prior art. In fact, some or all of the background description may be work attributable to the named inventors that is otherwise unknown in the art.

While only a few embodiments of the disclosure have been shown and described, it will be obvious to those skilled in the art that many changes and modifications may be made thereunto without departing from the spirit and scope of the disclosure as described in the following claims. All patent applications and patents, both foreign and domestic, and all other publications referenced herein are incorporated herein in their entireties to the full extent permitted by law. While the disclosure has been disclosed in connection with the preferred embodiments shown and described in detail, various modifications and improvements thereon will become readily apparent to those skilled in the art. Accordingly, the spirit and scope of the disclosure is not to be limited by the foregoing examples, but is to be understood in the broadest sense allowable by law.

The detailed description includes specific examples for illustration only, and not to limit the disclosure or its applicability. The examples are not intended to be an exhaustive list, but instead simply demonstrate possession by the inventors of the full scope of the currently presented and envisioned future claims. Variations, combinations, and equivalents of the examples are within the scope of the disclosure. No language in the specification should be construed as indicating that any non-claimed element is essential or critical to the practice of the disclosure.

While the foregoing written description enables one skilled to make and use what is considered presently to be the best mode thereof, those skilled in the art will understand and appreciate the existence of variations, combinations, and equivalents of the specific embodiment, method, and examples herein. The disclosure should therefore not be limited by the above-described embodiment, method, and examples, but by all embodiments and methods within the scope and spirit of the disclosure.

Each publication referenced in this disclosure, including foreign and domestic patent applications and patents, is hereby incorporated by reference in its entirety as if fully set forth herein.

The terms "comprising," "with," "including," and "containing" are to be construed as open-ended terms (i.e., meaning "including, but not limited to") unless otherwise noted. Unless otherwise specified, the terms "comprising," "having," "with," "including," and "containing," and their variants, are open-ended terms, meaning "including, but not limited to."

The term "exemplary" simply means "example" and does not indicate a best or preferred example. The use of any and all examples, or exemplary language (e.g., "such as") provided herein, is intended merely to better illuminate the disclosure and does not pose a limitation on the scope of the disclosure unless otherwise claimed.

The use of the terms "a," "an," "the," and similar referents in the context of describing the disclosure (especially in the context of the following claims) is to be construed to cover both the singular and the plural, unless otherwise indicated herein or clearly contradicted by context.

Recitations of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

The phrase "at least one of A, B, and C" should be construed to mean a logical (A OR B OR C), using a non-exclusive logical OR, and should not be construed to mean "at least one of A, at least one of B, and at least one of C."

The term "set" may include a set with a single member. The term "set" does not necessarily exclude the empty set—in other words, in some circumstances a "set" may have zero elements. The term "non-empty set" may be used to indicate exclusion of the empty set—that is, a non-empty set must have one or more elements. The term "subset" does not necessarily require a proper subset. In other words, a "subset" of a first set may be coextensive with (equal to) the first set. Further, the term "subset" does not necessarily exclude the empty set—in some circumstances a "subset" may have zero elements.

Physical (such as spatial and/or electrical) and functional relationships between elements (for example, between modules, circuit elements, semiconductor layers, etc.) are described using various terms. Unless explicitly described as being "direct," when a relationship between first and second elements is described, that relationship encompasses both (i) a direct relationship where no other intervening elements are present between the first and second elements and (ii) an indirect relationship where one or more intervening elements are present between the first and second elements. Example relationship terms include "adjoining," "transmitting," "receiving," "connected," "engaged," "coupled," "adjacent," "next to," "on top of," "above," "below," "abutting," and "disposed."

Although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of multiple embodiments remain within the scope of this disclosure.

One or more elements (for example, steps within a method, instructions, actions, or operations) may be executed in a different order (and/or concurrently) without altering the principles of the present disclosure. Unless technically infeasible, elements described as being in series may be implemented partially or fully in parallel. Similarly, unless technically infeasible, elements described as being in parallel may be implemented partially or fully in series.

While the disclosure describes structures corresponding to claimed elements, those elements do not necessarily invoke a means plus function interpretation unless they explicitly use the signifier "means for." Unless otherwise indicated, recitations of ranges of values are merely intended to serve as a shorthand way of referring individually to each separate value falling within the range, and each separate value is hereby incorporated into the specification as if it were individually recited.

While the drawings divide elements of the disclosure into different functional blocks or action blocks, these divisions are for illustration only. According to the principles of the present disclosure, functionality can be combined in other ways such that some or all functionality from multiple separately-depicted blocks can be implemented in a single functional block; similarly, functionality depicted in a single block may be separated into multiple blocks. Unless explicitly stated as mutually exclusive, features depicted in different drawings can be combined consistent with the principles of the present disclosure.

In the drawings, reference numbers may be reused to identify identical elements or may simply identify elements that implement similar functionality. Numbering or other labeling of instructions or method steps is done for convenient reference, not to indicate a fixed order. In the drawings, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. As one example, for information sent from element A to element B, element B may send requests and/or acknowledgements to element A.

What is claimed is:

1. An injectable administration compliance platform for real-time monitoring and management of adherence to a program for administration of a set of injectables, the injectable administration compliance platform comprising:
- a server configured to receive administration data from a wireless module associated with an intelligent injection device, wherein the administration data includes at least one of: an injection device ID, a drug ID, a patient ID, a potency value, an administration completion flag, a timestamp, or temperature data;
- a database configured to store treatment schedules associated with injectable medication administration;
- one or more processors and one or more memories comprising:
  - an artificial intelligence module configured to:
    - calculate a compliance score for an injection event based on conformance of the administration data to at least one criterion of a treatment schedule of the treatment schedules, and
    - compare the compliance score to a compliance threshold metric to categorize the injection event as one of compliant, non-compliant or indeterminate;
  - an alerts module configured to generate and send notifications to a user based on categorization of the injection event;
  - a monitoring system configured to track user compliance with prescribed medication regimens in substantially real-time;
- a recommendation system configured to generate personalized health suggestions based on received patient data;
- a reporting module configured to generate adherence reports for healthcare providers;
- a verification module configured to ensure proper medication administration by validating user identity;
- wherein the verification module is operatively coupled to a locking mechanism, wherein the verification module is further configured to actuate the locking mechanism to transition the intelligent injection device from a locked state that physically prevents injection administration to an unlocked state that physically allows the injection administration responsive to the verification module validating the user identity prior to the injection administration; and
- a dashboard configured to provide visual information related to injection administration compliance;
- wherein the injectable administration compliance platform is configured to:
  - receive additional data from at least one of: an IoT device, a wearable device, or an electronic medical record system,
  - process the additional data in combination with the administration data to make medical determinations, and
  - automatically determine changes to at least one of: dosage, timing, and attributes of the injection administration based on processing the additional data.

2. The injectable administration compliance platform of claim 1, wherein the program is prescribed by a physician and stored in the database.

3. The injectable administration compliance platform of claim 1, wherein the injectable administration compliance platform receives the administration data collected from the intelligent injection device, wherein the administration data includes at least one of: substance type, substance amount ejected, duration of substance release, temperature of substance, and substance identifier.

4. The injectable administration compliance platform of claim 1, wherein the injectable administration compliance platform uses the administration data to make medical treatment determinations, wherein the medical treatment determinations include at least one of: adjustments to patient treatment based on the administration data and changes to the dosage or the timing based on the received patient data.

5. The injectable administration compliance platform of claim 1, wherein the injectable administration compliance platform uses the administration data to make insurance coverage determinations, wherein the insurance coverage determinations include at least one of: increasing or lowering insurance rates and claim payouts based on whether the administration data indicates legitimate or fraudulent injection.

6. The injectable administration compliance platform of claim 1, wherein the injectable administration compliance platform uses the administration data to make manufacturing determinations, wherein the manufacturing determinations include at least one of: design adjustments, assembly adjustments, and factory adjustments based on the administration data.

7. The injectable administration compliance platform of claim 1, wherein the injectable administration compliance platform uses the administration data in connection with clinical trials of injectable medications, wherein the injectable administration compliance platform records exact injection timing to ensure accurate reporting and adherence to clinical trial protocols.

8. The injectable administration compliance platform of claim 1, wherein the injectable administration compliance platform uses the administration data to make a legal and regulatory compliance determination through a compliance/reporting/validation system that ensures regulatory requirements are met.

9. The injectable administration compliance platform of claim 8, wherein the legal and regulatory compliance determination is based at least in part on location-specific or jurisdiction-specific constraints or requirements through a privacy/governance system that protects the received patient data according to legal standards in regions with data protection laws.

10. The injectable administration compliance platform of claim 1, wherein the injectable administration compliance platform is integrated with at least one of an emergency medical record (EMR) system or an emergency health record (EHR) system, wherein integration enables automatic population of one or more fields of the at least one of the EMR system/or the EHR fields with the administration data.

11. The injectable administration compliance platform of claim 1, wherein the injectable administration compliance platform is integrated with a clinical provider or caregiver portal configured to enable healthcare providers to monitor compliance remotely and make treatment and coverage decisions based on stored treatment data.

12. The injectable administration compliance platform of claim 1, wherein the injectable administration compliance platform is integrated with a patient portal configured to enable the user to:
manage the treatment schedules,
view medication history,
manage appointments,
refill prescriptions, and
communicate with healthcare providers.

13. The injectable administration compliance platform of claim 10, wherein a set of events from the intelligent injection device are automatically delivered to populate the one or more fields of the at least one of the EMR system or the EHR system, wherein the set of events include the administration data comprising at least one of:
the injection device ID,
the drug ID,
the patient ID,
the potency value,
the administration completion flag,
the timestamp, and
the temperature data.

14. A platform for managing injectable medication administration, comprising:
a server configured to receive administration data from an intelligent injection device;
a database configured to store treatment schedules;
one or more processors and one or more memories comprising:
an artificial intelligence module configured to:
calculate a compliance score for an injection event based on the administration data and a treatment schedule of the treatment schedules, and
categorize the injection event as compliant or non-compliant;
an alerts module configured to generate notifications based on the categorization of the injection event;
a verification module configured to ensure proper medication administration by validating user identity;
wherein the verification module is operatively coupled to a locking mechanism, wherein the verification module is further configured to actuate the locking mechanism to transition the intelligent injection device from a locked state that physically prevents injection administration to an unlocked state that physically allows the injection administration responsive to the verification module validating the user identity prior to the injection administration; and
a dashboard configured to provide visual information related to injection administration compliance;
wherein the platform is configured to process the administration data to make at least one of:
medical determinations,
insurance coverage determinations, and
manufacturing determinations.

15. The platform of claim 14, wherein the artificial intelligence module is further configured to:
learn from a training set of data to optimize scheduling of future injection administration actions,
detect user behaviors that negatively impact wellness or injection programs, and generate alerts to warn the users about the user behaviors.

16. The platform of claim 14, wherein the artificial intelligence module is further configured to:
determine whether the intelligent injection device was fraudulently used or wasted based on the administration data, and
trigger alerts or prevention mechanisms if fraudulent use is detected.

17. The platform of claim 14, wherein the platform is integrated with at least one of:
an IoT device configured to collect environmental data,
a wearable devices configured to collect patient biometric data, and
an electronic medical record systems configured to store patient treatment data.

18. The platform of claim 14, wherein the verification module is further configured to:
validate authenticity of the intelligent injection device, and
prevent medication errors in institutional settings.

19. The platform of claim 14, wherein the platform further includes a custody and supply chain management system configured to:
track medications from manufacturer to patient,
ensure the medications are securely managed,
reduce risk of errors and fraud, and
enhance patient safety.

20. A method for managing administration of injectable medications via an injectable administration compliance platform, comprising:
receiving, by a server, administration data from a wireless module associated with an intelligent injection device, wherein the administration data includes at least one of: an injection device ID, a drug ID, a patient ID, a potency value, an administration completion flag, a timestamp, and temperature data;
storing treatment schedules in a database associated with the injectable administration compliance platform;
calculating, by an artificial intelligence module, a compliance score for an injection event based on conformance of the administration data to at least one criterion of a treatment schedule of the treatment schedules;

comparing the compliance score to a compliance threshold metric to categorize the injection event as one of compliant, non-compliant or indeterminate;

generating and sending, by an alerts module, a message summarizing categorization of the injection event to a party associated with the treatment schedule;

providing a user interface for controlling and configuring the platform;

tracking user compliance with a medication regimen through a monitoring system;

generating personalized health suggestions based on patient data through a recommendation system;

generating detailed reports on patient adherence through a reporting module;

verifying medication is being administered by or to a correct person through a verification module;

actuating a locking mechanism to transition the intelligent injection device from a locked state that prevents injection administration to an unlocked state that allows the injection administration responsive to the verification module verifying the medication is being administered by or to the correct person prior to the injection administration;

displaying visual information related to injection administration compliance through a dashboard;

receiving additional data from at least one of: an IoT device, a wearable device, and an electronic medical record system; and processing the additional data in combination with the administration data to automatically determine changes to at least one of: dosage, timing, and attributes of injection.

* * * * *